United States Patent
Tang et al.

(10) Patent No.: US 6,610,536 B2
(45) Date of Patent: Aug. 26, 2003

(54) NUCLEIC ACIDS AND POLYPEPTIDES

(75) Inventors: Y. Tom Tang, San Jose, CA (US); Ryle Goodrich, San Jose, CA (US); Vinod Asundi, Foster City, CA (US); Radoje T. Drmanac, Palo Alto, CA (US)

(73) Assignee: NUVELO, Inc., Sunnyvale, CA (US)

( * ) Notice: Subject to any disclaimer, the term of this patent is extended or adjusted under 35 U.S.C. 154(b) by 0 days.

(21) Appl. No.: 09/808,701

(22) Filed: Mar. 14, 2001

(65) Prior Publication Data

US 2002/0146757 A1 Oct. 10, 2002

Related U.S. Application Data

(63) Continuation-in-part of application No. 09/649,167, filed on Aug. 23, 2000, now abandoned, which is a continuation-in-part of application No. 09/540,217, filed on Mar. 31, 2000, now abandoned.

(51) Int. Cl.$^7$ ............................. C12N 5/02; C12N 15/12
(52) U.S. Cl. ..................... 435/325; 536/23.1; 536/23.5; 435/6; 435/320.1
(58) Field of Search ................. 536/23.1, 23.5; 435/6, 69.1, 69.4, 320.1, 325

(56) References Cited

PUBLICATIONS

Shao et al., "ANovel RalGEF–like Protein, RGL3, as a Candidate Effector for Rit and Ras*", Journal of Biological Chemistry vol. 275 No. 35 Sep. 1,2000 pp. 26914–29624.*
GenBank Accession No. AAK91126.
GenBank Accession No. NP_076111.
Genbank Accession No. BAB84908.
Ehrhardt, G.R. et al. (2001) A novel potential effector of M–Ras and p21 Ras negatively regulates p21 Ras–mediated gene induction and cell growth. Oncogene 20:188–197.

* cited by examiner

Primary Examiner—Marianne P. Allen
(74) Attorney, Agent, or Firm—Elene Quertermous

(57) ABSTRACT

The present invention provides novel nucleic acids, novel polypeptide sequences encoded by these nucleic acids and uses thereof.

7 Claims, No Drawings

SEQUENCE LISTING

```
<160> NUMBER OF SEQ ID NOS: 34

<210> SEQ ID NO 1
<211> LENGTH: 1210
<212> TYPE: DNA
<213> ORGANISM: Homo sapiens
<220> FEATURE:
<221> NAME/KEY: CDS
<222> LOCATION: (251)..(1027)
<223> OTHER INFORMATION:

<400> SEQUENCE: 1
tatctttcag tgcaggcctg gcatctcttg ggcacacacc gattcgtgca tgtagttgac      60
agtgaataag ctaaatgtgc atttgatgcc actctagggc gtatgccaga tactgggtta     120
ggcttcatgt gctccaggtg accaaagtct gaccccctag cctggacagg tttcctgtct     180
ggccctcgct gatctctgaa cctgtgccac ttttgttctg ctgccctgcc attcctctct     240
tacacacctg atg tct cct gca gtt gtg cca aat ctt tgg agt gtt gat         289
            Met Ser Pro Ala Val Val Pro Asn Leu Trp Ser Val Asp
            1               5                   10 gga gaa gtt aca gta gct gaa cag aag ccg gga gaa att gct gaa gaa        337
Gly Glu Val Thr Val Ala Glu Gln Lys Pro Gly Glu Ile Ala Glu Glu
    15                  20                  25 ctc gca agc tcc tac gaa aga aag ctc atc gag gtg gca gag atg cat        385
Leu Ala Ser Ser Tyr Glu Arg Lys Leu Ile Glu Val Ala Glu Met His
30                  35                  40                  45 ggc gag ctg att gag ttc aac gag cgc ctg cac agg gcc ctg gta gcc        433
Gly Glu Leu Ile Glu Phe Asn Glu Arg Leu His Arg Ala Leu Val Ala
                50                  55                  60 aag gaa gcc ctc gtg tcc cag atg agg cag gag ctc atc gat ctc cgg        481
Lys Glu Ala Leu Val Ser Gln Met Arg Gln Glu Leu Ile Asp Leu Arg
            65                  70                  75
```

-continued

```
gga ccg gtg cct gga gat ttg agt caa acg tcc gaa gac cag agt ttg      529
Gly Pro Val Pro Gly Asp Leu Ser Gln Thr Ser Glu Asp Gln Ser Leu
         80                  85                  90 tcg gat ttt gaa ata tca aac cgg gcg ctg atc aac gtc tgg atc ccc      577
Ser Asp Phe Glu Ile Ser Asn Arg Ala Leu Ile Asn Val Trp Ile Pro
 95                 100                 105 tca gtg ttt ctc cgg ggc aaa gca gca aat gca ttc cac gtg tat cag      625
Ser Val Phe Leu Arg Gly Lys Ala Ala Asn Ala Phe His Val Tyr Gln
110                 115                 120                 125 gtc tac atc cgg ata aaa gac gat gaa tgg aat att tat cgc cgg tat      673
Val Tyr Ile Arg Ile Lys Asp Asp Glu Trp Asn Ile Tyr Arg Arg Tyr
                130                 135                 140 aca gag ttc agg agt ttg cac cac aag tta caa aac aag tac cct caa      721
Thr Glu Phe Arg Ser Leu His His Lys Leu Gln Asn Lys Tyr Pro Gln
            145                 150                 155 gtg agg gcc tac aac ttc cca ccc aaa aag gcc att gga aac aag gat      769
Val Arg Ala Tyr Asn Phe Pro Pro Lys Lys Ala Ile Gly Asn Lys Asp
        160                 165                 170 gcc aag ttt gtg gag gaa cgg aga aag cag ctc cag aat tac ctg cgc      817
Ala Lys Phe Val Glu Glu Arg Arg Lys Gln Leu Gln Asn Tyr Leu Arg
    175                 180                 185 agc gtc atg aac aaa gtc atc cag atg gtc ccc gag ttc gct gcc agc      865
Ser Val Met Asn Lys Val Ile Gln Met Val Pro Glu Phe Ala Ala Ser
190                 195                 200                 205 ccc aag aag gag acc ctc atc cag ctg atg ccc ttc ttc gtc gac atc      913
Pro Lys Lys Glu Thr Leu Ile Gln Leu Met Pro Phe Phe Val Asp Ile
                210                 215                 220 acc ccg ccc gga gag cct gtg aac agc cgg ccc aaa gca gct tcc cgc      961
Thr Pro Pro Gly Glu Pro Val Asn Ser Arg Pro Lys Ala Ala Ser Arg
            225                 230                 235 ttt ccc aaa ctg tcc cgg ggt cag ccc cgg gag acc cgc aac gtg gag     1009
Phe Pro Lys Leu Ser Arg Gly Gln Pro Arg Glu Thr Arg Asn Val Glu
        240                 245                 250 ccc cag agc ggt gac ctc tgacctcgac aaaaccgcag ccacgggccc            1057
Pro Gln Ser Gly Asp Leu
    255 tgtgcgtggc accagctgcg tccaccccag ccactgccgc tggcccctca cctcagcgtg   1117 acaaccacgt cccactggtg atcctgagag cacacgattc ccaacagtta cacaacaccc   1177 cgattaaact aatcagtctt caaaaaaaaa aaa                                1210

<210> SEQ ID NO 2
<211> LENGTH: 2957
<212> TYPE: DNA
<213> ORGANISM: Homo sapiens
<220> FEATURE:
<221> NAME/KEY: CDS
<222> LOCATION: (330)..(2870)
<223> OTHER INFORMATION:

<400> SEQUENCE: 2
ggcaaggtct catgggaaag gtcatgtctc tcgaagaaag gttataaacc ctgagatatg     60
agggttgggc gagacatccg agcctgtttc gttccgtgtt gggaccagga ataaccctga    120
cttctgagct tcataaccc caggatcctc cagaaaattt gcggcgcgct gagggaaaac     180
cttgctgaag ctgtacattg gaatgcgttt acagtcattg taatggaagc aaaatacatg    240
aaggaaaaac tgttatttgt atccctgctt attgcacctg acgactagtt gcagatggtt    300
ttgtttacct aagaaaactt gtgatataa atg aaa aaa aca cct gtt ttc cta      353
                                 Met Lys Lys Thr Pro Val Phe Leu
```

-continued

```
                        1                           5
gag tca ttg gtt aca aat atg ctt cgt cta aga gct att tgt cca ttc    401
Glu Ser Leu Val Thr Asn Met Leu Arg Leu Arg Ala Ile Cys Pro Phe
     10              15                  20 tcc tgg aga gtg ttt caa ttt cga ccc atc agt tgt gaa cca cta att    449
Ser Trp Arg Val Phe Gln Phe Arg Pro Ile Ser Cys Glu Pro Leu Ile
 25              30                  35                  40 att cag atg aat aag tgt aca gat gag gag caa atg ttt ggt ttt att    497
Ile Gln Met Asn Lys Cys Thr Asp Glu Glu Gln Met Phe Gly Phe Ile
                 45                  50                  55 gaa aga aac aaa gcc ata ctt tca gaa aag caa gtg gga tgt gca ttt    545
Glu Arg Asn Lys Ala Ile Leu Ser Glu Lys Gln Val Gly Cys Ala Phe
                 60                  65                  70 gat atg ctt tgg aag ctt caa aag cag aag acc agc ctg tta aaa aat    593
Asp Met Leu Trp Lys Leu Gln Lys Gln Lys Thr Ser Leu Leu Lys Asn
     75              80                  85 gct gag tat gtc aga gac cat cct caa ttt ctt act ctt cat aat tta    641
Ala Glu Tyr Val Arg Asp His Pro Gln Phe Leu Thr Leu His Asn Leu
     90              95                 100 gct aca aat aaa ttc aaa tta atg aat gac gat acc ctg gtg aat gtg    689
Ala Thr Asn Lys Phe Lys Leu Met Asn Asp Asp Thr Leu Val Asn Val
105             110                 115                 120 tta tac gtc aca caa cag ttt gct ggt gag gcc cat gac ccg cta gtt    737
Leu Tyr Val Thr Gln Gln Phe Ala Gly Glu Ala His Asp Pro Leu Val
                125                 130                 135 gaa gca cta gtt aca gaa gca tgg aga agg cta gaa agg ttt gat att    785
Glu Ala Leu Val Thr Glu Ala Trp Arg Arg Leu Glu Arg Phe Asp Ile
                140                 145                 150 aaa ctg ctc tca gaa ttt tcc tct tgc cta gca gat cag cat ttg tat    833
Lys Leu Leu Ser Glu Phe Ser Ser Cys Leu Ala Asp Gln His Leu Tyr
                155                 160                 165 ttt agt cca tta atg gga aaa ata gct gat att gtt cat agg aac ttg    881
Phe Ser Pro Leu Met Gly Lys Ile Ala Asp Ile Val His Arg Asn Leu
     170                 175                 180 gaa acc aca cag gac tta agt tcc ttg tct gtc ttg atg gtc aac ata    929
Glu Thr Thr Gln Asp Leu Ser Ser Leu Ser Val Leu Met Val Asn Ile
185             190                 195                 200 tct tct tta ata tca cga cat ttt caa caa caa ctg gtg aac aaa aca    977
Ser Ser Leu Ile Ser Arg His Phe Gln Gln Gln Leu Val Asn Lys Thr
                205                 210                 215 gaa ctt ctt ttt gac acc ata gat tct tct gag gtc aac gtt gca aaa   1025
Glu Leu Leu Phe Asp Thr Ile Asp Ser Ser Glu Val Asn Val Ala Lys
                220                 225                 230 agc ata gca aag ttt ctt cga aat gtt aga tat cgt tat caa cca cta   1073
Ser Ile Ala Lys Phe Leu Arg Asn Val Arg Tyr Arg Tyr Gln Pro Leu
         235                 240                 245 tta gaa aga tgt aat aac gta ttt tta agt aat gtg gac cac ctt gat   1121
Leu Glu Arg Cys Asn Asn Val Phe Leu Ser Asn Val Asp His Leu Asp
     250                 255                 260 ttg gat tcc atc agt aaa ata ctt agt gta tac aaa ttt cta caa ttt   1169
Leu Asp Ser Ile Ser Lys Ile Leu Ser Val Tyr Lys Phe Leu Gln Phe
265                 270                 275                 280 aat agt ttt gaa ttt att ata atg gct aaa aag aag cta act gaa atg   1217
Asn Ser Phe Glu Phe Ile Ile Met Ala Lys Lys Lys Leu Thr Glu Met
                285                 290                 295 att cct ctg tgt aat cat cct gct agc ttt gta aaa ttg ttt gta gca   1265
Ile Pro Leu Cys Asn His Pro Ala Ser Phe Val Lys Leu Phe Val Ala
                300                 305                 310 ttg gga ccc att gca gga cct gaa gaa aag aaa caa ctt aaa tca act   1313
```

-continued

```
Leu Gly Pro Ile Ala Gly Pro Glu Glu Lys Lys Gln Leu Lys Ser Thr
        315                 320                 325 atg tta ttg atg tca gag gac cta act ggc gag caa gcc ctg gca gtg     1361
Met Leu Leu Met Ser Glu Asp Leu Thr Gly Glu Gln Ala Leu Ala Val
    330                 335                 340 ttg gga gca atg gga gat atg gaa agc aga aac tca tgt ctg att aaa     1409
Leu Gly Ala Met Gly Asp Met Glu Ser Arg Asn Ser Cys Leu Ile Lys
345                 350                 355                 360 aga gtt act tca gtt ctg cat aaa cat ttg gat ggc tat aaa cca tta     1457
Arg Val Thr Ser Val Leu His Lys His Leu Asp Gly Tyr Lys Pro Leu
                365                 370                 375 gag ttg ttg aag ata act caa gaa ttg act ttt ctg cat ttc caa agg     1505
Glu Leu Leu Lys Ile Thr Gln Glu Leu Thr Phe Leu His Phe Gln Arg
            380                 385                 390 aag gag ttt ttt gcg aaa ctt aga gaa tta ctg ctt agt tat ttg aaa     1553
Lys Glu Phe Phe Ala Lys Leu Arg Glu Leu Leu Leu Ser Tyr Leu Lys
        395                 400                 405 aat agt ttc ata cca act gag gtg tct gtt ctg gtc cgt gct att tcc     1601
Asn Ser Phe Ile Pro Thr Glu Val Ser Val Leu Val Arg Ala Ile Ser
    410                 415                 420 ctg ctc cct tct cct cac ttg gac gaa gtg ggg ata tcc cga att gaa     1649
Leu Leu Pro Ser Pro His Leu Asp Glu Val Gly Ile Ser Arg Ile Glu
425                 430                 435                 440 gcc gtt tta cca cag tgt gac cta aat aac ctg agt agt ttt gcc aca     1697
Ala Val Leu Pro Gln Cys Asp Leu Asn Asn Leu Ser Ser Phe Ala Thr
                445                 450                 455 tct gtt tta aga tgg att cag cat gat cac gtg tat ttg gat aat atg     1745
Ser Val Leu Arg Trp Ile Gln His Asp His Val Tyr Leu Asp Asn Met
            460                 465                 470 act gcg aaa caa ctg aaa cta ctt caa aaa tta gat cac tat ggt cgt     1793
Thr Ala Lys Gln Leu Lys Leu Leu Gln Lys Leu Asp His Tyr Gly Arg
        475                 480                 485 cag aga cta caa cac agc aac agt ttg gat ctg tta cgg aag gaa ctt     1841
Gln Arg Leu Gln His Ser Asn Ser Leu Asp Leu Leu Arg Lys Glu Leu
    490                 495                 500 aaa tct ctc aaa gga aac acg ttt cct gag tca ctt ctt gaa gaa atg     1889
Lys Ser Leu Lys Gly Asn Thr Phe Pro Glu Ser Leu Leu Glu Glu Met
505                 510                 515                 520 att gct act tta cag cat ttc atg gat gat att aat tac ata aat gtt     1937
Ile Ala Thr Leu Gln His Phe Met Asp Asp Ile Asn Tyr Ile Asn Val
                525                 530                 535 ggg gag att gca tct ttt att tct agt act gat tac ctc agt act ttg     1985
Gly Glu Ile Ala Ser Phe Ile Ser Ser Thr Asp Tyr Leu Ser Thr Leu
            540                 545                 550 cta cta gat agg ata gcc tca gtg gct gtt cag cag att gaa aag atc     2033
Leu Leu Asp Arg Ile Ala Ser Val Ala Val Gln Gln Ile Glu Lys Ile
        555                 560                 565 cat cct ttt aca atc cct gct att att cgt cca ttc agc gta ttg aac     2081
His Pro Phe Thr Ile Pro Ala Ile Ile Arg Pro Phe Ser Val Leu Asn
    570                 575                 580 tat gat cca cct caa agg gat gaa ttt ttg gga act tgc gtg caa cat     2129
Tyr Asp Pro Pro Gln Arg Asp Glu Phe Leu Gly Thr Cys Val Gln His
585                 590                 595                 600 ctt aat tct tac tta ggt ata ttg gat cct ttt ata tta gtg ttt ctt     2177
Leu Asn Ser Tyr Leu Gly Ile Leu Asp Pro Phe Ile Leu Val Phe Leu
                605                 610                 615 ggt ttc tct ttg gcc aca ctt gaa tat ttt cca gaa gat ctg cta aag     2225
Gly Phe Ser Leu Ala Thr Leu Glu Tyr Phe Pro Glu Asp Leu Leu Lys
            620                 625                 630
```

-continued

```
gca att ttt aac atc aaa ttc tta gct aga ttg gat tct caa ctt gaa      2273
Ala Ile Phe Asn Ile Lys Phe Leu Ala Arg Leu Asp Ser Gln Leu Glu
        635                 640                 645 att tta tct cca tct cga agt gca aga gtc cag ttt cat ctt atg gag      2321
Ile Leu Ser Pro Ser Arg Ser Ala Arg Val Gln Phe His Leu Met Glu
650                 655                 660 tta aat aga tca gtc tgc ttg gaa tgc cct gag ttt cag att cca tgg      2369
Leu Asn Arg Ser Val Cys Leu Glu Cys Pro Glu Phe Gln Ile Pro Trp
665                 670                 675                 680 ttt cat gac cgc ttc tgt caa caa tat aat aaa ggt att ggt ggc atg      2417
Phe His Asp Arg Phe Cys Gln Gln Tyr Asn Lys Gly Ile Gly Gly Met
                685                 690                 695 gat gga aca caa cag cag att ttt aaa atg tta gca gag gta cta gga      2465
Asp Gly Thr Gln Gln Gln Ile Phe Lys Met Leu Ala Glu Val Leu Gly
        700                 705                 710 gga atc aat tgt gta aaa gcc tcg gtt ctt acg cct tat tac cac aaa      2513
Gly Ile Asn Cys Val Lys Ala Ser Val Leu Thr Pro Tyr Tyr His Lys
        715                 720                 725 gta gat ttt gag tgt atc ttg gat aaa aga aaa aaa cct ctt ccg tat      2561
Val Asp Phe Glu Cys Ile Leu Asp Lys Arg Lys Lys Pro Leu Pro Tyr
730                 735                 740 gga agc cat aat ata gca ttg gga caa cta cca gaa atg ccc tgg gaa      2609
Gly Ser His Asn Ile Ala Leu Gly Gln Leu Pro Glu Met Pro Trp Glu
745                 750                 755                 760 tca aat atc gaa ata gtt gga tca agg ctg cca cca ggg gct gaa agg      2657
Ser Asn Ile Glu Ile Val Gly Ser Arg Leu Pro Pro Gly Ala Glu Arg
                765                 770                 775 att gct ttg gaa ttt ttg gat tca aaa gca ctt tgt aga aat atc cct      2705
Ile Ala Leu Glu Phe Leu Asp Ser Lys Ala Leu Cys Arg Asn Ile Pro
        780                 785                 790 cac atg aaa gga aaa tct gct atg aaa aaa cga cat ttg gaa att ctg      2753
His Met Lys Gly Lys Ser Ala Met Lys Lys Arg His Leu Glu Ile Leu
        795                 800                 805 ggg tat cgt gta att cag att tcc cag ttt gaa tgg aac tct atg gca      2801
Gly Tyr Arg Val Ile Gln Ile Ser Gln Phe Glu Trp Asn Ser Met Ala
810                 815                 820 ctg tca aca aag gat gct cgg atg gac tac ctg aga gaa tgt ata ttt      2849
Leu Ser Thr Lys Asp Ala Arg Met Asp Tyr Leu Arg Glu Cys Ile Phe
825                 830                 835                 840 gga gaa gtc aag tca tgt ttg tagtttttat ttaaaatgaa tgttatcgtg         2900
Gly Glu Val Lys Ser Cys Leu
                845 tgttacattt ggacctattt taataaagtg gcctgtctca attaaaaaaa aaaaaaa       2957

<210> SEQ ID NO 3
<211> LENGTH: 719
<212> TYPE: DNA
<213> ORGANISM: Homo sapiens
<220> FEATURE:
<221> NAME/KEY: CDS
<222> LOCATION: (73)..(546)
<223> OTHER INFORMATION:

<400> SEQUENCE: 3
cgtcttgggc tccatttgtg tctctaaatc aggtggcaga gcatttctat aacactggtt     60
gagaaagttc ag atg att gct gta atc cta gga tcc ctg ttc tta ata gcc    111
              Met Ile Ala Val Ile Leu Gly Ser Leu Phe Leu Ile Ala
              1               5                   10 agt gtg act tgg ctc ctc tgg tca gcc ttc agc ccc tat gca gtg tgg      159
Ser Val Thr Trp Leu Leu Trp Ser Ala Phe Ser Pro Tyr Ala Val Trp
15                  20                  25
```

```
cag agg aag gac atc ctt ttt cag atc tgc tat gga atg tat ggt ttt    207
Gln Arg Lys Asp Ile Leu Phe Gln Ile Cys Tyr Gly Met Tyr Gly Phe
 30              35                  40                  45 atg gat cta gtg tgc ata ggt ctc att gtt cat gaa gga gct gca gtt    255
Met Asp Leu Val Cys Ile Gly Leu Ile Val His Glu Gly Ala Ala Val
             50                  55                  60 tac aga gtg ttt aag cgc tgg cga gct gtg aat ttg cac tgg gat gtg    303
Tyr Arg Val Phe Lys Arg Trp Arg Ala Val Asn Leu His Trp Asp Val
             65                  70                  75 tta aat tat gac aaa gcc aca gac atc gaa gaa agc agc cgg gga gag    351
Leu Asn Tyr Asp Lys Ala Thr Asp Ile Glu Glu Ser Ser Arg Gly Glu
         80                  85                  90 tct tcc aca agt agg act ttg tgg tta cca ttg aca gct ctg cgg aac    399
Ser Ser Thr Ser Arg Thr Leu Trp Leu Pro Leu Thr Ala Leu Arg Asn
     95                 100                 105 aga aac ttg gtc cac cca act cag tta acc tca cca agg ttt cag tgt    447
Arg Asn Leu Val His Pro Thr Gln Leu Thr Ser Pro Arg Phe Gln Cys
110                 115                 120                 125 ggc tat gtg tta ttg cac ctg ttc aat cgg atg agg ccc cat gaa gac    495
Gly Tyr Val Leu Leu His Leu Phe Asn Arg Met Arg Pro His Glu Asp
                130                 135                 140 tta tca gaa gat aac agc tcg ggg gag gtt gtg atg aga gtg act tca    543
Leu Ser Glu Asp Asn Ser Ser Gly Glu Val Val Met Arg Val Thr Ser
                145                 150                 155 gtg tgacaaaagc ataagatgat gcagtgtgga ccaccctgca cattttgcaa         596
Val tgtaattgca gtgaatggca aaaccatagc acttctaaaa acacatctat gaactttta   656 aaatttatgc ttttatatg aacatttgaa ttgcaaatac attttctga gaaaaaaaa     716 aaa                                                                719

<210> SEQ ID NO 4
<211> LENGTH: 870
<212> TYPE: DNA
<213> ORGANISM: Homo sapiens
<220> FEATURE:
<221> NAME/KEY: CDS
<222> LOCATION: (25)..(669)
<223> OTHER INFORMATION:

<400> SEQUENCE: 4
tttcgtgcgg gcggaggagc ggcc atg ccg ccg cgg cgc atc atc gtg gag     51
                          Met Pro Pro Arg Arg Ile Ile Val Glu
                            1               5 gtg aag gtg cta gac gtg cag aag cgg cgg gtg ccc aac aag cat tat    99
Val Lys Val Leu Asp Val Gln Lys Arg Arg Val Pro Asn Lys His Tyr
 10                  15                  20                  25 gtc tac atc atc cgg gtc acg tgg tcc agc ggc tcc acc gag gcc att   147
Val Tyr Ile Ile Arg Val Thr Trp Ser Ser Gly Ser Thr Glu Ala Ile
             30                  35                  40 tac cgg cgc tac agc aag ttt ttt gac ctc cag atg cag atg ttg gac   195
Tyr Arg Arg Tyr Ser Lys Phe Phe Asp Leu Gln Met Gln Met Leu Asp
             45                  50                  55 aaa ttt ccc atg gaa gga gga cag aag gac ccc aag cag cgg atc atc   243
Lys Phe Pro Met Glu Gly Gly Gln Lys Asp Pro Lys Gln Arg Ile Ile
         60                  65                  70 ccc ttt ctg cca ggt aag att ctc ttc aga cga agc cac atc cgg gac   291
Pro Phe Leu Pro Gly Lys Ile Leu Phe Arg Arg Ser His Ile Arg Asp
         75                  80                  85 gtg gct gtc aaa cgc ctg ata cca att gat gaa tac tgt aag gcc ctc   339
```

-continued

```
                Val Ala Val Lys Arg Leu Ile Pro Ile Asp Glu Tyr Cys Lys Ala Leu
                 90                  95                 100                 105 atc cag ctg ccc ccc tac atc tct cag tgt gat gag gtg ctg cag ttc           387
Ile Gln Leu Pro Pro Tyr Ile Ser Gln Cys Asp Glu Val Leu Gln Phe
            110                 115                 120 ttt gag aca aga cct gag gac ctg aat ccc ccc aaa gag gag cac att           435
Phe Glu Thr Arg Pro Glu Asp Leu Asn Pro Pro Lys Glu Glu His Ile
            125                 130                 135 ggg aaa aag aaa tct ggg ggt gac caa acc tca gtg gac ccc atg gtc           483
Gly Lys Lys Lys Ser Gly Gly Asp Gln Thr Ser Val Asp Pro Met Val
            140                 145                 150 ctg gag cag tat gtg gtg gta gcc aac tac cag aag cag gag agt tcg           531
Leu Glu Gln Tyr Val Val Val Ala Asn Tyr Gln Lys Gln Glu Ser Ser
    155                 160                 165 gag atc agc ctc agc gtg ggg cag gtg gtg gac atc atc gag aag act           579
Glu Ile Ser Leu Ser Val Gly Gln Val Val Asp Ile Ile Glu Lys Thr
170                 175                 180                 185 gag tca ggt tgg tgg ttc gtc agc act gcc gag gag caa ggc tgg gtc           627
Glu Ser Gly Trp Trp Phe Val Ser Thr Ala Glu Glu Gln Gly Trp Val
                190                 195                 200 cct gca acg gtg cct cga agg gcc agg atg cgc gtg cag gga                   669
Pro Ala Thr Val Pro Arg Arg Ala Arg Met Arg Val Gln Gly
                205                 210                 215 tgaggttttc ctctgcagcc tgaacgaaag gagaaggtac aacagtcatc tacccgtaca         729
cagttcggac cacggatgac atgaacctgg aaagaggggt gtggtggcgg ccttccaaa          789 aacctggacg cttgagactc cgtcccgcaa aacggtggcc cccctactaa agaacggggc         849
ctgcccaaga ggcctgcacc a                                                    870

<210> SEQ ID NO 5
<211> LENGTH: 1329
<212> TYPE: DNA
<213> ORGANISM: Homo sapiens
<220> FEATURE:
<221> NAME/KEY: CDS
<222> LOCATION: (185)..(787)
<223> OTHER INFORMATION:

<400> SEQUENCE: 5
tttcgtgtct gcagcgccga gggaggctgc cagtgcgtga ggaagagagc tagagactgg          60
acaggggaga cagagcagcg tcggagccgc gcagggacg ggagtgagag cgggagtgag          120
agcaggaacg acgcagagcg gccgtcgccg tgcccgggtc tcaggcgcc tggctgaagt          180 gagc atg gct tca gtg gcc tgg gcc gtc ctc aag gtg ctg ctg ctt ctc          229
     Met Ala Ser Val Ala Trp Ala Val Leu Lys Val Leu Leu Leu Leu
     1               5                  10                  15 ccc act cag act tgg agc ccc gta gga gca gga aat cca cct gac tgt           277
Pro Thr Gln Thr Trp Ser Pro Val Gly Ala Gly Asn Pro Pro Asp Cys
            20                  25                  30 gat gcc cca ctg gcc tct gcc ttg cct agg tca tcc ttc agc agc tcc           325
Asp Ala Pro Leu Ala Ser Ala Leu Pro Arg Ser Ser Phe Ser Ser Ser
            35                  40                  45 tca gag ctg tcc agc agc cac ggc ccg ggg ttt tca agg ctt aat cga           373
Ser Glu Leu Ser Ser Ser His Gly Pro Gly Phe Ser Arg Leu Asn Arg
    50                  55                  60 aga gat gga gct ggt ggc tgg acc cca ctt gtg tca aat aaa tac caa           421
Arg Asp Gly Ala Gly Gly Trp Thr Pro Leu Val Ser Asn Lys Tyr Gln
65                  70                  75 tgg ctg caa att gac ctt gga gag aga atg gag gtc act gct gtc gcc           469
Trp Leu Gln Ile Asp Leu Gly Glu Arg Met Glu Val Thr Ala Val Ala
```

```
                80                  85                  90                  95
acc caa gga gga tat ggg agc tct gac tgg gtg acc agc tac ctc ctg           517
Thr Gln Gly Gly Tyr Gly Ser Ser Asp Trp Val Thr Ser Tyr Leu Leu
                        100                 105                 110 atg ttc agt gat ggt ggg aga aac tgg aag cag tat cgc cga gaa gaa           565
Met Phe Ser Asp Gly Gly Arg Asn Trp Lys Gln Tyr Arg Arg Glu Glu
            115                 120                 125 agc atc tgg ggt ttt cca gga aac aca aac gcg gac agt gtg gtg cac           613
Ser Ile Trp Gly Phe Pro Gly Asn Thr Asn Ala Asp Ser Val Val His
        130                 135                 140 tac aga ctc cag cct ccc ttt gaa gcc agg ttc ctg cgc ttt ctc cct           661
Tyr Arg Leu Gln Pro Pro Phe Glu Ala Arg Phe Leu Arg Phe Leu Pro
    145                 150                 155 tta gcc tgg gaa ccc cca ggg gca gga ttg gga tgc gga ttg aag tgt           709
Leu Ala Trp Glu Pro Pro Gly Ala Gly Leu Gly Cys Gly Leu Lys Cys
160                 165                 170                 175 acg gat gtg cat ata aat ctg agg tgg ttt att ttg atg gac aaa gtg           757
Thr Asp Val His Ile Asn Leu Arg Trp Phe Ile Leu Met Asp Lys Val
                        180                 185                 190 ctc tgc tgt ata cac ttg ata aaa aac ctt taaaaccact aagagatgtt            807
Leu Cys Cys Ile His Leu Ile Lys Asn Leu
                    195                 200 atttctttga aatttaaagc catgcagagc aatggaattc tacttcacag agaaggacaa         867
catggaaatc acattactct ggaattaatt aaaggaaagc ttgtcttttt tcttaactca         927
ggcaatgcta agctgccttc cactattgct cctgtgaccc tcaccctggg cagcctgctg         987
gatgaccagc actggcattc cgtcctcatc gagctcctcg acacgcaggt caacttcacc        1047
gtggacaaac acactcatca tttccaagca aagggagatt ccagtaactt ggatcttaat        1107
tttgagatca gctttggggg aattccgaca cccggaagat cgcgggcatt cacacgtaaa        1167
agctttcatg gtgtttaga aaatctttat tataatggag tggatgttac cgaattagcc        1227
aagaaacaca aaccacagat cctcatgatg gagttggctc atgggttgca ggaccaaaac        1287
ctgaaaatat ctctgactgt gtgtcaccag accacacaat ga                           1329

<210> SEQ ID NO 6
<211> LENGTH: 912
<212> TYPE: DNA
<213> ORGANISM: Homo sapiens
<220> FEATURE:
<221> NAME/KEY: CDS
<222> LOCATION: (332)..(574)
<223> OTHER INFORMATION:

<400> SEQUENCE: 6
tggcgaaccg cgaccggaat ccctggtcga cgatttcgcg ccccgccctg gtccagtgat          60
tgatcagcag tgattactga ggctttaatg gcccgcttgg atgggaatta attctgggat         120
ggataaataa tgcatcgagg tttatgtagt ccaaggcgag ccgtccgtcc ggagccagga         180
gaggtagccg agggagcctg acgggtgacg ccagcggcca cggggccccg aacgagcagg         240
acatgagggg cgactaggcg cgaggacgag caaaagcaag tggatgacag catgaacggc         300 cctgcgggc tggccggacg gctgcaagaa c atg ctg agc cca aag atc agg            352
                                    Met Leu Ser Pro Lys Ile Arg
                                     1               5 cag gcc agg agg gcc cgc tcc aaa agc cta gtg atg ggg gag cag agc           400
Gln Ala Arg Arg Ala Arg Ser Lys Ser Leu Val Met Gly Glu Gln Ser
        10                  15                  20 cgg agc cct ggg cgg atg ccg tgc cct cac agg ctg ggc ccc gtg ctg           448
```

```
                                             -continued

Arg Ser Pro Gly Arg Met Pro Cys Pro His Arg Leu Gly Pro Val Leu
        25                  30                  35 aag gcg ggc tgg ctg aag aag cag agg agc atc atg aag aac tgg cag    496
Lys Ala Gly Trp Leu Lys Lys Gln Arg Ser Ile Met Lys Asn Trp Gln
 40                  45                  50                  55 cag cgc tgg ttt gtg ctg cgt ggg gat cag ctt ttc tac tac aag gac    544
Gln Arg Trp Phe Val Leu Arg Gly Asp Gln Leu Phe Tyr Tyr Lys Asp
                 60                  65                  70 aaa gat gag atc aag ccc cag gag aat aag tgagggaagc tcagcaataa      594
Lys Asp Glu Ile Lys Pro Gln Glu Asn Lys
             75                  80 ggagccatag aagattgatt taaagtttga tgtgattgag taaaagcttg agactggtgg    654
ggagaaagtc aagatggatg ggaaagcaca tgcacttcta ggagtggaac attaatattg    714
gacagtcgga aaccagaaat ctttaagaaa gaggaaacct caggggaaga agagaggcc    774 atcctatccc ataacttgaa agtcacagga atatttcagc ctgcagggaa tcttcatttc    834
ccagcccatt gtttaccaaa cttgcacgtc aaaaacaaaa acaaaaaata aatgttgct    894 ttcatgaaaa aaaaaaaa                                                 912

<210> SEQ ID NO 7
<211> LENGTH: 2596
<212> TYPE: DNA
<213> ORGANISM: Homo sapiens
<220> FEATURE:
<221> NAME/KEY: CDS
<222> LOCATION: (61)..(1428)
<223> OTHER INFORMATION:

<400> SEQUENCE: 7
gaccaccttc agcaacttga acatgaggtg gaccccccctt tcacttccag gaaggtacat    60 atg gaa act aca gtg tcc aga ccg gtc ctt tct cca acc cac atc aac    108
Met Glu Thr Thr Val Ser Arg Pro Val Leu Ser Pro Thr His Ile Asn
  1               5                  10                  15 gct aca gct tct gaa aca ttc aca gta ctt cag caa agg atg aga ata    156
Ala Thr Ala Ser Glu Thr Phe Thr Val Leu Gln Gln Arg Met Arg Ile
                 20                  25                  30 gtt gag gaa cag acc agt tca ctg agg gat gac cta ata atg ttg gat    204
Val Glu Glu Gln Thr Ser Ser Leu Arg Asp Asp Leu Ile Met Leu Asp
             35                  40                  45 ttt ggt gaa aaa agg tcc cat gta aac agt ata aag gaa aga acg tca    252
Phe Gly Glu Lys Arg Ser His Val Asn Ser Ile Lys Glu Arg Thr Ser
 50                  55                  60 tca gtt ggt ttg cct agt gtt att cca aac tct aca cgc cgt gtg agc    300
Ser Val Gly Leu Pro Ser Val Ile Pro Asn Ser Thr Arg Arg Val Ser
 65                  70                  75                  80 ttt gca cct aac ctg cct tct atg aaa aca tct cag gat att gga gac    348
Phe Ala Pro Asn Leu Pro Ser Met Lys Thr Ser Gln Asp Ile Gly Asp
                 85                  90                  95 tct agg atc tct cta aag act ctt ttg aat gct att aaa acc atg gag    396
Ser Arg Ile Ser Leu Lys Thr Leu Leu Asn Ala Ile Lys Thr Met Glu
                100                 105                 110 gga aga ctg gaa ggc aaa ata gag att cta gcc tca aga cct tta ata    444
Gly Arg Leu Glu Gly Lys Ile Glu Ile Leu Ala Ser Arg Pro Leu Ile
            115                 120                 125 aat gat gaa tca cca aat ttt ctt aaa cag gac tcg gtg aaa tct att    492
Asn Asp Glu Ser Pro Asn Phe Leu Lys Gln Asp Ser Val Lys Ser Ile
130                 135                 140 ctt gaa aga agt aaa gag gag ctg tcc cga aca gtg aag tgt cgt aat    540
Leu Glu Arg Ser Lys Glu Glu Leu Ser Arg Thr Val Lys Cys Arg Asn
```

-continued

```
                145                 150                 155                 160
gcg gcc ctg aaa gag agt cag aag ttg aaa gaa gac ctc gag gct gtg      588
Ala Ala Leu Lys Glu Ser Gln Lys Leu Lys Glu Asp Leu Glu Ala Val
            165                 170                 175 gag gac agg gaa aac aag aag gca agg aat cag tcc ctt ctg acc gtg      636
Glu Asp Arg Glu Asn Lys Lys Ala Arg Asn Gln Ser Leu Leu Thr Val
        180                 185                 190 gga aac ttt cag cga caa ttg gca gaa gct aaa gaa gac aac tgc aaa      684
Gly Asn Phe Gln Arg Gln Leu Ala Glu Ala Lys Glu Asp Asn Cys Lys
        195                 200                 205 gtc aca atc atg ttg gag aat gtg ctg gct tct cac agt aag atg caa      732
Val Thr Ile Met Leu Glu Asn Val Leu Ala Ser His Ser Lys Met Gln
    210                 215                 220 ggt gct ctg gag aaa gta caa ata gag ctt ggg cgg agg gat tca gag      780
Gly Ala Leu Glu Lys Val Gln Ile Glu Leu Gly Arg Arg Asp Ser Glu
225                 230                 235                 240 att gca ggc ctc aag aaa gaa agg gat ctc aat caa cag agg gtg cag      828
Ile Ala Gly Leu Lys Lys Glu Arg Asp Leu Asn Gln Gln Arg Val Gln
            245                 250                 255 aag ctg gaa gct gaa gtg gac cag tgg cag gcc agg atg ctt gtc atg      876
Lys Leu Glu Ala Glu Val Asp Gln Trp Gln Ala Arg Met Leu Val Met
        260                 265                 270 gag gac cag cac aac agt gag att gaa tct cta caa aaa gct cta ggt      924
Glu Asp Gln His Asn Ser Glu Ile Glu Ser Leu Gln Lys Ala Leu Gly
        275                 280                 285 gta gct aga gaa gac aac agg aaa ctt gct atg agt ctg gaa caa gct      972
Val Ala Arg Glu Asp Asn Arg Lys Leu Ala Met Ser Leu Glu Gln Ala
    290                 295                 300 ctc cag aca aat aat cat ctg caa aca aag cta gat cac att caa gag     1020
Leu Gln Thr Asn Asn His Leu Gln Thr Lys Leu Asp His Ile Gln Glu
305                 310                 315                 320 caa ttg gaa agc aaa gaa ctt gag cga cag aat ttg gaa acc ttc aaa     1068
Gln Leu Glu Ser Lys Glu Leu Glu Arg Gln Asn Leu Glu Thr Phe Lys
            325                 330                 335 gac cgg atg act gaa gag tcc aaa gtg gaa gca gaa ttg cat gct gaa     1116
Asp Arg Met Thr Glu Glu Ser Lys Val Glu Ala Glu Leu His Ala Glu
        340                 345                 350 cgc ata gaa gct cta aga aag cag ttt caa acc gag aga gaa act aca     1164
Arg Ile Glu Ala Leu Arg Lys Gln Phe Gln Thr Glu Arg Glu Thr Thr
        355                 360                 365 aag aaa gtg gca caa cgg gaa gtg gct gag ctg aag aaa gcc ctt gat     1212
Lys Lys Val Ala Gln Arg Glu Val Ala Glu Leu Lys Lys Ala Leu Asp
    370                 375                 380 gaa gct aac ttc aga tca gtg gaa gtg tcc cgg acc aac cga gag ctg     1260
Glu Ala Asn Phe Arg Ser Val Glu Val Ser Arg Thr Asn Arg Glu Leu
385                 390                 395                 400 cga cag aaa ctt gca gag cta gaa aaa ata cta gaa agt aac aag gag     1308
Arg Gln Lys Leu Ala Glu Leu Glu Lys Ile Leu Glu Ser Asn Lys Glu
            405                 410                 415 aaa ata aag aat caa aag acc caa att aag ctc cac ttg tca gct aag     1356
Lys Ile Lys Asn Gln Lys Thr Gln Ile Lys Leu His Leu Ser Ala Lys
        420                 425                 430 gcg aat aat gct cag aat ata gaa agg atg aag gtt gta tgg gaa acc     1404
Ala Asn Asn Ala Gln Asn Ile Glu Arg Met Lys Val Val Trp Glu Thr
        435                 440                 445 tct tct cac ttc ctg gat acc ctg tgaggatgta gtcagtcaat ggtgtctagg    1458
Ser Ser His Phe Leu Asp Thr Leu
    450                 455 gaagacaggt tttagaaccc taccagcccc atgtattctc tgggaattat agccagttgt   1518
```

-continued

```
ctttggggag acttttttcag tggagtcact gctgtgtaaa tgtttgattt ctcatttgct    1578
gccagtgtca cattccggct ccctatctgt cccttccgtg ttgattgtac tggactttgc    1638
tcttttggga tcagtgggct agatgggaaa gaaagctcag caggaactgg taactttggg    1698
tctcatattg gattctttct gtcatcctat aggcaaaaag agcaagccag tttttccact    1758
gatcatcttt ttatgttatt ttccaattac ttttagcaaa tagaaaaaga attgaagcaa    1818
atggagctaa ttaaggatca atatcaaaaa aagaactatg aacagtcttt gagtatccag    1878
agatttgtgt gtgaaatgac taacctgcag aaagagatgc agatgttggc taagagccaa    1938
tatgatgcct cagtgcggaa taaacagcaa gagctgcacc tagaagcaga gcggaaaata    1998
aggcaggagc tagagaatcg gtgccaggaa ttggaagaaa ctgtcagaca cctgaagaaa    2058
tgtaaagagg caacagagaa tacgctgaaa gaagccagtg tggaatcaga acagataaca    2118
gctaatctgg aagaagctca tcgctggttt aagcacaggt ttgatggtct acaacttgag    2178
ctgacaaaaa accggttgca gaggccttct ggggaagaca ggtggcagga aaaggaccaa    2238
gatgtaaaac atgatgtcat gtccaaccaa tctgttctgc atcgatggga gagaaaacag    2298
aatcttaggc ccatgcccaa gaagtatcat tctgaggtac agaggaagtg atgtccttga    2358
caagggagct tctttatgtg tagctacact ccatgattcc aagagcccag cagccggggc    2418
tggcctgttt ctagagtcat aagaacatga agtctttgat gtgggctgaa gattttggac    2478
ctgagtttat cactttatga actcttatat cagtacaaaa ctacccctttt ttttgtccct    2538 tttcacattt tccacccaat aaatttgtgt taatttgttg tatgataaaa aaaaaaaa     2596
```

<210> SEQ ID NO 8
<211> LENGTH: 4714
<212> TYPE: DNA
<213> ORGANISM: Homo sapiens
<220> FEATURE:
<221> NAME/KEY: CDS
<222> LOCATION: (1)..(4143)
<223> OTHER INFORMATION:

<400> SEQUENCE: 8

```
atg ggc ata aaa cca gcc agc ttc aat aaa gtc act gat cct gaa gtc      48
Met Gly Ile Lys Pro Ala Ser Phe Asn Lys Val Thr Asp Pro Glu Val
1               5                   10                  15 aaa gaa atc att gaa gga tgt att cgt caa aac aaa tct gaa agg ttg      96
Lys Glu Ile Ile Glu Gly Cys Ile Arg Gln Asn Lys Ser Glu Arg Leu
            20                  25                  30 tct atc agg gac cta tta aac cat gca ttt ttt gct gag gat aca gga     144
Ser Ile Arg Asp Leu Leu Asn His Ala Phe Phe Ala Glu Asp Thr Gly
        35                  40                  45 ctg agg gtg gag tta gca gaa gaa gat gat tgc tca aat tca tcc ctt     192
Leu Arg Val Glu Leu Ala Glu Glu Asp Asp Cys Ser Asn Ser Ser Leu
    50                  55                  60 gct tta aga ctc tgg gtt gaa gac cct aaa aaa ttg aaa ggc aaa cac     240
Ala Leu Arg Leu Trp Val Glu Asp Pro Lys Lys Leu Lys Gly Lys His
65                  70                  75                  80 aaa gac aat gaa gct att gaa ttt agt ttc aac tta gaa aca gat aca     288
Lys Asp Asn Glu Ala Ile Glu Phe Ser Phe Asn Leu Glu Thr Asp Thr
                85                  90                  95 cct gag gaa gta gca tat gaa atg gtc aag tct ggg ttc ttc cat gaa     336
Pro Glu Glu Val Ala Tyr Glu Met Val Lys Ser Gly Phe Phe His Glu
            100                 105                 110 agt gat tcc aaa gct gtt gct aaa tcc att aga gac cgg gtg acg cca     384
Ser Asp Ser Lys Ala Val Ala Lys Ser Ile Arg Asp Arg Val Thr Pro
```

-continued

|     |     |     | 115 |     |     |     | 120 |     |     |     | 125 |     |     |     |      |
|-----|-----|-----|-----|-----|-----|-----|-----|-----|-----|-----|-----|-----|-----|-----|------|
| ata | aag | aag | aca | aga | gag | aag | aag | cct | gct | ggc | tgt | ttg | gaa | gaa cgc | 432 |
| Ile | Lys | Lys | Thr | Arg | Glu | Lys | Lys | Pro | Ala | Gly | Cys | Leu | Glu | Glu Arg |     |
|     | 130 |     |     |     |     | 135 |     |     |     | 140 |     |     |     |     |      |

| agg | gat | tct | cag | tgc | aag | tct | atg | ggg | aat | gta | ttc | cct | cag | ccc cag | 480 |
| Arg | Asp | Ser | Gln | Cys | Lys | Ser | Met | Gly | Asn | Val | Phe | Pro | Gln | Pro Gln |     |
| 145 |     |     |     |     | 150 |     |     |     |     | 155 |     |     |     | 160 |      |

| aat | aca | act | tta | ccc | ctt | gct | ccc | gct | cag | caa | act | ggg | gct | gaa tgt | 528 |
| Asn | Thr | Thr | Leu | Pro | Leu | Ala | Pro | Ala | Gln | Gln | Thr | Gly | Ala | Glu Cys |     |
|     |     |     |     | 165 |     |     |     |     | 170 |     |     |     |     | 175 |      |

| gaa | gaa | act | gaa | gtt | gat | caa | cat | gtt | aga | caa | cag | ctt | cta | caa aga | 576 |
| Glu | Glu | Thr | Glu | Val | Asp | Gln | His | Val | Arg | Gln | Gln | Leu | Leu | Gln Arg |     |
|     |     |     | 180 |     |     |     |     | 185 |     |     |     |     | 190 |     |      |

| aaa | cca | cag | cag | cac | tgc | tcc | tct | gtt | aca | ggt | gac | aat | ttg | tct gag | 624 |
| Lys | Pro | Gln | Gln | His | Cys | Ser | Ser | Val | Thr | Gly | Asp | Asn | Leu | Ser Glu |     |
|     |     | 195 |     |     |     |     | 200 |     |     |     |     | 205 |     |     |      |

| gca | gga | gct | gca | tca | gtt | ata | cat | tca | gat | act | tca | agt | cag | ccc agt | 672 |
| Ala | Gly | Ala | Ala | Ser | Val | Ile | His | Ser | Asp | Thr | Ser | Ser | Gln | Pro Ser |     |
|     | 210 |     |     |     |     | 215 |     |     |     |     | 220 |     |     |     |      |

| gta | gcc | tat | tcc | tca | aat | caa | acg | atg | ggc | tct | caa | atg | gtt | tct aat | 720 |
| Val | Ala | Tyr | Ser | Ser | Asn | Gln | Thr | Met | Gly | Ser | Gln | Met | Val | Ser Asn |     |
| 225 |     |     |     |     | 230 |     |     |     |     | 235 |     |     |     | 240 |      |

| atc | ccg | cag | gct | gaa | gta | aat | gtt | cca | ggg | caa | att | tat | tca | tct cag | 768 |
| Ile | Pro | Gln | Ala | Glu | Val | Asn | Val | Pro | Gly | Gln | Ile | Tyr | Ser | Ser Gln |     |
|     |     |     |     | 245 |     |     |     |     | 250 |     |     |     |     | 255 |      |

| caa | cta | gta | gga | cat | tac | cag | caa | gtt | tca | ggg | tta | cag | aag | cat tca | 816 |
| Gln | Leu | Val | Gly | His | Tyr | Gln | Gln | Val | Ser | Gly | Leu | Gln | Lys | His Ser |     |
|     |     |     | 260 |     |     |     |     | 265 |     |     |     |     | 270 |     |      |

| aag | ctg | act | cag | ccg | cag | att | ttg | cct | ttg | gtt | caa | ggt | cag | tcc act | 864 |
| Lys | Leu | Thr | Gln | Pro | Gln | Ile | Leu | Pro | Leu | Val | Gln | Gly | Gln | Ser Thr |     |
|     |     | 275 |     |     |     |     | 280 |     |     |     |     | 285 |     |     |      |

| gtt | tta | cct | gta | cat | gtc | ctt | gga | ccg | aca | gtt | gtt | tca | caa | ccc cag | 912 |
| Val | Leu | Pro | Val | His | Val | Leu | Gly | Pro | Thr | Val | Val | Ser | Gln | Pro Gln |     |
|     | 290 |     |     |     |     | 295 |     |     |     |     | 300 |     |     |     |      |

| gtt | tcc | cca | tta | act | gtt | cag | aag | gtc | cca | cag | ata | aag | cct | gta tcc | 960 |
| Val | Ser | Pro | Leu | Thr | Val | Gln | Lys | Val | Pro | Gln | Ile | Lys | Pro | Val Ser |     |
| 305 |     |     |     |     | 310 |     |     |     |     | 315 |     |     |     | 320 |      |

| caa | cca | gtt | gga | gct | gaa | caa | caa | gca | gct | ctt | cta | aaa | cca | gat tta | 1008 |
| Gln | Pro | Val | Gly | Ala | Glu | Gln | Gln | Ala | Ala | Leu | Leu | Lys | Pro | Asp Leu |     |
|     |     |     | 325 |     |     |     |     | 330 |     |     |     |     | 335 |     |      |

| gtt | cga | agc | ttg | aat | caa | gat | gtg | gca | act | acg | aag | gaa | aac | gtc agt | 1056 |
| Val | Arg | Ser | Leu | Asn | Gln | Asp | Val | Ala | Thr | Thr | Lys | Glu | Asn | Val Ser |     |
|     |     | 340 |     |     |     |     | 345 |     |     |     |     | 350 |     |     |      |

| agc | cct | gat | aac | cca | agt | gga | aat | ggc | aaa | cag | gat | cgg | atc | aaa cag | 1104 |
| Ser | Pro | Asp | Asn | Pro | Ser | Gly | Asn | Gly | Lys | Gln | Asp | Arg | Ile | Lys Gln |     |
|     | 355 |     |     |     |     | 360 |     |     |     |     | 365 |     |     |     |      |

| aga | aga | gct | tcc | tgt | ccc | cga | cca | gag | aag | ggg | act | aaa | ttt | cag ctt | 1152 |
| Arg | Arg | Ala | Ser | Cys | Pro | Arg | Pro | Glu | Lys | Gly | Thr | Lys | Phe | Gln Leu |     |
| 370 |     |     |     |     | 375 |     |     |     |     | 380 |     |     |     |     |      |

| acc | gtc | ctt | cag | gta | tca | acc | tct | gga | gat | aac | atg | gta | gag | tgt cag | 1200 |
| Thr | Val | Leu | Gln | Val | Ser | Thr | Ser | Gly | Asp | Asn | Met | Val | Glu | Cys Gln |     |
| 385 |     |     |     |     | 390 |     |     |     |     | 395 |     |     |     | 400 |      |

| ctg | gag | aca | cac | aac | aac | aag | atg | gtc | acc | ttc | aag | ttt | gat | gtt gat | 1248 |
| Leu | Glu | Thr | His | Asn | Asn | Lys | Met | Val | Thr | Phe | Lys | Phe | Asp | Val Asp |     |
|     |     |     |     | 405 |     |     |     |     | 410 |     |     |     |     | 415 |      |

| ggt | gat | gcg | cca | gag | gat | att | gca | gac | tat | atg | gtt | gaa | gat | aac ttt | 1296 |
| Gly | Asp | Ala | Pro | Glu | Asp | Ile | Ala | Asp | Tyr | Met | Val | Glu | Asp | Asn Phe |     |
|     | 420 |     |     |     |     | 425 |     |     |     |     | 430 |     |     |     |      |

| gtg | ctg | gaa | agt | gag | aaa | gaa | aaa | ttt | gta | gaa | gaa | ttg | aga | gct att | 1344 |

|  |  |  |  |  |  |  |  |  |  |  |  |  |
|---|---|---|---|---|---|---|---|---|---|---|---|---|
| Val | Leu | Glu | Ser | Glu | Lys | Glu | Lys | Phe | Val | Glu | Leu | Arg | Ala | Ile |
|  |  |  | 435 |  |  |  | 440 |  |  |  | 445 |  |  |  |

| gta | ggt | caa | gcc | cag | gag | atc | ctt | cat | gtc | cac | ttt | gcc | aca | gaa | aga | 1392 |
|---|---|---|---|---|---|---|---|---|---|---|---|---|---|---|---|---|
| Val | Gly | Gln | Ala | Gln | Glu | Ile | Leu | His | Val | His | Phe | Ala | Thr | Glu | Arg |  |
| 450 |  |  |  |  | 455 |  |  |  |  | 460 |  |  |  |  |  |  |

| gcc | act | gga | gtt | gat | tct | att | act | gtg | gac | tcc | aac | agt | agc | cag | aca | 1440 |
|---|---|---|---|---|---|---|---|---|---|---|---|---|---|---|---|---|
| Ala | Thr | Gly | Val | Asp | Ser | Ile | Thr | Val | Asp | Ser | Asn | Ser | Ser | Gln | Thr |  |
| 465 |  |  |  | 470 |  |  |  |  | 475 |  |  |  |  | 480 |  |  |

| ggg | tca | tct | gaa | caa | gta | cag | ata | aat | tct | aca | tct | act | caa | acc | agc | 1488 |
|---|---|---|---|---|---|---|---|---|---|---|---|---|---|---|---|---|
| Gly | Ser | Ser | Glu | Gln | Val | Gln | Ile | Asn | Ser | Thr | Ser | Thr | Gln | Thr | Ser |  |
|  |  |  |  | 485 |  |  |  |  | 490 |  |  |  |  | 495 |  |  |

| aat | gaa | tct | gct | cct | cag | tca | tcc | cca | gtt | ggt | cgg | tgg | cga | ttc | tgt | 1536 |
|---|---|---|---|---|---|---|---|---|---|---|---|---|---|---|---|---|
| Asn | Glu | Ser | Ala | Pro | Gln | Ser | Ser | Pro | Val | Gly | Arg | Trp | Arg | Phe | Cys |  |
|  |  |  | 500 |  |  |  |  | 505 |  |  |  |  | 510 |  |  |  |

| atc | aat | cag | acg | ata | aga | aac | cgt | gag | act | cag | tct | cct | cct | tct | ctt | 1584 |
|---|---|---|---|---|---|---|---|---|---|---|---|---|---|---|---|---|
| Ile | Asn | Gln | Thr | Ile | Arg | Asn | Arg | Glu | Thr | Gln | Ser | Pro | Pro | Ser | Leu |  |
|  |  | 515 |  |  |  |  | 520 |  |  |  |  | 525 |  |  |  |  |

| cag | cat | tcc | atg | tct | gcg | gtt | cct | ggc | cga | cat | cca | ctt | cct | agt | cca | 1632 |
|---|---|---|---|---|---|---|---|---|---|---|---|---|---|---|---|---|
| Gln | His | Ser | Met | Ser | Ala | Val | Pro | Gly | Arg | His | Pro | Leu | Pro | Ser | Pro |  |
|  | 530 |  |  |  |  | 535 |  |  |  |  | 540 |  |  |  |  |  |

| aaa | aac | aca | agt | aat | aag | gaa | ata | tca | cgg | gac | aca | ttg | ctc | act | ata | 1680 |
|---|---|---|---|---|---|---|---|---|---|---|---|---|---|---|---|---|
| Lys | Asn | Thr | Ser | Asn | Lys | Glu | Ile | Ser | Arg | Asp | Thr | Leu | Leu | Thr | Ile |  |
| 545 |  |  |  | 550 |  |  |  |  | 555 |  |  |  |  | 560 |  |  |

| gaa | aat | aat | cca | tgc | cac | cgt | gca | ctt | ttc | acc | tcc | aaa | tca | gaa | cac | 1728 |
|---|---|---|---|---|---|---|---|---|---|---|---|---|---|---|---|---|
| Glu | Asn | Asn | Pro | Cys | His | Arg | Ala | Leu | Phe | Thr | Ser | Lys | Ser | Glu | His |  |
|  |  |  | 565 |  |  |  |  | 570 |  |  |  |  | 575 |  |  |  |

| aag | gat | gtg | gtt | gat | ggt | aag | att | tct | gaa | tgt | gct | agt | gta | gaa | acc | 1776 |
|---|---|---|---|---|---|---|---|---|---|---|---|---|---|---|---|---|
| Lys | Asp | Val | Val | Asp | Gly | Lys | Ile | Ser | Glu | Cys | Ala | Ser | Val | Glu | Thr |  |
|  |  |  | 580 |  |  |  |  | 585 |  |  |  |  | 590 |  |  |  |

| aag | cag | cca | gct | ata | ctt | tat | caa | gtg | gaa | gat | aac | agg | cag | ata | atg | 1824 |
|---|---|---|---|---|---|---|---|---|---|---|---|---|---|---|---|---|
| Lys | Gln | Pro | Ala | Ile | Leu | Tyr | Gln | Val | Glu | Asp | Asn | Arg | Gln | Ile | Met |  |
|  |  | 595 |  |  |  |  | 600 |  |  |  |  | 605 |  |  |  |  |

| gca | cca | gtt | act | aat | agt | tcc | agt | tac | tct | act | act | tca | gtt | cgt | gca | 1872 |
|---|---|---|---|---|---|---|---|---|---|---|---|---|---|---|---|---|
| Ala | Pro | Val | Thr | Asn | Ser | Ser | Ser | Tyr | Ser | Thr | Thr | Ser | Val | Arg | Ala |  |
|  | 610 |  |  |  |  | 615 |  |  |  |  | 620 |  |  |  |  |  |

| gtt | cca | gct | gaa | tgt | gag | gga | ctc | acc | aaa | caa | gca | agc | ata | ttc | ata | 1920 |
|---|---|---|---|---|---|---|---|---|---|---|---|---|---|---|---|---|
| Val | Pro | Ala | Glu | Cys | Glu | Gly | Leu | Thr | Lys | Gln | Ala | Ser | Ile | Phe | Ile |  |
| 625 |  |  |  |  | 630 |  |  |  |  | 635 |  |  |  |  | 640 |  |

| cct | gtg | tat | cca | tgt | cac | caa | act | gcc | agt | cag | gct | gat | gca | ctt | atg | 1968 |
|---|---|---|---|---|---|---|---|---|---|---|---|---|---|---|---|---|
| Pro | Val | Tyr | Pro | Cys | His | Gln | Thr | Ala | Ser | Gln | Ala | Asp | Ala | Leu | Met |  |
|  |  |  | 645 |  |  |  |  | 650 |  |  |  |  | 655 |  |  |  |

| tcc | cat | cct | ggc | gaa | tca | act | cag | act | tct | ggt | aac | tct | ctt | aca | act | 2016 |
|---|---|---|---|---|---|---|---|---|---|---|---|---|---|---|---|---|
| Ser | His | Pro | Gly | Glu | Ser | Thr | Gln | Thr | Ser | Gly | Asn | Ser | Leu | Thr | Thr |  |
|  |  | 660 |  |  |  |  | 665 |  |  |  |  | 670 |  |  |  |  |

| ctg | gca | ttt | gat | caa | aag | cct | caa | acc | tta | tca | gta | cag | cag | cca | gct | 2064 |
|---|---|---|---|---|---|---|---|---|---|---|---|---|---|---|---|---|
| Leu | Ala | Phe | Asp | Gln | Lys | Pro | Gln | Thr | Leu | Ser | Val | Gln | Gln | Pro | Ala |  |
|  |  | 675 |  |  |  |  | 680 |  |  |  |  | 685 |  |  |  |  |

| atg | gat | gca | gag | ttt | att | tct | caa | gaa | gga | gaa | act | aca | gtg | aac | act | 2112 |
|---|---|---|---|---|---|---|---|---|---|---|---|---|---|---|---|---|
| Met | Asp | Ala | Glu | Phe | Ile | Ser | Gln | Glu | Gly | Glu | Thr | Thr | Val | Asn | Thr |  |
| 690 |  |  |  |  | 695 |  |  |  |  | 700 |  |  |  |  |  |  |

| gaa | gca | agt | tct | cct | aag | aca | gtc | att | ccc | act | cag | acc | cct | ggc | ctt | 2160 |
|---|---|---|---|---|---|---|---|---|---|---|---|---|---|---|---|---|
| Glu | Ala | Ser | Ser | Pro | Lys | Thr | Val | Ile | Pro | Thr | Gln | Thr | Pro | Gly | Leu |  |
| 705 |  |  |  | 710 |  |  |  |  | 715 |  |  |  |  | 720 |  |  |

| gaa | cca | act | acc | ctt | caa | ccc | act | act | gtc | ctg | gaa | tca | gat | gga | gaa | 2208 |
|---|---|---|---|---|---|---|---|---|---|---|---|---|---|---|---|---|
| Glu | Pro | Thr | Thr | Leu | Gln | Pro | Thr | Thr | Val | Leu | Glu | Ser | Asp | Gly | Glu |  |
|  |  |  | 725 |  |  |  |  | 730 |  |  |  |  | 735 |  |  |  |

| aga | cct | cca | aaa | ctg | gag | ttt | gca | gac | aac | cga | att | aaa | act | ctg | gat | 2256 |
|---|---|---|---|---|---|---|---|---|---|---|---|---|---|---|---|---|
| Arg | Pro | Pro | Lys | Leu | Glu | Phe | Ala | Asp | Asn | Arg | Ile | Lys | Thr | Leu | Asp |  |
|  |  | 740 |  |  |  |  | 745 |  |  |  |  | 750 |  |  |  |  |

-continued

```
gaa aaa tta aga aac ttg ctc tat cag gag cac agc atc tct agc atc        2304
Glu Lys Leu Arg Asn Leu Leu Tyr Gln Glu His Ser Ile Ser Ser Ile
        755                 760                 765 tat ccc gag agt cag aag gat acc caa agc ata gac tct cca ttt tct        2352
Tyr Pro Glu Ser Gln Lys Asp Thr Gln Ser Ile Asp Ser Pro Phe Ser
770                 775                 780 tcc tct gct gaa gat acc ctc tcc tgt cca gtg aca gaa gtc ata gcc        2400
Ser Ser Ala Glu Asp Thr Leu Ser Cys Pro Val Thr Glu Val Ile Ala
785                 790                 795                 800 atc agt cac tgt gga att aaa gat agc cct gta caa tcc cct aat ttc        2448
Ile Ser His Cys Gly Ile Lys Asp Ser Pro Val Gln Ser Pro Asn Phe
                805                 810                 815 caa cag aca ggc tct aag ctt ctg tcc aat gtg gct gca agt cag cct        2496
Gln Gln Thr Gly Ser Lys Leu Leu Ser Asn Val Ala Ala Ser Gln Pro
        820                 825                 830 gct aat ata tca gtg ttc aaa agg gac ctg aat gtg ata act tct gta        2544
Ala Asn Ile Ser Val Phe Lys Arg Asp Leu Asn Val Ile Thr Ser Val
            835                 840                 845 tcc agc gaa ttg tgt tta cat gag atg tcc tca gat gct tca ctt cca        2592
Ser Ser Glu Leu Cys Leu His Glu Met Ser Ser Asp Ala Ser Leu Pro
850                 855                 860 ggg gat cca gag gcc tat cct gct gct gtg tca agc ggt gga gcc att        2640
Gly Asp Pro Glu Ala Tyr Pro Ala Ala Val Ser Ser Gly Gly Ala Ile
865                 870                 875                 880 cat ctg cag aca gga gtg gaa aca gaa gag atg aga tca gca att gct        2688
His Leu Gln Thr Gly Val Glu Thr Glu Glu Met Arg Ser Ala Ile Ala
                885                 890                 895 cct gat ccc att cct ctg aca cgg gag tcc aca gct gat act agg gct        2736
Pro Asp Pro Ile Pro Leu Thr Arg Glu Ser Thr Ala Asp Thr Arg Ala
        900                 905                 910 ttg aat aga tgt aaa gcg atg agt gga tca ttt cag cgg ggt cgg ttc        2784
Leu Asn Arg Cys Lys Ala Met Ser Gly Ser Phe Gln Arg Gly Arg Phe
            915                 920                 925 cag gtg att aca att cct cag cag cag tca gca aaa atg aca tct ttt        2832
Gln Val Ile Thr Ile Pro Gln Gln Gln Ser Ala Lys Met Thr Ser Phe
930                 935                 940 gga ata gaa cac ata tca gtg ttc agt gag aca aac cat tct agt gaa        2880
Gly Ile Glu His Ile Ser Val Phe Ser Glu Thr Asn His Ser Ser Glu
945                 950                 955                 960 gaa gcc ttt att aaa aca gca aag tct cag ttg gta gaa ata gaa cct        2928
Glu Ala Phe Ile Lys Thr Ala Lys Ser Gln Leu Val Glu Ile Glu Pro
                965                 970                 975 gcc aca caa aat cca aaa act tcg ttt tct tat gag aag tta caa gct        2976
Ala Thr Gln Asn Pro Lys Thr Ser Phe Ser Tyr Glu Lys Leu Gln Ala
        980                 985                 990 ctt cag gaa acc tgt aaa gaa aat aaa gga gtt ccc aaa caa ggt gac        3024
Leu Gln Glu Thr Cys Lys Glu Asn Lys Gly Val Pro Lys Gln Gly Asp
            995                 1000                1005 aac ttc tta tct ttc agc gca gct tgt gag act gat gta tct tca        3069
Asn Phe Leu Ser Phe Ser Ala Ala Cys Glu Thr Asp Val Ser Ser
    1010                1015                1020 gtg acc cca gaa aag gaa ttt gaa gaa act tca gcc aca gga agt        3114
Val Thr Pro Glu Lys Glu Phe Glu Glu Thr Ser Ala Thr Gly Ser
    1025                1030                1035 agc atg cag tct gga tct gaa ctg ttg ctt aaa gag aga gag ata        3159
Ser Met Gln Ser Gly Ser Glu Leu Leu Leu Lys Glu Arg Glu Ile
    1040                1045                1050 ttg act gct ggg aaa cag cct agc tct gat agt gaa ttt tca gcc        3204
Leu Thr Ala Gly Lys Gln Pro Ser Ser Asp Ser Glu Phe Ser Ala
    1055                1060                1065
```

```
agt ctt gct ggc agt gga aag tca gtg gca aag act ggt cca gag     3249
Ser Leu Ala Gly Ser Gly Lys Ser Val Ala Lys Thr Gly Pro Glu
    1070                1075                1080 agt aat cag tgc tta cca cac cac gaa gaa caa gct tat gct caa     3294
Ser Asn Gln Cys Leu Pro His His Glu Glu Gln Ala Tyr Ala Gln
    1085                1090                1095 aca cag agt tca ctc ttc tat tcg cca tct tcc cca atg agc agt     3339
Thr Gln Ser Ser Leu Phe Tyr Ser Pro Ser Ser Pro Met Ser Ser
    1100                1105                1110 gat gat gaa tca gaa ata gag gat gag gac ttg aag gtg gag ctt     3384
Asp Asp Glu Ser Glu Ile Glu Asp Glu Asp Leu Lys Val Glu Leu
    1115                1120                1125 caa aga tta cga gaa aaa cac att cag gag gtg gta aat ctt caa     3429
Gln Arg Leu Arg Glu Lys His Ile Gln Glu Val Val Asn Leu Gln
    1130                1135                1140 acc cag cag aat aag gag ctg cag gag ctc tat gaa cgc ctt cgg     3474
Thr Gln Gln Asn Lys Glu Leu Gln Glu Leu Tyr Glu Arg Leu Arg
    1145                1150                1155 tca att aaa gat agc aaa acc caa tct act gag att cct ttg cca     3519
Ser Ile Lys Asp Ser Lys Thr Gln Ser Thr Glu Ile Pro Leu Pro
    1160                1165                1170 cct gca tca cca cgt cga cca aga tct ttc aaa agc aaa ctt cga     3564
Pro Ala Ser Pro Arg Arg Pro Arg Ser Phe Lys Ser Lys Leu Arg
    1175                1180                1185 agc cgc ccc cag tcc ttg aca cat gtg gac aat ggc ata gtt gct     3609
Ser Arg Pro Gln Ser Leu Thr His Val Asp Asn Gly Ile Val Ala
    1190                1195                1200 aca gat cca ctg tgt gtg gag agt aat gca gca tca tgc caa cag     3654
Thr Asp Pro Leu Cys Val Glu Ser Asn Ala Ala Ser Cys Gln Gln
    1205                1210                1215 tct cca gcc agt aaa aaa ggg atg ttc aca gat gac tta cac aag     3699
Ser Pro Ala Ser Lys Lys Gly Met Phe Thr Asp Asp Leu His Lys
    1220                1225                1230 ctg gtg gat gac tgg aca aag gaa gca gta gga aat tct ctt att     3744
Leu Val Asp Asp Trp Thr Lys Glu Ala Val Gly Asn Ser Leu Ile
    1235                1240                1245 aag cca agt tta aac caa ctt aaa caa agt caa cac aaa cta gag     3789
Lys Pro Ser Leu Asn Gln Leu Lys Gln Ser Gln His Lys Leu Glu
    1250                1255                1260 aca gaa aac tgg aat aaa gta tct gaa aat act ccg tct act atg     3834
Thr Glu Asn Trp Asn Lys Val Ser Glu Asn Thr Pro Ser Thr Met
    1265                1270                1275 ggc tac aca tca aca tgg att tct tct ctg tcc caa atc cgt gga     3879
Gly Tyr Thr Ser Thr Trp Ile Ser Ser Leu Ser Gln Ile Arg Gly
    1280                1285                1290 gct gtc cca act tcc ttg cca caa gga ctc tca ctc cct tca ttt     3924
Ala Val Pro Thr Ser Leu Pro Gln Gly Leu Ser Leu Pro Ser Phe
    1295                1300                1305 cct ggg cca tta tca tca tat gga atg cct cac gtt tgt cag tat     3969
Pro Gly Pro Leu Ser Ser Tyr Gly Met Pro His Val Cys Gln Tyr
    1310                1315                1320 aat gct gtg gcg ggg gcg ggg tat cca gta cag tgg gta gga att     4014
Asn Ala Val Ala Gly Ala Gly Tyr Pro Val Gln Trp Val Gly Ile
    1325                1330                1335 tca gga aca aca caa caa tct gta gta att ccc gcc caa tct ggg     4059
Ser Gly Thr Thr Gln Gln Ser Val Val Ile Pro Ala Gln Ser Gly
    1340                1345                1350 gga cca ttc cag cca ggg atg aat atg cag gca ttt cca act tca     4104
Gly Pro Phe Gln Pro Gly Met Asn Met Gln Ala Phe Pro Thr Ser
```

| | | | |
|---|---|---|---|
| 1355 | | 1360 | 1365 | tca gtg cag aat cct gcc aca atc cct cct ggt cct aaa tgaatcagag    4153
Ser Val Gln Asn Pro Ala Thr Ile Pro Pro Gly Pro Lys
    1370                1375            1380 tagatggtga taaaaaggga ggttttttca gaattatttt caggacaccc aagatattaa    4213
agtttcttcc tcttgggttc tgtcatattt tccctcattt gagtttactt tagactatat    4273 atttttttgtt ccagtgtggt atttgataca gctcatcatt ctgtagaaat gtgcagtttg    4333
cagatagaac actgcacaca gaaatgtttt ttcacttcaa attctatcct ctttgatact    4393 tgattttttta aaaatactgt tcagaatgct ttaataagct cagcttgagc attaccattt    4453
ccaggacact ttccatgaat tgttgagaag ctccccatcc cccgcctttt ttttttttt    4513 tttaactgct gctatctgca gctggatact cttcttaaa aatgtttaaa aattatttag    4573
attgattctc cccaaatgtg gatgaactga gaccctccat cagccagagt cttatgggat    4633
cttcacttca catgtttgtc ttaggtttac ctttcacaga aggcagggta acttgctgca    4693
ggaaacgttt tggtgtataa a    4714

<210> SEQ ID NO 9
<211> LENGTH: 1567
<212> TYPE: DNA
<213> ORGANISM: Homo sapiens
<220> FEATURE:
<221> NAME/KEY: CDS
<222> LOCATION: (375)..(1034)
<223> OTHER INFORMATION:
<220> FEATURE:
<221> NAME/KEY: misc_feature
<222> LOCATION: (1)..(1567)
<223> OTHER INFORMATION: n = a, t, c, or g

<400> SEQUENCE: 9
atagatcatt ttctgtaaca ggtgacaaaa gcagaaaaga atgaagaggc tgaagtatga     60
actacccttg gagcccatat acatgatata ggcaatttct tttgtatgtt aattcagtca    120 aaatactac ccacttgatg ttttctaatc tgatgtgagc tcatgttaca cagactttta    180
gtaagtaacc cgtgactaga aaataaactg gatgcttagg agagagtgtc agatgtataa    240
gatgctaata aaacctgttt aatattattg ttagctgtaa gttttttgggc tgctctgttc    300 ataagggctt tgccttcgtt cagtatgtta atgagagaaa tgcccgggct gctgtagcag    360
gagaggatgg caga atg att gct ggc cag gtt tta gat att aac ctg gct    410
              Met Ile Ala Gly Gln Val Leu Asp Ile Asn Leu Ala
                1               5                   10 gca gag cca aaa gtg aac cga gga aaa gca ggt gtg aaa cga tct gca    458
Ala Glu Pro Lys Val Asn Arg Gly Lys Ala Gly Val Lys Arg Ser Ala
        15                  20                  25 gcg gag atg tac ggc tcc tct ttt gac ttg gac tat gac ttt caa cgg    506
Ala Glu Met Tyr Gly Ser Ser Phe Asp Leu Asp Tyr Asp Phe Gln Arg
    30                  35                  40 gac tat tat gat agg atg tac agt tac cca gca cgt gta cct cct cct    554
Asp Tyr Tyr Asp Arg Met Tyr Ser Tyr Pro Ala Arg Val Pro Pro Pro
45                  50                  55                  60 cct cct att gct cgg gct gta gtg ccc tcg aaa cgt cag cgt gta tca    602
Pro Pro Ile Ala Arg Ala Val Val Pro Ser Lys Arg Gln Arg Val Ser
                65                  70                  75 gga aac act tca cga agg ggc aaa agt ggc ttc aat tct aag agt gga    650
Gly Asn Thr Ser Arg Arg Gly Lys Ser Gly Phe Asn Ser Lys Ser Gly
            80                  85                  90 cag cgg gga tct tcc aag tct gga aag ttg aaa gga gat gac ctt cag    698

```
Gln Arg Gly Ser Ser Lys Ser Gly Lys Leu Lys Gly Asp Asp Leu Gln
         95                 100                 105 gcc att aag aag gag ctg acc cag ata aaa caa aaa gtg gat tct ctc      746
Ala Ile Lys Lys Glu Leu Thr Gln Ile Lys Gln Lys Val Asp Ser Leu
    110                 115                 120 ctg gaa aac ctg gaa aaa att gaa aag gaa cag agc aaa caa gca gta      794
Leu Glu Asn Leu Glu Lys Ile Glu Lys Glu Gln Ser Lys Gln Ala Val
125                 130                 135                 140 gag atg aag aat gat aag tca gaa gag gag cag agc agc agc tcc gtg      842
Glu Met Lys Asn Asp Lys Ser Glu Glu Glu Gln Ser Ser Ser Ser Val
                145                 150                 155 aag aaa gat gag act aat gtg aag atg gag tct gag ggg ggt gca gat      890
Lys Lys Asp Glu Thr Asn Val Lys Met Glu Ser Glu Gly Gly Ala Asp
            160                 165                 170 gac tct gct gag gag ggg gac cta ctg gat gat gat gat aat gaa gat      938
Asp Ser Ala Glu Glu Gly Asp Leu Leu Asp Asp Asp Asp Asn Glu Asp
        175                 180                 185 cgg ggg gat gac cag ctg gag ttg atc aag gat gat gaa aaa gag gct      986
Arg Gly Asp Asp Gln Leu Glu Leu Ile Lys Asp Asp Glu Lys Glu Ala
    190                 195                 200 gag gaa gga gag gat gac aga gac agc gcc aat ggc gag gat gac tct     1034
Glu Glu Gly Glu Asp Asp Arg Asp Ser Ala Asn Gly Glu Asp Asp Ser
205                 210                 215                 220 taagcacata gtgggtttta gaaatcttat cccattattt ctttacctag gcgcttgtct    1094
aagatcaaat ttttcaccag atcctctccc ctagtatctt cagcacatgc tcactgttct    1154
ccccatcctt gtccttccca tgttcattaa ttcatattgc cccgcgccta gtcccatttt    1214
cacttccttt gacgctccta gtagttttgt taagtcttac cctgtaattt ttgcttttaa    1274
ttttgatacc tctttatgac ttaacaataa aaaggatgta tggtttttat caactgtctc    1334
caaaaataat ctcttggtat gcagggagta ccagttctct tcattcatac ataagttcag    1394
tagtggcttc cttaactgca nagggcatct cantttagtg agtagctctt gggaagcagc    1454
tttgagtaga angtatgtgt gtacaccctt acattagtgt gctgtgtggg gcagtcaaca    1514
canatggtac atgtattntg tgatgagagt ggcatgtcaa tgcatctcta gaa           1567
```

<210> SEQ ID NO 10
<211> LENGTH: 3260
<212> TYPE: DNA
<213> ORGANISM: Homo sapiens
<220> FEATURE:
<221> NAME/KEY: CDS
<222> LOCATION: (87)..(2315)
<223> OTHER INFORMATION:

<400> SEQUENCE: 10

```
tgctggagca gctgctccca gagctcaccg ggctgctcag cctcctggac cacgagtacc     60
tcagcgatac caccctggaa aagaag atg gcc gtg gcc tcc atc ctg cag agc    113
                              Met Ala Val Ala Ser Ile Leu Gln Ser
                                1               5 ctg cag ccc ctt cca gct ggc atg tcc ccc ttc ttc ctc aca gca aag      161
Leu Gln Pro Leu Pro Ala Gly Met Ser Pro Phe Phe Leu Thr Ala Lys
 10                  15                  20                  25 gag gtc tcc tac ctg tat gtg aac aca gca gac ctc cac tcg ggg ccc      209
Glu Val Ser Tyr Leu Tyr Val Asn Thr Ala Asp Leu His Ser Gly Pro
                 30                  35                  40 agc ttc gtg gaa tcc ctc ttt gaa gaa ttt gac tgt gac ctg agt gac      257
Ser Phe Val Glu Ser Leu Phe Glu Glu Phe Asp Cys Asp Leu Ser Asp
             45                  50                  55
```

```
ctt cgg gac atg cca gag gat gat ggg gag ccc agc aaa gga gcc agc     305
Leu Arg Asp Met Pro Glu Asp Asp Gly Glu Pro Ser Lys Gly Ala Ser
         60                  65                  70 cct gag cta gcc aag agc cca cgc ctg aga aac gcg gcc gac ctg cct     353
Pro Glu Leu Ala Lys Ser Pro Arg Leu Arg Asn Ala Ala Asp Leu Pro
 75                  80                  85 cca ccg ctc ccc aac aag cct ccc cct gag gac tac tat gaa gag gcc     401
Pro Pro Leu Pro Asn Lys Pro Pro Pro Glu Asp Tyr Tyr Glu Glu Ala
 90                  95                 100                 105 ctt cct ctg gga ccc ggc aag tcg cct gag tac atc agc tcc cac aat     449
Leu Pro Leu Gly Pro Gly Lys Ser Pro Glu Tyr Ile Ser Ser His Asn
             110                 115                 120 ggc tgc agc ccc tca cac tcg att gtg gat ggc tac tat gag gac gca     497
Gly Cys Ser Pro Ser His Ser Ile Val Asp Gly Tyr Tyr Glu Asp Ala
             125                 130                 135 gac agc agc tac cct gca acc agg gtg aac ggc gag ctt aag agc tcc     545
Asp Ser Ser Tyr Pro Ala Thr Arg Val Asn Gly Glu Leu Lys Ser Ser
             140                 145                 150 tat aat gac tct gac gca atg agc agc tcc tat gag tcc tac gat gaa     593
Tyr Asn Asp Ser Asp Ala Met Ser Ser Ser Tyr Glu Ser Tyr Asp Glu
         155                 160                 165 gag gag gag gaa ggg aag agc ccg cag ccc cga cac cag tgg ccc tca     641
Glu Glu Glu Glu Gly Lys Ser Pro Gln Pro Arg His Gln Trp Pro Ser
170                 175                 180                 185 gag gag gcc tcc atg cac ctg gtg agg gaa tgc agg ata tgt gcc ttc     689
Glu Glu Ala Ser Met His Leu Val Arg Glu Cys Arg Ile Cys Ala Phe
                 190                 195                 200 ctg ctg cgg aaa aag cgt ttc ggg cag tgg gcc aag cag ctg acg gtc     737
Leu Leu Arg Lys Lys Arg Phe Gly Gln Trp Ala Lys Gln Leu Thr Val
             205                 210                 215 atc agg gag gac cag ctc ctg tgt tac aaa agc tcc aag gat cgg cag     785
Ile Arg Glu Asp Gln Leu Leu Cys Tyr Lys Ser Ser Lys Asp Arg Gln
         220                 225                 230 cca cat ctg agg ttg gca ctg gat acc tgc agc atc atc tac gtg ccc     833
Pro His Leu Arg Leu Ala Leu Asp Thr Cys Ser Ile Ile Tyr Val Pro
     235                 240                 245 aag gac agc cgg cac aag agg cac gag ctg cgt ttc acc cag ggg gct     881
Lys Asp Ser Arg His Lys Arg His Glu Leu Arg Phe Thr Gln Gly Ala
250                 255                 260                 265 acc gag gtc ttg gtg ctg gca ctg cag agc cga gag cag gcc gag gag     929
Thr Glu Val Leu Val Leu Ala Leu Gln Ser Arg Glu Gln Ala Glu Glu
                 270                 275                 280 tgg ctg aag gtc atc cga gaa gtg agc aag cca gtt ggg gga gct gag     977
Trp Leu Lys Val Ile Arg Glu Val Ser Lys Pro Val Gly Gly Ala Glu
             285                 290                 295 gga gtg gag gtc ccc aga tcc cca gtc ctc ctg tgc aag ttg gac ctg    1025
Gly Val Glu Val Pro Arg Ser Pro Val Leu Leu Cys Lys Leu Asp Leu
         300                 305                 310 gac aag agg ctg tcc caa gag aag cag acc tca gat tct gac agc gtg    1073
Asp Lys Arg Leu Ser Gln Glu Lys Gln Thr Ser Asp Ser Asp Ser Val
     315                 320                 325 ggt gtg ggt gac aac tgt tct acc ctt ggc cgc cgg gag acc tgt gat    1121
Gly Val Gly Asp Asn Cys Ser Thr Leu Gly Arg Arg Glu Thr Cys Asp
330                 335                 340                 345 cac ggc aaa ggg aag aag agc agc ctg gca gaa ctg aag ggc tca atg    1169
His Gly Lys Gly Lys Lys Ser Ser Leu Ala Glu Leu Lys Gly Ser Met
                 350                 355                 360 agc agg gct gcg ggc cgc aag atc acc cgt atc att ggc ttc tcc aag    1217
Ser Arg Ala Ala Gly Arg Lys Ile Thr Arg Ile Ile Gly Phe Ser Lys
             365                 370                 375
```

```
aag aag aca ctg gcc gat gac ctg cag acg tcc tcc acc gag gag gag     1265
Lys Lys Thr Leu Ala Asp Asp Leu Gln Thr Ser Ser Thr Glu Glu Glu
        380                 385                 390 gtt ccc tgc tgt ggc tac ctg aac gtg ctg gtg aac cag ggc tgg aag     1313
Val Pro Cys Cys Gly Tyr Leu Asn Val Leu Val Asn Gln Gly Trp Lys
        395                 400                 405 gaa cgc tgg tgc cgc ctg aag tgc aac act ctg tat ttc cac aag gat     1361
Glu Arg Trp Cys Arg Leu Lys Cys Asn Thr Leu Tyr Phe His Lys Asp
410                 415                 420                 425 cac atg gac ctg cga acc cat gtg aac gcc atc gcc ctg caa ggc tgt     1409
His Met Asp Leu Arg Thr His Val Asn Ala Ile Ala Leu Gln Gly Cys
                430                 435                 440 gag gtg gcc ccg ggc ttt ggg ccc cga cac cca ttt gcc ttc agg atc     1457
Glu Val Ala Pro Gly Phe Gly Pro Arg His Pro Phe Ala Phe Arg Ile
                445                 450                 455 ctg cgc aac cgg cag gag gtg gcc atc ttg gag gca agc tgt tca gag     1505
Leu Arg Asn Arg Gln Glu Val Ala Ile Leu Glu Ala Ser Cys Ser Glu
                460                 465                 470 gac atg ggt cgc tgg ctc ggg ctg ctg ctg gtg gag atg ggc tcc aga     1553
Asp Met Gly Arg Trp Leu Gly Leu Leu Leu Val Glu Met Gly Ser Arg
        475                 480                 485 gtc act ccg gag gcg ctg cac tat gac tac gtg gat gtg gag acc tta     1601
Val Thr Pro Glu Ala Leu His Tyr Asp Tyr Val Asp Val Glu Thr Leu
490                 495                 500                 505 acc agc atc gtc agt gct ggg cgc aac tcc ttc cta tat gca aga tcc     1649
Thr Ser Ile Val Ser Ala Gly Arg Asn Ser Phe Leu Tyr Ala Arg Ser
                510                 515                 520 tgc cag aat cag tgg cct gag ccc cga gtc tat gat gat gtt cct tat     1697
Cys Gln Asn Gln Trp Pro Glu Pro Arg Val Tyr Asp Asp Val Pro Tyr
                525                 530                 535 gaa aag atg cag gac gag gag ccc gag cgc ccc aca ggg gcc cag gtg     1745
Glu Lys Met Gln Asp Glu Glu Pro Glu Arg Pro Thr Gly Ala Gln Val
                540                 545                 550 aag cgt cac gcc tcc tcc tgc agt gag aag tcc cat cgt gtg gac ccg     1793
Lys Arg His Ala Ser Ser Cys Ser Glu Lys Ser His Arg Val Asp Pro
        555                 560                 565 cag gtc aaa gtc aaa cgc cac gcc tcc agt gcc aat caa tac aag tat     1841
Gln Val Lys Val Lys Arg His Ala Ser Ser Ala Asn Gln Tyr Lys Tyr
570                 575                 580                 585 ggc aag aac cga gcc gag gag gat gcc cgg agg tac ttg gta gaa aaa     1889
Gly Lys Asn Arg Ala Glu Glu Asp Ala Arg Arg Tyr Leu Val Glu Lys
                590                 595                 600 gag aag ctg gag aaa gag aaa gag acg att cgg aca gag ctg ata gca     1937
Glu Lys Leu Glu Lys Glu Lys Glu Thr Ile Arg Thr Glu Leu Ile Ala
                605                 610                 615 ctg aga cag gag aag agg gaa ctg aag gaa gcc att cgg agc agc cca     1985
Leu Arg Gln Glu Lys Arg Glu Leu Lys Glu Ala Ile Arg Ser Ser Pro
        620                 625                 630 gga gca aaa tta aag gct ctg gaa gaa gcc gtg gcc acc ctg gaa gct     2033
Gly Ala Lys Leu Lys Ala Leu Glu Glu Ala Val Ala Thr Leu Glu Ala
        635                 640                 645 cag tgt cgg gca aag gag gag cgc cgg att gac ctg gag ctg aag ctg     2081
Gln Cys Arg Ala Lys Glu Glu Arg Arg Ile Asp Leu Glu Leu Lys Leu
650                 655                 660                 665 gtg gct gtg aag gag cgc ttg cag cag tcc ctg gca gga ggg cca gcc     2129
Val Ala Val Lys Glu Arg Leu Gln Gln Ser Leu Ala Gly Gly Pro Ala
                670                 675                 680 ctg ggg ctc tcc gtg agc agc aag ccc aag agt ggg gaa act gca aat     2177
Leu Gly Leu Ser Val Ser Ser Lys Pro Lys Ser Gly Glu Thr Ala Asn
```

-continued

| | | | 685 | | | | 690 | | | | 695 | | | |
|---|---|---|---|---|---|---|---|---|---|---|---|---|---|---|
| aaa | ccc | cag | aac | agc | gtt | cca | gag | caa | cct | ctc | cct | gtc | aac | tgt gtc | 2225 |
| Lys | Pro | Gln | Asn | Ser | Val | Pro | Glu | Gln | Pro | Leu | Pro | Val | Asn | Cys Val | |
| | | | 700 | | | | 705 | | | | 710 | | | | |

| tct | gag | ctg | agg | aag | agg | agc | cca | tcc | atc | gta | gcc | tcc | aac | caa gga | 2273 |
|---|---|---|---|---|---|---|---|---|---|---|---|---|---|---|---|
| Ser | Glu | Leu | Arg | Lys | Arg | Ser | Pro | Ser | Ile | Val | Ala | Ser | Asn | Gln Gly | |
| | 715 | | | | 720 | | | | 725 | | | | | | |

| agg | gtg | cta | cag | aaa | gcc | aag | gaa | tgg | gaa | atg | aag | aag | acc | | 2315 |
|---|---|---|---|---|---|---|---|---|---|---|---|---|---|---|---|
| Arg | Val | Leu | Gln | Lys | Ala | Lys | Glu | Trp | Glu | Met | Lys | Lys | Thr | | |
| 730 | | | | 735 | | | | 740 | | | | | | | |

| taggaagagg | atgaggattt | cattccaaag | gaaataccag | cttgtccacc | tgaggaagaa | 2375 |
|---|---|---|---|---|---|---|
| atgctttttt | cacaaggaga | caccaagaga | agactaggaa | gtagccctcg | ttctccaggg | 2435 |
| cacccaaaat | accagccttt | attgtctgca | tgattttagg | ggatatgggg | agggaacaag | 2495 |
| tagaagggaa | gagggaaatg | gagagcatcc | ttatgacttt | acaaagggtg | gaaatgagga | 2555 |
| tggagggata | cagaagtctg | cacagctgta | aaggttttat | agatgtcttt | gccttcsctt | 2615 |
| ctgaggaagg | gaagaagtaa | tgaaagcaca | tgtgaataac | cccttccatc | ccattcacag | 2675 |
| catcgcactc | ccagtcctta | aggcaaaggg | aggcagtgct | gaagcattgg | tggtgcagtg | 2735 |
| taaagacaca | agacctgatc | atctgatcac | acttgtgcca | acttgattca | tattgggcat | 2795 |
| tactaacaac | ccctggtcaa | ggtaaatagg | ttgaacaatc | aataacatta | tccctgcctg | 2855 |
| catacatgtg | aacaaaagct | atagaggaca | tgcaaattct | acagtcattc | ctcatatgct | 2915 |
| ttagacagag | tgcagctact | ggaatcttcc | agatttcagt | gttttaaaat | cagagctctg | 2975 |
| aatacacaaa | aggaaagaga | atggagcag | ctgacatatt | ttaagctcac | agtgatactc | 3035 |
| agtgacagga | gcacagagct | ctaatgtcca | caggatgttg | tagggtaggg | tctctcagta | 3095 |
| aatcaagtcc | cttacctatg | ttctgacact | gaggctcttg | gagctatggg | ttagaaatcc | 3155 |
| aggaggcaat | gtctttattc | taatgaagtc | ctcatcttgc | actcagaggc | ccactagttt | 3215 |
| gcccttctat | atattaagta | aaaccaagag | aaattaaaaa | aaaaa | | 3260 |

<210> SEQ ID NO 11
<211> LENGTH: 1165
<212> TYPE: DNA
<213> ORGANISM: Homo sapiens
<220> FEATURE:
<221> NAME/KEY: CDS
<222> LOCATION: (355)..(1071)
<223> OTHER INFORMATION:

<400> SEQUENCE: 11

| gctctcatat | tttcaaagga | agccggaaac | ctggactttt | aaagtgaaat | acccaccccc | 60 |
|---|---|---|---|---|---|---|
| cacaacattt | aagtactgac | taataatttt | tagaaacaac | ataggccaaa | caaaacacat | 120 |
| aggtggctcc | gagtttgtag | gtagcctgtg | gtttaatatc | tttctctccc | atttaactca | 180 |
| gctccacggg | gcacatggca | tctccctctg | ctcatcatag | tgtttggatc | aaacaaatga | 240 |
| aaaacagaaa | catgacggcc | tctaccagca | aaagctcgag | ggttggaaag | agtcccctgg | 300 |
| cagggaattg | gcaccccgtc | gtgcctatcc | tctctctctg | actgcctgct | ggaa atg | 357 |
| | | | | | | Met |
| | | | | | | 1 |

| ccc | cca | tct | ccc | ttt | gag | tcc | tcc | tcc | cgg | gcg | act | cct | gtg | acc tgt | 405 |
|---|---|---|---|---|---|---|---|---|---|---|---|---|---|---|---|
| Pro | Pro | Ser | Pro | Phe | Glu | Ser | Ser | Ser | Arg | Ala | Thr | Pro | Val | Thr Cys | |
| | 5 | | | | 10 | | | | 15 | | | | | | |

| aac | ctc | tgt | cct | gaa | atc | atc | aca | atg | gcc | agg | gtg | gcc | tca | gct caa | 453 |
|---|---|---|---|---|---|---|---|---|---|---|---|---|---|---|---|
| Asn | Leu | Cys | Pro | Glu | Ile | Ile | Thr | Met | Ala | Arg | Val | Ala | Ser | Ala Gln | |
| | 20 | | | | 25 | | | | 30 | | | | | | |

```
ggc ctc tgt gac atc acc aag ggc ctg gca cca ggt gcc cag tct tcc     501
Gly Leu Cys Asp Ile Thr Lys Gly Leu Ala Pro Gly Ala Gln Ser Ser
         35                  40                  45 agt tgc gag ggc aag caa acc cgt cat gag caa ctc cct tcc cca tct     549
Ser Cys Glu Gly Lys Gln Thr Arg His Glu Gln Leu Pro Ser Pro Ser
 50                  55                  60                  65 ctg ctc acc atg tgg acg ctg aaa tcg tcc ctg gtc ctg ctt ctg tgc     597
Leu Leu Thr Met Trp Thr Leu Lys Ser Ser Leu Val Leu Leu Leu Cys
                     70                  75                  80 ctc acc tgc agc tat gcc ttt atg ttc tct tct ctg aga cag aaa act     645
Leu Thr Cys Ser Tyr Ala Phe Met Phe Ser Ser Leu Arg Gln Lys Thr
                 85                  90                  95 agc gaa ccc cag ggg aag gtg caa tac gga gag cac ttt cgg att cgg     693
Ser Glu Pro Gln Gly Lys Val Gln Tyr Gly Glu His Phe Arg Ile Arg
             100                 105                 110 cag aat cta cca gag cac acc caa ggc tgg ctt ggg agc aaa tgg ctc     741
Gln Asn Leu Pro Glu His Thr Gln Gly Trp Leu Gly Ser Lys Trp Leu
         115                 120                 125 tgg ctt ctt ttt gtt gtt gtg ccg ttt gtg ata ctg cag tgt caa aga     789
Trp Leu Leu Phe Val Val Val Pro Phe Val Ile Leu Gln Cys Gln Arg
130                 135                 140                 145 gac agt gag aag aat aag gag cag agt cct cct ggc ctt cga ggc ggc     837
Asp Ser Glu Lys Asn Lys Glu Gln Ser Pro Pro Gly Leu Arg Gly Gly
                 150                 155                 160 caa ctt cac tct cca tta aag aaa aaa aga aat gct tcc ccc aac aaa     885
Gln Leu His Ser Pro Leu Lys Lys Lys Arg Asn Ala Ser Pro Asn Lys
             165                 170                 175 gac tgt gca ttc aat acc tta atg gaa ctc gag gtg gag ctt atg aaa     933
Asp Cys Ala Phe Asn Thr Leu Met Glu Leu Glu Val Glu Leu Met Lys
         180                 185                 190 ttt gtg tcc aaa gtg cgg aat ctt aaa cgt gcc atg gca aca ggt agt     981
Phe Val Ser Lys Val Arg Asn Leu Lys Arg Ala Met Ala Thr Gly Ser
     195                 200                 205 ggc agt aac ctc agg ctt cga aag tca gag atg cct gca gat cca tac    1029
Gly Ser Asn Leu Arg Leu Arg Lys Ser Glu Met Pro Ala Asp Pro Tyr
210                 215                 220                 225 cat gtc acg atc tgt gaa ata tgg gga gaa gaa agc tct agc                1071
His Val Thr Ile Cys Glu Ile Trp Gly Glu Glu Ser Ser Ser
                 230                 235 tgaatggatt tgtgtgtcag gagagaaaaa agttgagtgt tgacaaactg tatgcaaact    1131
aataaaacta ttctgaagaa aagaaaaaaa aaaa                               1165

<210> SEQ ID NO 12
<211> LENGTH: 969
<212> TYPE: DNA
<213> ORGANISM: Homo sapiens
<220> FEATURE:
<221> NAME/KEY: CDS
<222> LOCATION: (34)..(765)
<223> OTHER INFORMATION:

<400> SEQUENCE: 12
acgtctgtgg cgccctcgca ccgcgccgca gcc atg gcc ctg gtg acc ctg cag      54
                                    Met Ala Leu Val Thr Leu Gln
                                      1               5 cgc tcg ccc acg ccc agc gcc gcc tcc tcc tcg gcc agc aac agc gag     102
Arg Ser Pro Thr Pro Ser Ala Ala Ser Ser Ser Ala Ser Asn Ser Glu
             10                  15                  20 ttg gag gct ggc agc gaa gaa gat cga aaa tta aac ctc agc tta agt     150
Leu Glu Ala Gly Ser Glu Glu Asp Arg Lys Leu Asn Leu Ser Leu Ser
```

|  |  |
|---|---|
| gag agc ttt ttc atg gtg aaa ggc gca gcc ctc ttc tta caa cag gga<br>Glu Ser Phe Phe Met Val Lys Gly Ala Ala Leu Phe Leu Gln Gln Gly<br>40              45                  50                  55 | 198 |
| agc agc cct caa ggc cag cgg agt ctt cag cac ccc cac aag cat gca<br>Ser Ser Pro Gln Gly Gln Arg Ser Leu Gln His Pro His Lys His Ala<br>            60                  65                  70 | 246 |
| ggt gat ctg cct caa cat ctt cag gtg atg atc aac ctt ctg cgt tgc<br>Gly Asp Leu Pro Gln His Leu Gln Val Met Ile Asn Leu Leu Arg Cys<br>        75                  80                  85 | 294 |
| gaa gac aga atc aag ctg gca gtg cgc ctg gag agc gcc tgg gcg gac<br>Glu Asp Arg Ile Lys Leu Ala Val Arg Leu Glu Ser Ala Trp Ala Asp<br>    90                  95                  100 | 342 |
| cgg gtc cgg tac atg gtg gtg gtg tac agc agc ggg cgc cag gac acc<br>Arg Val Arg Tyr Met Val Val Val Tyr Ser Ser Gly Arg Gln Asp Thr<br>105                 110                 115 | 390 |
| gag gag aat atc ttg ctg gga gtg gac ttt tcc agt aag gaa agt aaa<br>Glu Glu Asn Ile Leu Leu Gly Val Asp Phe Ser Ser Lys Glu Ser Lys<br>120                 125                 130                 135 | 438 |
| agc tgc acc att ggg atg gtt ctc cga ctg tgg agc gac acg aaa atc<br>Ser Cys Thr Ile Gly Met Val Leu Arg Leu Trp Ser Asp Thr Lys Ile<br>            140                 145                 150 | 486 |
| cac ctt gat gga gat ggt ggg ttc agc gtg agc aca gca gga agg atg<br>His Leu Asp Gly Asp Gly Gly Phe Ser Val Ser Thr Ala Gly Arg Met<br>        155                 160                 165 | 534 |
| cac ata ttt aag cct gtg tct gtc cag gcc atg tgg tct gcc ctg cag<br>His Ile Phe Lys Pro Val Ser Val Gln Ala Met Trp Ser Ala Leu Gln<br>    170                 175                 180 | 582 |
| gtg ctt cac aag gcc tgc gaa gtg gcc cgg agg cac aac tac ttc ccc<br>Val Leu His Lys Ala Cys Glu Val Ala Arg Arg His Asn Tyr Phe Pro<br>185                 190                 195 | 630 |
| ggg ggt gta gct ctc atc tgg gct acc tac tat gag agc tgc atc agc<br>Gly Gly Val Ala Leu Ile Trp Ala Thr Tyr Tyr Glu Ser Cys Ile Ser<br>200                 205                 210                 215 | 678 |
| tcc gag cag agc tgc atc aac gag tgg aac gcc atg cag gac ctg gag<br>Ser Glu Gln Ser Cys Ile Asn Glu Trp Asn Ala Met Gln Asp Leu Glu<br>            220                 225                 230 | 726 |
| tct acg cgg ccc gac tcc ccc gcg cta ttt gtg gac aag taagtgaggt<br>Ser Thr Arg Pro Asp Ser Pro Ala Leu Phe Val Asp Lys<br>        235                 240 | 775 |
| gcctctggtg tgagcgcacc caagcccaca ggcacctgcc tctcccccac ctgccctgtg | 835 |
| cccgaccctg aacctgcatt gggccacacc tcccctggag tcccttgagt gagaacccta | 895 |
| gctttctcag aaccagcgtt taaagcaggg gtctgtgaca caggcccctg tcccatgcaa | 955 |
| aaaaaagaaa aaag | 969 |

<210> SEQ ID NO 13
<211> LENGTH: 1611
<212> TYPE: DNA
<213> ORGANISM: Homo sapiens
<220> FEATURE:
<221> NAME/KEY: CDS
<222> LOCATION: (380)..(1141)
<223> OTHER INFORMATION:

<400> SEQUENCE: 13

|  |  |
|---|---|
| tttcgtgtgg agggcacgtg cggagctgtg tctggggtct gcttccatat agaccacccc | 60 |
| gagaacaggt gactctcctg gcaatgaaac ctgggccacc agcccagaga ggcctctcac | 120 |
| cacagcaggg accaaggctg cctttgtgca aggcaccagc cccaccccec aaggcctgcc | 180 |

-continued

```
ccagcggctg aacctgaccg gagcagtcag ggtgctctgt gagatcgaga aggtggttgt        240
cgccatccag aagcgcttcc tgcagcagga atccatcccc gagtcctcgt tgcacctcag        300
ccacccctcc tgcaacgtga gccacagcaa tggcacacac gtgctcctgg aggccggctg        360
gagcgagtgt gggaccctc atg cag agc aac atg acg aac acc gtg gtg agg        412
                     Met Gln Ser Asn Met Thr Asn Thr Val Val Arg
                      1               5                  10
```

```
acc acg ctg agg aac gac ctg tcc cag gag ggc atc atc cac cac ctg         460
Thr Thr Leu Arg Asn Asp Leu Ser Gln Glu Gly Ile Ile His His Leu
             15                  20                  25 aag atc ctg agc ccc atc tac tgc gcc ttc cag aat gac ctg ctg aca         508
Lys Ile Leu Ser Pro Ile Tyr Cys Ala Phe Gln Asn Asp Leu Leu Thr
         30                  35                  40 tcc tcc ggc ttc acc ctg gag tgg ggg gtt tac acc atc atc gag gac         556
Ser Ser Gly Phe Thr Leu Glu Trp Gly Val Tyr Thr Ile Ile Glu Asp
     45                  50                  55 ctc cac ggc gct ggg aat ttt gtt acc gaa atg cag ttg ttt atc gga         604
Leu His Gly Ala Gly Asn Phe Val Thr Glu Met Gln Leu Phe Ile Gly
60                  65                  70                  75 gac tct ccc ata cct cag aat tat agc gtg tct gcc agt gac gat gtc         652
Asp Ser Pro Ile Pro Gln Asn Tyr Ser Val Ser Ala Ser Asp Asp Val
                 80                  85                  90 agg atc gaa gtg ggg ctc tac agg cag aaa agc aac ctc aag gtg gtc         700
Arg Ile Glu Val Gly Leu Tyr Arg Gln Lys Ser Asn Leu Lys Val Val
             95                 100                 105 ctg acg gag tgc tgg gca acc ccg tct agc aac gcc cgg gac ccc atc         748
Leu Thr Glu Cys Trp Ala Thr Pro Ser Ser Asn Ala Arg Asp Pro Ile
         110                 115                 120 acc ttc agc ttc att aac aac agc tgc cct gtg ccc aac aca tac acc         796
Thr Phe Ser Phe Ile Asn Asn Ser Cys Pro Val Pro Asn Thr Tyr Thr
     125                 130                 135 aac gtg att gag aac ggc aac tcc aat aag gcc cag ttc aag ctg agg        844
Asn Val Ile Glu Asn Gly Asn Ser Asn Lys Ala Gln Phe Lys Leu Arg
140                 145                 150                 155 atc ttt tcc ttt atc aac gac tcc atc gtc tac ctg cac tgc aaa ctc         892
Ile Phe Ser Phe Ile Asn Asp Ser Ile Val Tyr Leu His Cys Lys Leu
                 160                 165                 170 cgc gtc tgc atg gaa tcc ccc gga gcc acg tgc aaa atc atc tct cac         940
Arg Val Cys Met Glu Ser Pro Gly Ala Thr Cys Lys Ile Ile Ser His
             175                 180                 185 ctg tgc ctg tct cct ccc cga ggt gag cct cct cat gca gaa gca ggc         988
Leu Cys Leu Ser Pro Pro Arg Gly Glu Pro Pro His Ala Glu Ala Gly
         190                 195                 200 ctg ggt gcc ggt tat gtg gtc ctt att gtg gtg gcc atc ttc gtg ctg        1036
Leu Gly Ala Gly Tyr Val Val Leu Ile Val Val Ala Ile Phe Val Leu
     205                 210                 215 gtg gcg gga aca gcc acc ctt ctg atc gtg cgc tac cag aga atg aat       1084
Val Ala Gly Thr Ala Thr Leu Leu Ile Val Arg Tyr Gln Arg Met Asn
220                 225                 230                 235 ggg aga tac aac ttt aaa atc cag tcc aac aac ttc agc tac cag gtg        1132
Gly Arg Tyr Asn Phe Lys Ile Gln Ser Asn Asn Phe Ser Tyr Gln Val
                 240                 245                 250 ttc tac gaa taggaggcac aggctgacag gaaggtcgcc gtgagtcaag                1181
Phe Tyr Glu
```

```
ctgcctccag aacctcagag cttccctggt gggctccccc gggatcccca gtgtctctct       1241
gcacctccac ccatccctcg gttcttaact cttcaagcct taacggaggt ctgctctgac      1301
gggtgggctc tgccagagcc cgggtgagcc cagaaaggaa gacagcagcc accgtctgtc      1361
```

-continued

```
ccgaagaggc aggccgtcct gtaggtccta gaggagccac agcccagggg cagatgaagg      1421
ggctgcggaa gacgggggca gtcctggggg tgctgcggct acaccaccac ccgcgcggcc      1481
cccgcagccc agacctccca ggcctgtgac cctccacacc agccctcaga accctcctgg      1541
gcttgccctc ccttggcgtc cgtcacccct tggcaaatat agaatatttc acattctcaa      1601
aaaaaaaaaa                                                             1611

<210> SEQ ID NO 14
<211> LENGTH: 1114
<212> TYPE: DNA
<213> ORGANISM: Homo sapiens
<220> FEATURE:
<221> NAME/KEY: CDS
<222> LOCATION: (131)..(952)
<223> OTHER INFORMATION:

<400> SEQUENCE: 14
gtgtcttcct tcccagcttc ctccgtgtct ggggtggggg atgggggggt ctcaggcagg       60
gatactctag cccctggact gctgtttaga cccagcttgt actgctgctg ctccctgccc      120
agccccagcc atg aaa ctg ccc aag ggg acc agg agc tct gtg tac ttt        169
            Met Lys Leu Pro Lys Gly Thr Arg Ser Ser Val Tyr Phe
              1               5                  10 gca cag cac cca gaa aag gag cca ttg ccc tca agg cag gag gtc aag        217
Ala Gln His Pro Glu Lys Glu Pro Leu Pro Ser Arg Gln Glu Val Lys
 15                  20                  25 cag acc cct gtc atc atg gcc aag atc aaa ggt ccg ggg ccc gcc aag        265
Gln Thr Pro Val Ile Met Ala Lys Ile Lys Gly Pro Gly Pro Ala Lys
 30                  35                  40                  45 tac ctc cgg cca tcc tgc acg ggc tac ata gat cat gac atc tcc atg        313
Tyr Leu Arg Pro Ser Cys Thr Gly Tyr Ile Asp His Asp Ile Ser Met
                 50                  55                  60 ttc aag gca cca gct tat acc ctg cat agc cgg cac tca gag aag cgg        361
Phe Lys Ala Pro Ala Tyr Thr Leu His Ser Arg His Ser Glu Lys Arg
             65                  70                  75 atg gtg tgc cac agc agc cct ggg cct tgt tat ctc ttg gat ccc aaa        409
Met Val Cys His Ser Ser Pro Gly Pro Cys Tyr Leu Leu Asp Pro Lys
         80                  85                  90 ata act cgg ttt gga atg tcc agc tgc ccg cag gtc ccc atg gag gag        457
Ile Thr Arg Phe Gly Met Ser Ser Cys Pro Gln Val Pro Met Glu Glu
     95                 100                 105 cgc atc tcc aac ctg cgc ctg aac ccc acc ctc gca tcc tgc cag tac        505
Arg Ile Ser Asn Leu Arg Leu Asn Pro Thr Leu Ala Ser Cys Gln Tyr
110                 115                 120                 125 tac ttt gag aag atc cac cca ccg ggg gaa cgc agg gct ccc cag tac        553
Tyr Phe Glu Lys Ile His Pro Pro Gly Glu Arg Arg Ala Pro Gln Tyr
                130                 135                 140 acg ttt ggc tac cgg cgc cca tac aga gtg atg gac ctc aac ccg gct        601
Thr Phe Gly Tyr Arg Arg Pro Tyr Arg Val Met Asp Leu Asn Pro Ala
            145                 150                 155 ccc aac cag tac cag atg cca ctc ttg ctg ggg ccc aac acc cct gtc        649
Pro Asn Gln Tyr Gln Met Pro Leu Leu Leu Gly Pro Asn Thr Pro Val
        160                 165                 170 agc cga gct gct ccc tgc tac agt ctg gcc tcc agg gac aag aac tgg        697
Ser Arg Ala Ala Pro Cys Tyr Ser Leu Ala Ser Arg Asp Lys Asn Trp
    175                 180                 185 ttc tac aag gag gat gtg gca gga ggc cct gga cct acc acg tac gcc        745
Phe Tyr Lys Glu Asp Val Ala Gly Gly Pro Gly Pro Thr Thr Tyr Ala
190                 195                 200                 205 cga cct gag cca tcc atc tat cag aac cgc agc cct act tac agc atg        793
```

| | | |
|---|---|---|
| Arg Pro Glu Pro Ser Ile Tyr Gln Asn Arg Ser Pro Thr Tyr Ser Met<br>210 215 220 | | |
| gcc aag cgc ttc gcc tac cct ctg gac ctc acg cca cgg cct ggc ccc<br>Ala Lys Arg Phe Ala Tyr Pro Leu Asp Leu Thr Pro Arg Pro Gly Pro<br>225 230 235 | 841 | |
| ggc tcc cac gag gtc cag cag gtc act gtg cac aag ccc cac atc cct<br>Gly Ser His Glu Val Gln Gln Val Thr Val His Lys Pro His Ile Pro<br>240 245 250 | 889 | |
| gct ttc acc atg ggc atc aag cac tca ctc cac ctg tgc cca ctg gtc<br>Ala Phe Thr Met Gly Ile Lys His Ser Leu His Leu Cys Pro Leu Val<br>255 260 265 | 937 | |
| atc gac att cgt gac tgaggcccct cttggggcac tcactgcccc tcatccccag<br>Ile Asp Ile Arg Asp<br>270 | 992 | |
| aaattatttt tctacaccaa attgagcaat ttgaccaaga tttctagtag cagagccggt | 1052 | |
| acctgctgag tgtccggcac acagaagaca ttagagatac attttcatgt aaaaaaaaaa | 1112 | |
| aa | 1114 | |

```
<210> SEQ ID NO 15
<211> LENGTH: 1658
<212> TYPE: DNA
<213> ORGANISM: Homo sapiens
<220> FEATURE:
<221> NAME/KEY: CDS
<222> LOCATION: (351)..(1388)
<223> OTHER INFORMATION:

<400> SEQUENCE: 15
```

| | |
|---|---|
| agacaggccg acgtcgcaa ggtcctacgg tcaagcatcc gggagtttct atgcagcgaa | 60 |
| gccatgttcc acctgggagt ccccaccaca cgggccggcg cctgcgtcac gtccgagtcc | 120 |
| acggtggtgc gcgacgtgtt ctatgatggt ttggatcctt tgagatttt aagtctgcag | 180 |
| atgagcacac agggcgtgca ggccccagcg tggggaggaa cgacattcga gtgcagctgc | 240 |
| tcgactatgt catcagctcc ttttaccccg agatccaggc tgctcatgcc agcgacagcg | 300 |
| tgcagagaaa tgctgccttc ttccgggagg tgacgcggcg cacggcgcgg atg gtg<br>Met Val<br>1 | 356 |
| gcc gag tgg cag tgt gtg ggc ttc tgc cac ggc gtg ctc aac acc gac<br>Ala Glu Trp Gln Cys Val Gly Phe Cys His Gly Val Leu Asn Thr Asp<br>5 10 15 | 404 |
| aac atg agc atc ctg ggg ctc acc atc gac tac ggg ccc ttt ggc ttc<br>Asn Met Ser Ile Leu Gly Leu Thr Ile Asp Tyr Gly Pro Phe Gly Phe<br>20 25 30 | 452 |
| ctg gac agg tac gac ccc gac cac gtg tgc aat gcc tcc gac aac acc<br>Leu Asp Arg Tyr Asp Pro Asp His Val Cys Asn Ala Ser Asp Asn Thr<br>35 40 45 50 | 500 |
| ggc cgc tac gcg tac agc aag cag ccc gag gtg tgc agg tgg aac ctg<br>Gly Arg Tyr Ala Tyr Ser Lys Gln Pro Glu Val Cys Arg Trp Asn Leu<br>55 60 65 | 548 |
| cgg aag ctg gcc gag gcc ctg cag ccg gaa ctg ccc ctg gag ctg ggg<br>Arg Lys Leu Ala Glu Ala Leu Gln Pro Glu Leu Pro Leu Glu Leu Gly<br>70 75 80 | 596 |
| gag gcc atc ctg gcc gag gag ttt gac gcc gag ttc caa agg cac tac<br>Glu Ala Ile Leu Ala Glu Glu Phe Asp Ala Glu Phe Gln Arg His Tyr<br>85 90 95 | 644 |
| ctg cag aag atg cgc agg aag ctg ggc ctc gtg cag gtg gag ctg gag<br>Leu Gln Lys Met Arg Arg Lys Leu Gly Leu Val Gln Val Glu Leu Glu<br>100 105 110 | 692 |
| gaa gac ggg gcg ctg gtg tcc aag ctc ctg gag acc atg cat ctg acc | 740 |

-continued

| | | |
|---|---|---|
| Glu Asp Gly Ala Leu Val Ser Lys Leu Leu Glu Thr Met His Leu Thr<br>115                    120                  125                  130 | | |
| ggt gcc gac ttc aca aac acc ttc tac ttg ctg agc tcc ttc cca gtg<br>Gly Ala Asp Phe Thr Asn Thr Phe Tyr Leu Leu Ser Ser Phe Pro Val<br>                    135                  140                  145 | 788 | |
| gag cta gag tcg cca ggc ctg gcg gaa ttc ctg gcc agg ctg atg gag<br>Glu Leu Glu Ser Pro Gly Leu Ala Glu Phe Leu Ala Arg Leu Met Glu<br>            150                  155                  160 | 836 | |
| cag tgt gcc tcc ctg gag gag ctg agg ctg gcc ttc cgg ccc cag atg<br>Gln Cys Ala Ser Leu Glu Glu Leu Arg Leu Ala Phe Arg Pro Gln Met<br>       165                  170                  175 | 884 | |
| gat ccc cgg cag cta tcc atg atg ctg atg ctg gcg cag tca aac ccg<br>Asp Pro Arg Gln Leu Ser Met Met Leu Met Leu Ala Gln Ser Asn Pro<br>180                    185                  190 | 932 | |
| cag ctg ttc gcg ctt atg ggc acc cgg gca ggc atc gcc agg gag ctg<br>Gln Leu Phe Ala Leu Met Gly Thr Arg Ala Gly Ile Ala Arg Glu Leu<br>195                    200                  205                  210 | 980 | |
| gag cgt gtg gag cag cag tct cgg ctg gag cag ctg agt gcg gca gag<br>Glu Arg Val Glu Gln Gln Ser Arg Leu Glu Gln Leu Ser Ala Ala Glu<br>            215                  220                  225 | 1028 | |
| ctg cag agc agg aac cag ggc cac tgg gct gac tgg cta cag gcg tac<br>Leu Gln Ser Arg Asn Gln Gly His Trp Ala Asp Trp Leu Gln Ala Tyr<br>       230                  235                  240 | 1076 | |
| aga gcc cgg ctg gac aag gac ctg gaa ggc gct ggg gac gct gcc gcc<br>Arg Ala Arg Leu Asp Lys Asp Leu Glu Gly Ala Gly Asp Ala Ala Ala<br>245                    250                  255 | 1124 | |
| tgg cag gct gag cac gtg cgc gtg atg cac gcc aac aac ccg aag tac<br>Trp Gln Ala Glu His Val Arg Val Met His Ala Asn Asn Pro Lys Tyr<br>260                    265                  270 | 1172 | |
| gtg ctg agg aac tac atc gcg cag aat gcc atc gag gct gcc gag cgc<br>Val Leu Arg Asn Tyr Ile Ala Gln Asn Ala Ile Glu Ala Ala Glu Arg<br>275                    280                  285                  290 | 1220 | |
| ggg gac ttc tca gag gtg cgg cgg gtg ctg aaa cta ctg gag acc cct<br>Gly Asp Phe Ser Glu Val Arg Arg Val Leu Lys Leu Leu Glu Thr Pro<br>            295                  300                  305 | 1268 | |
| tac cac tgc gag gcg ggg gcc gcc aca gac gcc gag gcc acg gaa gcc<br>Tyr His Cys Glu Ala Gly Ala Ala Thr Asp Ala Glu Ala Thr Glu Ala<br>       310                  315                  320 | 1316 | |
| gac ggg gcg gac ggc agg cag cgc tcc tac agc agt aag ccc ccg ctc<br>Asp Gly Ala Asp Gly Arg Gln Arg Ser Tyr Ser Ser Lys Pro Pro Leu<br>325                    330                  335 | 1364 | |
| tgg gca gca gaa ctg tgc gtg aca tgatcttcgt aacggcctcg gcacgctcca<br>Trp Ala Ala Glu Leu Cys Val Thr<br>340                    345 | 1418 | |
| caccccctgga gtctcccgag gcccccatgt gctgctgagt ggccaagatg atgccaggct | 1478 | |
| gccctataca ctgggggatt ctgccctggc ccatgcacac ccgtctttcc atgatggcag | 1538 | |
| agacatccag tcaggacctg acccgtctct gtctgaggcc ggctcagcag tgcagcctgg | 1598 | |
| tccctggggg ctgacccag gctcctaaat aaaccagcaa ctccctcgaa aaaaaaaaa | 1658 | |

<210> SEQ ID NO 16
<211> LENGTH: 2499
<212> TYPE: DNA
<213> ORGANISM: Homo sapiens
<220> FEATURE:
<221> NAME/KEY: CDS
<222> LOCATION: (1)..(2145)
<223> OTHER INFORMATION:

<400> SEQUENCE: 16

-continued

| | | |
|---|---|---|
| atg gag cgc aca gca ggc aaa gag ctg gcc ctg gta agg gga caa ggg<br>Met Glu Arg Thr Ala Gly Lys Glu Leu Ala Leu Val Arg Gly Gln Gly<br>1               5                   10                  15 | | 48 |
| atc ccc gga ccc cgc atc cct ggt gac ccg cag gca ccg ctg cag gac<br>Ile Pro Gly Pro Arg Ile Pro Gly Asp Pro Gln Ala Pro Leu Gln Asp<br>            20                  25                  30 | | 96 |
| tgg ggt gaa gag acc gag gac ggc gcg gtg tac agt gtc tcc ctg cgg<br>Trp Gly Glu Glu Thr Glu Asp Gly Ala Val Tyr Ser Val Ser Leu Arg<br>        35                  40                  45 | | 144 |
| cgg cag cgc agt cag cgc agg agc ccg gcg gag ggc ccc ggg ggc agc<br>Arg Gln Arg Ser Gln Arg Arg Ser Pro Ala Glu Gly Pro Gly Gly Ser<br>    50                  55                  60 | | 192 |
| cag gct ccc agc ccc att gcc aat acc ttc ctc cac tat cga acc agc<br>Gln Ala Pro Ser Pro Ile Ala Asn Thr Phe Leu His Tyr Arg Thr Ser<br>65                  70                  75                  80 | | 240 |
| aag gtg agg gtg ctg agg gca gcg cgc ctg gag cgg ctg gtg gga gag<br>Lys Val Arg Val Leu Arg Ala Ala Arg Leu Glu Arg Leu Val Gly Glu<br>                85                  90                  95 | | 288 |
| ttg gtg ttt gga gac cgt gag cag gac ccc agc ttc atg ccc gcc ttc<br>Leu Val Phe Gly Asp Arg Glu Gln Asp Pro Ser Phe Met Pro Ala Phe<br>            100                 105                 110 | | 336 |
| ctg gcc acc tac cgg acc ttt gta ccc act gcc tgc ctg ctg ggc ttt<br>Leu Ala Thr Tyr Arg Thr Phe Val Pro Thr Ala Cys Leu Leu Gly Phe<br>        115                 120                 125 | | 384 |
| ctg ctg cca cca atg cca ccg ccc cca cct ccc ggg gta gag atc aag<br>Leu Leu Pro Pro Met Pro Pro Pro Pro Pro Pro Gly Val Glu Ile Lys<br>    130                 135                 140 | | 432 |
| aag aca gcg gta caa gat ctg agc ttc aac aag aac ctg agg gct gtg<br>Lys Thr Ala Val Gln Asp Leu Ser Phe Asn Lys Asn Leu Arg Ala Val<br>145                 150                 155                 160 | | 480 |
| gtg tca gtg ctg ggc tcc tgg ctg cag gac cac cct cag gat ttc cga<br>Val Ser Val Leu Gly Ser Trp Leu Gln Asp His Pro Gln Asp Phe Arg<br>                165                 170                 175 | | 528 |
| gac ccc cct gcc cat tcg gac ctg ggc agt gtc cga acc ttt ctg ggc<br>Asp Pro Pro Ala His Ser Asp Leu Gly Ser Val Arg Thr Phe Leu Gly<br>            180                 185                 190 | | 576 |
| tgg gcg gcc cca ggg agt gct gag gct caa aaa gca gag aag ctt ctg<br>Trp Ala Ala Pro Gly Ser Ala Glu Ala Gln Lys Ala Glu Lys Leu Leu<br>        195                 200                 205 | | 624 |
| gaa gat ttt ttg gag gag gct gag cga gag cag gaa gag gag ccg cct<br>Glu Asp Phe Leu Glu Glu Ala Glu Arg Glu Gln Glu Glu Glu Pro Pro<br>    210                 215                 220 | | 672 |
| cag gtg tgg aca gac tct tca gag gcc tgc gcg gag gaa gag gaa ggg<br>Gln Val Trp Thr Asp Ser Ser Glu Ala Cys Ala Glu Glu Glu Glu Gly<br>225                 230                 235                 240 | | 720 |
| ctc atg cct caa ggt ccc cag ctc ctg gac ttc agc gtg gac gag gtg<br>Leu Met Pro Gln Gly Pro Gln Leu Leu Asp Phe Ser Val Asp Glu Val<br>                245                 250                 255 | | 768 |
| gcc gag cag ctg acc ctc ata gac ttg gag ctc ttc tcc aag gtg agg<br>Ala Glu Gln Leu Thr Leu Ile Asp Leu Glu Leu Phe Ser Lys Val Arg<br>            260                 265                 270 | | 816 |
| ctc tac gag tgc ttg ggc tcc gtg tgg tcg cag agg gac cgg ccg ggg<br>Leu Tyr Glu Cys Leu Gly Ser Val Trp Ser Gln Arg Asp Arg Pro Gly<br>        275                 280                 285 | | 864 |
| gct gca ggc gcc tcc ccc act gtg cgc gcc acc gtg gcc cag ttc aac<br>Ala Ala Gly Ala Ser Pro Thr Val Arg Ala Thr Val Ala Gln Phe Asn<br>    290                 295                 300 | | 912 |
| acc gtg acc ggc tgt gtg ctg ggt tcc gtg ctc gga gca ccg ggc ttg<br>Thr Val Thr Gly Cys Val Leu Gly Ser Val Leu Gly Ala Pro Gly Leu<br>305                 310                 315                 320 | | 960 |

-continued

```
gcc gcc ccg cag agg gcg cag cgg ctg gag aag tgg atc cgc atc gcc    1008
Ala Ala Pro Gln Arg Ala Gln Arg Leu Glu Lys Trp Ile Arg Ile Ala
            325                 330                 335 cag cgc tgc cga gaa ctg cgg aac ttc tcc tcc ttg cgc gcc atc ctg    1056
Gln Arg Cys Arg Glu Leu Arg Asn Phe Ser Ser Leu Arg Ala Ile Leu
            340                 345                 350 tcc gcc ctg caa tct aac ccc atc tac cgg ctc aag cgc agc tgg ggg    1104
Ser Ala Leu Gln Ser Asn Pro Ile Tyr Arg Leu Lys Arg Ser Trp Gly
            355                 360                 365 gca gtg agc cgg gaa ccg cta tct act ttc agg aaa ctt tcg cag att    1152
Ala Val Ser Arg Glu Pro Leu Ser Thr Phe Arg Lys Leu Ser Gln Ile
    370                 375                 380 ttc tcc gat gag aac aac cac ctc agc agc aga gag att ctt ttc cag    1200
Phe Ser Asp Glu Asn Asn His Leu Ser Ser Arg Glu Ile Leu Phe Gln
385                 390                 395                 400 gag gag gcc act gag gga tcc caa gaa gag gac aac acc cca ggc agc    1248
Glu Glu Ala Thr Glu Gly Ser Gln Glu Glu Asp Asn Thr Pro Gly Ser
                405                 410                 415 ctg ccc tca aaa cca ccc cca ggc cct gtc ccc tac ctt ggc acc ttc    1296
Leu Pro Ser Lys Pro Pro Pro Gly Pro Val Pro Tyr Leu Gly Thr Phe
            420                 425                 430 ctt acg gac ctg gtt atg ctg gac aca gcc ctg ccg gat atg ttg gag    1344
Leu Thr Asp Leu Val Met Leu Asp Thr Ala Leu Pro Asp Met Leu Glu
            435                 440                 445 ggg gat ctc att aac ttt gag aag agg agg aag gag tgg gag atc ctg    1392
Gly Asp Leu Ile Asn Phe Glu Lys Arg Arg Lys Glu Trp Glu Ile Leu
            450                 455                 460 gcc cgc atc cag cag ctg cag agg cgc tgt cag agc tac acc ctg agc    1440
Ala Arg Ile Gln Gln Leu Gln Arg Arg Cys Gln Ser Tyr Thr Leu Ser
465                 470                 475                 480 ccc cac ccg ccc atc ctg gct gcc ctg cat gcc cag aac cag ctc acc    1488
Pro His Pro Pro Ile Leu Ala Ala Leu His Ala Gln Asn Gln Leu Thr
                485                 490                 495 gag gag cag agc tac cgg ctc tcc cgg gtc att gag cca cca gct gcc    1536
Glu Glu Gln Ser Tyr Arg Leu Ser Arg Val Ile Glu Pro Pro Ala Ala
            500                 505                 510 tcc tgc ccc agc tcc cca cgc atc cga cgg cgg atc agc ctc acc aag    1584
Ser Cys Pro Ser Ser Pro Arg Ile Arg Arg Arg Ile Ser Leu Thr Lys
            515                 520                 525 cgt ctc agt gcg aag ctt gcc cga gag aaa agc tca tca cct agt ggg    1632
Arg Leu Ser Ala Lys Leu Ala Arg Glu Lys Ser Ser Ser Pro Ser Gly
    530                 535                 540 agt ccc ggg gac ccc tca tcc ccc acc tcc agt gtg tcc cca ggg tca    1680
Ser Pro Gly Asp Pro Ser Ser Pro Thr Ser Ser Val Ser Pro Gly Ser
545                 550                 555                 560 ccc ccc tca agt cct aga agc aga gat gct cct gct ggc agt ccc ccg    1728
Pro Pro Ser Ser Pro Arg Ser Arg Asp Ala Pro Ala Gly Ser Pro Pro
                565                 570                 575 gcc tct cca ggg ccc cag ggc ccc agc acc aag ctg ccc ctg agc ctg    1776
Ala Ser Pro Gly Pro Gln Gly Pro Ser Thr Lys Leu Pro Leu Ser Leu
            580                 585                 590 gac ctg ccc agc ccc cgg ccc ttc gct ttg cct ctg ggc agc cct cga    1824
Asp Leu Pro Ser Pro Arg Pro Phe Ala Leu Pro Leu Gly Ser Pro Arg
            595                 600                 605 atc ccc ctc ccg gcg cag cag agc tcg gag gcc cgt gtc atc cgc gtc    1872
Ile Pro Leu Pro Ala Gln Gln Ser Ser Glu Ala Arg Val Ile Arg Val
            610                 615                 620 agc atc gac aat gac cac ggg aac ctg tat cga agc atc ttg ctg acc    1920
Ser Ile Asp Asn Asp His Gly Asn Leu Tyr Arg Ser Ile Leu Leu Thr
```

-continued

```
                625                 630                 635                 640
agt cag gac aaa gcc ccc agc gtg gtc cgg cga gcc ttg cag aag cac      1968
Ser Gln Asp Lys Ala Pro Ser Val Val Arg Arg Ala Leu Gln Lys His
                    645                 650                 655 aat gtg ccc cag ccc tgg gcc tgt gac tat cag ctc ttt caa gtc ctt      2016
Asn Val Pro Gln Pro Trp Ala Cys Asp Tyr Gln Leu Phe Gln Val Leu
                660                 665                 670 cct ggg gac cgg gtg ctc ctg att cct gac aat gcc aac gtc ttc tat      2064
Pro Gly Asp Arg Val Leu Leu Ile Pro Asp Asn Ala Asn Val Phe Tyr
            675                 680                 685 gcc atg agt cca gtc gcc ccc aga gac ttc atg ctg cgg cgg aaa gag      2112
Ala Met Ser Pro Val Ala Pro Arg Asp Phe Met Leu Arg Arg Lys Glu
        690                 695                 700 ggg acc cgg aac act ctg tct gtc tcc cca agc tgaggcagcc ctgtcctctc    2165
Gly Thr Arg Asn Thr Leu Ser Val Ser Pro Ser
705                 710                 715 cacaagacac aagtcccaca ggcaagcttg cgactcttct cctggaaagc tgccatcccc    2225
cagtagaggc cactgtgctg tgtatcccag gaccaccacc caactgtagc ccattggacc    2285
ccatctcttt ttctgactct gttggtacta gatccatatt ccaaagacat cagcccatgg    2345
gtggctggtg gagagctcaa tcccataaat gtagaaagag gtgggcatg gatacgtcaa     2405 atccctcccc agagaaatct tataaatgtt agagacgcat cagaagtgac agatgcggat    2465
gaaaatagtg accagagtta tgaaaaaaaa aaaa                                2499

<210> SEQ ID NO 17
<211> LENGTH: 2451
<212> TYPE: DNA
<213> ORGANISM: Homo sapiens
<220> FEATURE:
<221> NAME/KEY: CDS
<222> LOCATION: (1)..(2097)
<223> OTHER INFORMATION:

<400> SEQUENCE: 17 atg gag cgc aca gca ggc aaa gag ctg gcc ctg gta agg gga caa ggg        48
Met Glu Arg Thr Ala Gly Lys Glu Leu Ala Leu Val Arg Gly Gln Gly
1               5                   10                  15 atc ccc gga ccc cgc atc cct ggt gac ccg cag gca ccg ctg cag gac        96
Ile Pro Gly Pro Arg Ile Pro Gly Asp Pro Gln Ala Pro Leu Gln Asp
            20                  25                  30 tgg ggt gaa gag acc gag gac ggc gcg gtg tac agt gtc tcc ctg cgg       144
Trp Gly Glu Glu Thr Glu Asp Gly Ala Val Tyr Ser Val Ser Leu Arg
        35                  40                  45 cgg cag cgc agt cag cgc agg agc ccg gcg gag ggc ccc ggg ggc agc       192
Arg Gln Arg Ser Gln Arg Arg Ser Pro Ala Glu Gly Pro Gly Gly Ser
    50                  55                  60 cag gct ccc agc ccc att gcc aat acc ttc ctc cac tat cga acc agc       240
Gln Ala Pro Ser Pro Ile Ala Asn Thr Phe Leu His Tyr Arg Thr Ser
65                  70                  75                  80 aag gtg agg gtg ctg agg gca gcg cgc ctg gag cgg ctg gtg gga gag       288
Lys Val Arg Val Leu Arg Ala Ala Arg Leu Glu Arg Leu Val Gly Glu
                85                  90                  95 ttg gtg ttt gga gac cgt gag cag gac ccc agc ttc atg ccc gcc ttc       336
Leu Val Phe Gly Asp Arg Glu Gln Asp Pro Ser Phe Met Pro Ala Phe
            100                 105                 110 ctg gcc acc tac cgg acc ttt gta ccc act gcc tgc ctg ctg ggc ttt       384
Leu Ala Thr Tyr Arg Thr Phe Val Pro Thr Ala Cys Leu Leu Gly Phe
        115                 120                 125 ctg ctg cca cca atg cca ccg ccc cca cct ccc ggg gta gag atc aag       432
```

```
Leu Leu Pro Pro Met Pro Pro Pro Pro Pro Gly Val Glu Ile Lys
        130             135             140 aag aca gcg gta caa gat ctg agc ttc aac aag aac ctg agg gct gtg         480
Lys Thr Ala Val Gln Asp Leu Ser Phe Asn Lys Asn Leu Arg Ala Val
145             150             155             160 gtg tca gtg ctg ggc tcc tgg ctg cag gac cac cct cag gat ttc cga         528
Val Ser Val Leu Gly Ser Trp Leu Gln Asp His Pro Gln Asp Phe Arg
            165             170             175 gac ccc cct gcc cat tcg gac ctg ggc agt gtc cga acc ttt ctg ggc         576
Asp Pro Pro Ala His Ser Asp Leu Gly Ser Val Arg Thr Phe Leu Gly
        180             185             190 tgg gcg gcc cca ggg agt gct gag gct caa aaa gca gag aag ctt ctg         624
Trp Ala Ala Pro Gly Ser Ala Glu Ala Gln Lys Ala Glu Lys Leu Leu
            195             200             205 gaa gat ttt ttg gag gag gct gag cga gag caa gag gag ccg cct             672
Glu Asp Phe Leu Glu Glu Ala Glu Arg Glu Gln Glu Glu Pro Pro
210             215             220 cag gtg tgg aca gac tct tca gag gcc tgc gcg gag gaa gag gaa ggg         720
Gln Val Trp Thr Asp Ser Ser Glu Ala Cys Ala Glu Glu Glu Glu Gly
225             230             235             240 ctc atg cct caa ggt ccc cag ctc ctg gac ttc agc gtg gac gag gtg         768
Leu Met Pro Gln Gly Pro Gln Leu Leu Asp Phe Ser Val Asp Glu Val
            245             250             255 gcc gag cag ctg acc ctc ata gac ttg gag ctc ttc tcc aag gtg agg         816
Ala Glu Gln Leu Thr Leu Ile Asp Leu Glu Leu Phe Ser Lys Val Arg
        260             265             270 ctc tac gag tgc ttg ggc tcc gtg tgg tcg cag agg gac cgg ccg ggg         864
Leu Tyr Glu Cys Leu Gly Ser Val Trp Ser Gln Arg Asp Arg Pro Gly
            275             280             285 gct gca ggc gcc tcc ccc act gtg cgc gcc acc gtg gcc cag ttc aac         912
Ala Ala Gly Ala Ser Pro Thr Val Arg Ala Thr Val Ala Gln Phe Asn
290             295             300 acc gtg acc ggc tgt gtg ctg ggt tcc gtg ctc gga gca ccg ggc ttg         960
Thr Val Thr Gly Cys Val Leu Gly Ser Val Leu Gly Ala Pro Gly Leu
305             310             315             320 gcc gcc ccg cag agg gcg cag cgg ctg gag aag tgg atc cgc atc gcc        1008
Ala Ala Pro Gln Arg Ala Gln Arg Leu Glu Lys Trp Ile Arg Ile Ala
            325             330             335 cag cgc tgc cga gaa ctg cgg aac ttc tcc tcc ttg cgc gcc atc ctg        1056
Gln Arg Cys Arg Glu Leu Arg Asn Phe Ser Ser Leu Arg Ala Ile Leu
        340             345             350 tcc gcc ctg caa tct aac ccc atc tac cgg ctc aag cgc agc tgg ggg        1104
Ser Ala Leu Gln Ser Asn Pro Ile Tyr Arg Leu Lys Arg Ser Trp Gly
            355             360             365 gca gtg agc cgg gaa ccg cta tct act ttc agg aaa ctt tcg cag att        1152
Ala Val Ser Arg Glu Pro Leu Ser Thr Phe Arg Lys Leu Ser Gln Ile
370             375             380 ttc tcc gat gag aac aac cac ctc agc agc aga gag att ctt ttc cag        1200
Phe Ser Asp Glu Asn Asn His Leu Ser Ser Arg Glu Ile Leu Phe Gln
385             390             395             400 gag gag gcc act gag gga tcc caa gaa gag gac aac acc cca ggc agc        1248
Glu Glu Ala Thr Glu Gly Ser Gln Glu Glu Asp Asn Thr Pro Gly Ser
            405             410             415 ctg ccc tca aaa cca ccc cca ggc cct gtc ccc tac ctt ggc acc ttc        1296
Leu Pro Ser Lys Pro Pro Pro Gly Pro Val Pro Tyr Leu Gly Thr Phe
        420             425             430 ctt acg gac ctg gtt atg ctg gac aca gcc ctg ccg gat atg ttg gag        1344
Leu Thr Asp Leu Val Met Leu Asp Thr Ala Leu Pro Asp Met Leu Glu
            435             440             445
```

-continued

```
ggg gat ctc att aac ttt gag aag agg agg aag gag tgg gag atc ctg      1392
Gly Asp Leu Ile Asn Phe Glu Lys Arg Arg Lys Glu Trp Glu Ile Leu
450                 455                 460 gcc cgc atc cag cag ctg cag agg cgc tgt cag agc tac acc ctg agc      1440
Ala Arg Ile Gln Gln Leu Gln Arg Arg Cys Gln Ser Tyr Thr Leu Ser
465                 470                 475                 480 ccc cac ccg ccc atc ctg gct gcc ctg cat gcc cag aac cag ctc acc      1488
Pro His Pro Pro Ile Leu Ala Ala Leu His Ala Gln Asn Gln Leu Thr
                485                 490                 495 gag gag cag agc tac cgg ctc tcc cgg gtc att gag cca cca gct gcc      1536
Glu Glu Gln Ser Tyr Arg Leu Ser Arg Val Ile Glu Pro Pro Ala Ala
            500                 505                 510 tcc tgc ccc agc tcc cca cgc atc cga cgg cgg atc agc ctc acc aag      1584
Ser Cys Pro Ser Ser Pro Arg Ile Arg Arg Arg Ile Ser Leu Thr Lys
        515                 520                 525 cgt ctc agt gcg aag ctt gcc cga gag aaa agc tca tca cct agt ggg      1632
Arg Leu Ser Ala Lys Leu Ala Arg Glu Lys Ser Ser Ser Pro Ser Gly
    530                 535                 540 agt ccc ggg gac ccc tca tcc ccc acc tcc agt gtg tcc cca ggg tca      1680
Ser Pro Gly Asp Pro Ser Ser Pro Thr Ser Ser Val Ser Pro Gly Ser
545                 550                 555                 560 ccc ccc tca agt cct aga agc aga gat gct cct gct ggc agt ccc ccg      1728
Pro Pro Ser Ser Pro Arg Ser Arg Asp Ala Pro Ala Gly Ser Pro Pro
                565                 570                 575 gcc tct cca ggg ccc cag ggc ccc agc acc aag ctg ccc ctg agc ctg      1776
Ala Ser Pro Gly Pro Gln Gly Pro Ser Thr Lys Leu Pro Leu Ser Leu
            580                 585                 590 gac ctg ccc agc ccc cgg ccc ttc gct ttg cct ctg ggc agc cct cga      1824
Asp Leu Pro Ser Pro Arg Pro Phe Ala Leu Pro Leu Gly Ser Pro Arg
        595                 600                 605 atc ccc ctc ccg gcg cag cag agc tcg gag gcc cgt gtc atc cgc gtc      1872
Ile Pro Leu Pro Ala Gln Gln Ser Ser Glu Ala Arg Val Ile Arg Val
    610                 615                 620 agc atc gac aat gac cac ggg aac ctg tat cga agc atc ttg ctg acc      1920
Ser Ile Asp Asn Asp His Gly Asn Leu Tyr Arg Ser Ile Leu Leu Thr
625                 630                 635                 640 agt cag gac aaa gcc ccc agc gtg gtc cgg cga gcc ttg cag aag cac      1968
Ser Gln Asp Lys Ala Pro Ser Val Val Arg Arg Ala Leu Gln Lys His
                645                 650                 655 aat gtg ccc cag ccc tgg gcc tgt gac tat cag ctc ttt caa gtc ctt      2016
Asn Val Pro Gln Pro Trp Ala Cys Asp Tyr Gln Leu Phe Gln Val Leu
            660                 665                 670 cct ggg gac cgg gtc gcc ccc aga gac ttc atg ctg cgg cgg aaa gag      2064
Pro Gly Asp Arg Val Ala Pro Arg Asp Phe Met Leu Arg Arg Lys Glu
        675                 680                 685 ggg acc cgg aac act ctg tct gtc tcc cca agc tgaggcagcc ctgtcctctc    2117
Gly Thr Arg Asn Thr Leu Ser Val Ser Pro Ser
    690                 695 cacaagacac aagtcccaca ggcaagcttg cgactcttct cctggaaagc tgccatcccc    2177
cagtagaggc cactgtgctg tgtatcccag gaccaccacc caactgtagc ccattggacc    2237
ccatctcttt ttctgactct gttggtacta gatccatatt ccaaagacat cagcccatgg    2297
gtggctggtg gagagctcaa tcccataaat gtagaaagag gtggggcatg gatacgtcaa    2357
atccctcccc agagaaatct tataaatgtt agagacgcat cagaagtgac agatgcggat    2417
gaaaatagtg accagagtta tgaaaaaaaa aaaa                                 2451
```

<210> SEQ ID NO 18
<211> LENGTH: 259

```
<212> TYPE: PRT
<213> ORGANISM: Homo sapiens

<400> SEQUENCE: 18

Met Ser Pro Ala Val Pro Asn Leu Trp Ser Val Asp Gly Glu Val
1               5                   10                  15

Thr Val Ala Glu Gln Lys Pro Gly Glu Ile Ala Glu Leu Ala Ser
                20                  25                  30

Ser Tyr Glu Arg Lys Leu Ile Glu Val Ala Glu Met His Gly Glu Leu
            35                  40                  45

Ile Glu Phe Asn Glu Arg Leu His Arg Ala Leu Val Ala Lys Glu Ala
        50                  55                  60

Leu Val Ser Gln Met Arg Gln Glu Leu Ile Asp Leu Arg Gly Pro Val
65                  70                  75                  80

Pro Gly Asp Leu Ser Gln Thr Ser Glu Asp Gln Ser Leu Ser Asp Phe
                85                  90                  95

Glu Ile Ser Asn Arg Ala Leu Ile Asn Val Trp Ile Pro Ser Val Phe
                100                 105                 110

Leu Arg Gly Lys Ala Ala Asn Ala Phe His Val Tyr Gln Val Tyr Ile
                115                 120                 125

Arg Ile Lys Asp Asp Glu Trp Asn Ile Tyr Arg Arg Tyr Thr Glu Phe
130                 135                 140

Arg Ser Leu His His Lys Leu Gln Asn Lys Tyr Pro Gln Val Arg Ala
145                 150                 155                 160

Tyr Asn Phe Pro Pro Lys Lys Ala Ile Gly Asn Lys Asp Ala Lys Phe
                165                 170                 175

Val Glu Glu Arg Arg Lys Gln Leu Gln Asn Tyr Leu Arg Ser Val Met
                180                 185                 190
Asn Lys Val Ile Gln Met Val Pro Glu Phe Ala Ala Ser Pro Lys Lys
                195                 200                 205

Glu Thr Leu Ile Gln Leu Met Pro Phe Phe Val Asp Ile Thr Pro Pro
                210                 215                 220

Gly Glu Pro Val Asn Ser Arg Pro Lys Ala Ala Ser Arg Phe Pro Lys
225                 230                 235                 240

Leu Ser Arg Gly Gln Pro Arg Glu Thr Arg Asn Val Glu Pro Gln Ser
                245                 250                 255

Gly Asp Leu

<210> SEQ ID NO 19
<211> LENGTH: 847
<212> TYPE: PRT
<213> ORGANISM: Homo sapiens

<400> SEQUENCE: 19

Met Lys Lys Thr Pro Val Phe Leu Glu Ser Leu Val Thr Asn Met Leu
1               5                   10                  15

Arg Leu Arg Ala Ile Cys Pro Phe Ser Trp Arg Val Phe Gln Phe Arg
                20                  25                  30

Pro Ile Ser Cys Glu Pro Leu Ile Ile Gln Met Asn Lys Cys Thr Asp
            35                  40                  45

Glu Glu Gln Met Phe Gly Phe Ile Glu Arg Asn Lys Ala Ile Leu Ser
        50                  55                  60

Glu Lys Gln Val Gly Cys Ala Phe Asp Met Leu Trp Lys Leu Gln Lys
65                  70                  75                  80

Gln Lys Thr Ser Leu Leu Lys Asn Ala Glu Tyr Val Arg Asp His Pro
                85                  90                  95
```

```
Gln Phe Leu Thr Leu His Asn Leu Ala Thr Asn Lys Phe Lys Leu Met
            100                 105                 110
Asn Asp Asp Thr Leu Val Asn Val Leu Tyr Val Thr Gln Gln Phe Ala
        115                 120                 125
Gly Glu Ala His Asp Pro Leu Val Glu Ala Leu Val Thr Glu Ala Trp
    130                 135                 140
Arg Arg Leu Glu Arg Phe Asp Ile Lys Leu Leu Ser Glu Phe Ser Ser
145                 150                 155                 160
Cys Leu Ala Asp Gln His Leu Tyr Phe Ser Pro Leu Met Gly Lys Ile
                165                 170                 175
Ala Asp Ile Val His Arg Asn Leu Glu Thr Thr Gln Asp Leu Ser Ser
            180                 185                 190
Leu Ser Val Leu Met Val Asn Ile Ser Ser Leu Ile Ser Arg His Phe
        195                 200                 205
Gln Gln Gln Leu Val Asn Lys Thr Glu Leu Leu Phe Asp Thr Ile Asp
    210                 215                 220
Ser Ser Glu Val Asn Val Ala Lys Ser Ile Ala Lys Phe Leu Arg Asn
225                 230                 235                 240
Val Arg Tyr Arg Tyr Gln Pro Leu Leu Glu Arg Cys Asn Asn Val Phe
                245                 250                 255
Leu Ser Asn Val Asp His Leu Asp Leu Asp Ser Ile Ser Lys Ile Leu
            260                 265                 270
Ser Val Tyr Lys Phe Leu Gln Phe Asn Ser Phe Glu Phe Ile Ile Met
        275                 280                 285
Ala Lys Lys Lys Leu Thr Glu Met Ile Pro Leu Cys Asn His Pro Ala
    290                 295                 300
Ser Phe Val Lys Leu Phe Val Ala Leu Gly Pro Ile Ala Gly Pro Glu
305                 310                 315                 320
Glu Lys Lys Gln Leu Lys Ser Thr Met Leu Leu Met Ser Glu Asp Leu
                325                 330                 335
Thr Gly Glu Gln Ala Leu Ala Val Leu Gly Ala Met Gly Asp Met Glu
            340                 345                 350
Ser Arg Asn Ser Cys Leu Ile Lys Arg Val Thr Ser Val Leu His Lys
        355                 360                 365
His Leu Asp Gly Tyr Lys Pro Leu Glu Leu Leu Lys Ile Thr Gln Glu
    370                 375                 380
Leu Thr Phe Leu His Phe Gln Arg Lys Glu Phe Phe Ala Lys Leu Arg
385                 390                 395                 400
Glu Leu Leu Leu Ser Tyr Leu Lys Asn Ser Phe Ile Pro Thr Glu Val
                405                 410                 415
Ser Val Leu Val Arg Ala Ile Ser Leu Leu Pro Ser Pro His Leu Asp
            420                 425                 430
Glu Val Gly Ile Ser Arg Ile Glu Ala Val Leu Pro Gln Cys Asp Leu
        435                 440                 445
Asn Asn Leu Ser Ser Phe Ala Thr Ser Val Leu Arg Trp Ile Gln His
    450                 455                 460
Asp His Val Tyr Leu Asp Asn Met Thr Ala Lys Gln Leu Lys Leu Leu
465                 470                 475                 480
Gln Lys Leu Asp His Tyr Gly Arg Gln Arg Leu Gln His Ser Asn Ser
                485                 490                 495
Leu Asp Leu Leu Arg Lys Glu Leu Lys Ser Leu Lys Gly Asn Thr Phe
            500                 505                 510
```

-continued

```
Pro Glu Ser Leu Leu Glu Glu Met Ile Ala Thr Leu Gln His Phe Met
            515                 520                 525
Asp Asp Ile Asn Tyr Ile Asn Val Gly Glu Ile Ala Ser Phe Ile Ser
        530                 535                 540
Ser Thr Asp Tyr Leu Ser Thr Leu Leu Leu Asp Arg Ile Ala Ser Val
545                 550                 555                 560
Ala Val Gln Gln Ile Glu Lys Ile His Pro Phe Thr Ile Pro Ala Ile
                565                 570                 575
Ile Arg Pro Phe Ser Val Leu Asn Tyr Asp Pro Pro Gln Arg Asp Glu
            580                 585                 590
Phe Leu Gly Thr Cys Val Gln His Leu Asn Ser Tyr Leu Gly Ile Leu
            595                 600                 605
Asp Pro Phe Ile Leu Val Phe Leu Gly Phe Ser Leu Ala Thr Leu Glu
        610                 615                 620
Tyr Phe Pro Glu Asp Leu Leu Lys Ala Ile Phe Asn Ile Lys Phe Leu
625                 630                 635                 640
Ala Arg Leu Asp Ser Gln Leu Glu Ile Leu Ser Pro Ser Arg Ser Ala
                645                 650                 655
Arg Val Gln Phe His Leu Met Glu Leu Asn Arg Ser Val Cys Leu Glu
            660                 665                 670
Cys Pro Glu Phe Gln Ile Pro Trp Phe His Asp Arg Phe Cys Gln Gln
            675                 680                 685
Tyr Asn Lys Gly Ile Gly Gly Met Asp Gly Thr Gln Gln Ile Phe
        690                 695                 700
Lys Met Leu Ala Glu Val Leu Gly Gly Ile Asn Cys Val Lys Ala Ser
705                 710                 715                 720
Val Leu Thr Pro Tyr Tyr His Lys Val Asp Phe Glu Cys Ile Leu Asp
                725                 730                 735
Lys Arg Lys Lys Pro Leu Pro Tyr Gly Ser His Asn Ile Ala Leu Gly
            740                 745                 750
Gln Leu Pro Glu Met Pro Trp Glu Ser Asn Ile Glu Ile Val Gly Ser
            755                 760                 765
Arg Leu Pro Pro Gly Ala Glu Arg Ile Ala Leu Glu Phe Leu Asp Ser
770                 775                 780
Lys Ala Leu Cys Arg Asn Ile Pro His Met Lys Gly Lys Ser Ala Met
785                 790                 795                 800
Lys Lys Arg His Leu Glu Ile Leu Gly Tyr Arg Val Ile Gln Ile Ser
                805                 810                 815
Gln Phe Glu Trp Asn Ser Met Ala Leu Ser Thr Lys Asp Ala Arg Met
            820                 825                 830
Asp Tyr Leu Arg Glu Cys Ile Phe Gly Glu Val Lys Ser Cys Leu
            835                 840                 845
```

<210> SEQ ID NO 20
<211> LENGTH: 158
<212> TYPE: PRT
<213> ORGANISM: Homo sapiens

<400> SEQUENCE: 20

```
Met Ile Ala Val Ile Leu Gly Ser Leu Phe Leu Ile Ala Ser Val Thr
1               5                   10                  15
Trp Leu Leu Trp Ser Ala Phe Ser Pro Tyr Ala Val Trp Gln Arg Lys
                20                  25                  30
Asp Ile Leu Phe Gln Ile Cys Tyr Gly Met Tyr Gly Phe Met Asp Leu
            35                  40                  45
```

```
Val Cys Ile Gly Leu Ile Val His Glu Gly Ala Ala Val Tyr Arg Val
     50                  55                  60

Phe Lys Arg Trp Arg Ala Val Asn Leu His Trp Asp Val Leu Asn Tyr
 65                  70                  75                  80

Asp Lys Ala Thr Asp Ile Glu Ser Ser Arg Gly Glu Ser Ser Thr
                 85                  90                  95

Ser Arg Thr Leu Trp Leu Pro Leu Thr Ala Leu Arg Asn Arg Asn Leu
                100                 105                 110

Val His Pro Thr Gln Leu Thr Ser Pro Arg Phe Gln Cys Gly Tyr Val
                115                 120                 125

Leu Leu His Leu Phe Asn Arg Met Arg Pro His Glu Asp Leu Ser Glu
130                 135                 140

Asp Asn Ser Ser Gly Glu Val Val Met Arg Val Thr Ser Val
145                 150                 155
```

<210> SEQ ID NO 21
<211> LENGTH: 215
<212> TYPE: PRT
<213> ORGANISM: Homo sapiens

<400> SEQUENCE: 21

```
Met Pro Pro Arg Arg Ile Ile Val Glu Val Lys Val Leu Asp Val Gln
  1               5                  10                  15

Lys Arg Arg Val Pro Asn Lys His Tyr Val Tyr Ile Ile Arg Val Thr
                 20                  25                  30

Trp Ser Ser Gly Ser Thr Glu Ala Ile Tyr Arg Arg Tyr Ser Lys Phe
                 35                  40                  45

Phe Asp Leu Gln Met Gln Met Leu Asp Lys Phe Pro Met Glu Gly Gly
 50                  55                  60

Gln Lys Asp Pro Lys Gln Arg Ile Ile Pro Phe Leu Pro Gly Lys Ile
 65                  70                  75                  80

Leu Phe Arg Arg Ser His Ile Arg Asp Val Ala Val Lys Arg Leu Ile
                 85                  90                  95

Pro Ile Asp Glu Tyr Cys Lys Ala Leu Ile Gln Leu Pro Pro Tyr Ile
                100                 105                 110

Ser Gln Cys Asp Glu Val Leu Gln Phe Phe Glu Thr Arg Pro Glu Asp
                115                 120                 125

Leu Asn Pro Pro Lys Glu Glu His Ile Gly Lys Lys Ser Gly Gly
130                 135                 140

Asp Gln Thr Ser Val Asp Pro Met Val Leu Glu Gln Tyr Val Val Val
145                 150                 155                 160

Ala Asn Tyr Gln Lys Gln Glu Ser Ser Glu Ile Ser Leu Ser Val Gly
                165                 170                 175

Gln Val Val Asp Ile Ile Glu Lys Thr Glu Ser Gly Trp Trp Phe Val
                180                 185                 190

Ser Thr Ala Glu Glu Gln Gly Trp Val Pro Ala Thr Val Pro Arg Arg
                195                 200                 205

Ala Arg Met Arg Val Gln Gly
        210                 215
```

<210> SEQ ID NO 22
<211> LENGTH: 201
<212> TYPE: PRT
<213> ORGANISM: Homo sapiens

<400> SEQUENCE: 22

```
Met Ala Ser Val Ala Trp Ala Val Leu Lys Val Leu Leu Leu Pro
1               5                   10                  15

Thr Gln Thr Trp Ser Pro Val Gly Ala Gly Asn Pro Pro Asp Cys Asp
            20                  25                  30

Ala Pro Leu Ala Ser Ala Leu Pro Arg Ser Ser Phe Ser Ser Ser Ser
            35                  40                  45

Glu Leu Ser Ser Ser His Gly Pro Gly Phe Ser Arg Leu Asn Arg Arg
    50                  55                  60

Asp Gly Ala Gly Gly Trp Thr Pro Leu Val Ser Asn Lys Tyr Gln Trp
65                  70                  75                  80

Leu Gln Ile Asp Leu Gly Glu Arg Met Glu Val Thr Ala Val Ala Thr
                85                  90                  95

Gln Gly Gly Tyr Gly Ser Ser Asp Trp Val Thr Ser Tyr Leu Leu Met
                100                 105                 110

Phe Ser Asp Gly Gly Arg Asn Trp Lys Gln Tyr Arg Arg Glu Glu Ser
            115                 120                 125

Ile Trp Gly Phe Pro Gly Asn Thr Asn Ala Asp Ser Val Val His Tyr
    130                 135                 140

Arg Leu Gln Pro Pro Phe Glu Ala Arg Phe Leu Arg Phe Leu Pro Leu
145                 150                 155                 160

Ala Trp Glu Pro Pro Gly Ala Gly Leu Gly Cys Gly Leu Lys Cys Thr
                165                 170                 175

Asp Val His Ile Asn Leu Arg Trp Phe Ile Leu Met Asp Lys Val Leu
            180                 185                 190

Cys Cys Ile His Leu Ile Lys Asn Leu
            195                 200

<210> SEQ ID NO 23
<211> LENGTH: 81
<212> TYPE: PRT
<213> ORGANISM: Homo sapiens

<400> SEQUENCE: 23

Met Leu Ser Pro Lys Ile Arg Gln Ala Arg Arg Ala Arg Ser Lys Ser
1               5                   10                  15

Leu Val Met Gly Glu Gln Ser Arg Ser Pro Gly Arg Met Pro Cys Pro
            20                  25                  30

His Arg Leu Gly Pro Val Leu Lys Ala Gly Trp Leu Lys Lys Gln Arg
            35                  40                  45

Ser Ile Met Lys Asn Trp Gln Gln Arg Trp Phe Val Leu Arg Gly Asp
    50                  55                  60

Gln Leu Phe Tyr Tyr Lys Asp Lys Asp Glu Ile Lys Pro Gln Glu Asn
65                  70                  75                  80

Lys

<210> SEQ ID NO 24
<211> LENGTH: 456
<212> TYPE: PRT
<213> ORGANISM: Homo sapiens

<400> SEQUENCE: 24

Met Glu Thr Thr Val Ser Arg Pro Val Leu Ser Pro Thr His Ile Asn
1               5                   10                  15

Ala Thr Ala Ser Glu Thr Phe Val Leu Gln Gln Arg Met Arg Ile
            20                  25                  30

Val Glu Glu Gln Thr Ser Ser Leu Arg Asp Asp Leu Ile Met Leu Asp
```

```
            35                  40                  45
Phe Gly Glu Lys Arg Ser His Val Asn Ser Ile Lys Glu Arg Thr Ser
        50                  55                  60

Ser Val Gly Leu Pro Ser Val Ile Pro Asn Ser Thr Arg Arg Val Ser
 65                  70                  75                  80

Phe Ala Pro Asn Leu Pro Ser Met Lys Thr Ser Gln Asp Ile Gly Asp
                85                  90                  95

Ser Arg Ile Ser Leu Lys Thr Leu Leu Asn Ala Ile Lys Thr Met Glu
            100                 105                 110

Gly Arg Leu Glu Gly Lys Ile Glu Ile Leu Ala Ser Arg Pro Leu Ile
            115                 120                 125

Asn Asp Glu Ser Pro Asn Phe Leu Lys Gln Asp Ser Val Lys Ser Ile
130                 135                 140

Leu Glu Arg Ser Lys Glu Glu Leu Ser Arg Thr Val Lys Cys Arg Asn
145                 150                 155                 160

Ala Ala Leu Lys Glu Ser Gln Lys Leu Lys Glu Asp Leu Glu Ala Val
                165                 170                 175

Glu Asp Arg Glu Asn Lys Lys Ala Arg Asn Gln Ser Leu Leu Thr Val
            180                 185                 190

Gly Asn Phe Gln Arg Gln Leu Ala Glu Ala Lys Glu Asp Asn Cys Lys
            195                 200                 205

Val Thr Ile Met Leu Glu Asn Val Leu Ala Ser His Ser Lys Met Gln
210                 215                 220

Gly Ala Leu Glu Lys Val Gln Ile Glu Leu Gly Arg Arg Asp Ser Glu
225                 230                 235                 240

Ile Ala Gly Leu Lys Lys Glu Arg Asp Leu Asn Gln Gln Arg Val Gln
                245                 250                 255

Lys Leu Glu Ala Glu Val Asp Gln Trp Gln Ala Arg Met Leu Val Met
            260                 265                 270

Glu Asp Gln His Asn Ser Glu Ile Glu Ser Leu Gln Lys Ala Leu Gly
            275                 280                 285

Val Ala Arg Glu Asp Asn Arg Lys Leu Ala Met Ser Leu Glu Gln Ala
290                 295                 300

Leu Gln Thr Asn Asn His Leu Gln Thr Lys Leu Asp His Ile Gln Glu
305                 310                 315                 320

Gln Leu Glu Ser Lys Glu Leu Glu Arg Gln Asn Leu Glu Thr Phe Lys
                325                 330                 335

Asp Arg Met Thr Glu Glu Ser Lys Val Glu Ala Glu Leu His Ala Glu
            340                 345                 350

Arg Ile Glu Ala Leu Arg Lys Gln Phe Gln Thr Glu Arg Glu Thr Thr
            355                 360                 365

Lys Lys Val Ala Gln Arg Glu Val Ala Glu Leu Lys Lys Ala Leu Asp
370                 375                 380

Glu Ala Asn Phe Arg Ser Val Glu Val Ser Arg Thr Asn Arg Glu Leu
385                 390                 395                 400

Arg Gln Lys Leu Ala Glu Leu Glu Lys Ile Leu Glu Ser Asn Lys Glu
                405                 410                 415

Lys Ile Lys Asn Gln Lys Thr Gln Ile Lys Leu His Leu Ser Ala Lys
            420                 425                 430

Ala Asn Asn Ala Gln Asn Ile Glu Arg Met Lys Val Val Trp Glu Thr
            435                 440                 445

Ser Ser His Phe Leu Asp Thr Leu
450                 455
```

```
<210> SEQ ID NO 25
<211> LENGTH: 1381
<212> TYPE: PRT
<213> ORGANISM: Homo sapiens

<400> SEQUENCE: 25

Met Gly Ile Lys Pro Ala Ser Phe Asn Lys Val Thr Asp Pro Glu Val
1               5                   10                  15

Lys Glu Ile Ile Glu Gly Cys Ile Arg Gln Asn Lys Ser Glu Arg Leu
            20                  25                  30

Ser Ile Arg Asp Leu Leu Asn His Ala Phe Phe Ala Glu Asp Thr Gly
        35                  40                  45

Leu Arg Val Glu Leu Ala Glu Glu Asp Asp Cys Ser Asn Ser Ser Leu
50                  55                  60

Ala Leu Arg Leu Trp Val Glu Asp Pro Lys Lys Leu Lys Gly Lys His
65                  70                  75                  80

Lys Asp Asn Glu Ala Ile Glu Phe Ser Phe Asn Leu Glu Thr Asp Thr
                85                  90                  95

Pro Glu Glu Val Ala Tyr Glu Met Val Lys Ser Gly Phe Phe His Glu
            100                 105                 110

Ser Asp Ser Lys Ala Val Ala Lys Ser Ile Arg Asp Arg Val Thr Pro
        115                 120                 125

Ile Lys Lys Thr Arg Glu Lys Lys Pro Ala Gly Cys Leu Glu Glu Arg
130                 135                 140

Arg Asp Ser Gln Cys Lys Ser Met Gly Asn Val Phe Pro Gln Pro Gln
145                 150                 155                 160

Asn Thr Thr Leu Pro Leu Ala Pro Ala Gln Gln Thr Gly Ala Glu Cys
                165                 170                 175

Glu Glu Thr Glu Val Asp Gln His Val Arg Gln Gln Leu Leu Gln Arg
            180                 185                 190

Lys Pro Gln Gln His Cys Ser Ser Val Thr Gly Asp Asn Leu Ser Glu
        195                 200                 205

Ala Gly Ala Ala Ser Val Ile His Ser Asp Thr Ser Ser Gln Pro Ser
210                 215                 220

Val Ala Tyr Ser Ser Asn Gln Thr Met Gly Ser Gln Met Val Ser Asn
225                 230                 235                 240

Ile Pro Gln Ala Glu Val Asn Val Pro Gly Gln Ile Tyr Ser Ser Gln
                245                 250                 255

Gln Leu Val Gly His Tyr Gln Gln Val Ser Gly Leu Gln Lys His Ser
            260                 265                 270

Lys Leu Thr Gln Pro Gln Ile Leu Pro Leu Val Gln Gly Gln Ser Thr
        275                 280                 285

Val Leu Pro Val His Val Leu Gly Pro Thr Val Ser Gln Pro Gln
290                 295                 300

Val Ser Pro Leu Thr Val Gln Lys Val Pro Gln Ile Lys Pro Val Ser
305                 310                 315                 320

Gln Pro Val Gly Ala Glu Gln Ala Ala Leu Leu Lys Pro Asp Leu
                325                 330                 335

Val Arg Ser Leu Asn Gln Asp Val Ala Thr Thr Lys Glu Asn Val Ser
            340                 345                 350

Ser Pro Asp Asn Pro Ser Gly Asn Gly Lys Gln Asp Arg Ile Lys Gln
        355                 360                 365

Arg Arg Ala Ser Cys Pro Arg Pro Glu Lys Gly Thr Lys Phe Gln Leu
```

```
                370              375              380
    Thr Val Leu Gln Val Ser Thr Ser Gly Asp Asn Met Val Glu Cys Gln
    385              390              395              400
    Leu Glu Thr His Asn Asn Lys Met Val Thr Phe Lys Phe Asp Val Asp
                     405              410              415
    Gly Asp Ala Pro Glu Asp Ile Ala Asp Tyr Met Val Glu Asp Asn Phe
                 420              425              430
    Val Leu Glu Ser Glu Lys Glu Lys Phe Val Glu Leu Arg Ala Ile
                 435              440              445
    Val Gly Gln Ala Gln Glu Ile Leu His Val His Phe Ala Thr Glu Arg
                 450              455              460
    Ala Thr Gly Val Asp Ser Ile Thr Val Asp Ser Asn Ser Ser Gln Thr
    465              470              475              480
    Gly Ser Ser Glu Gln Val Gln Ile Asn Ser Thr Ser Thr Gln Thr Ser
                     485              490              495
    Asn Glu Ser Ala Pro Gln Ser Pro Val Gly Arg Trp Arg Phe Cys
                 500              505              510
    Ile Asn Gln Thr Ile Arg Asn Arg Glu Thr Gln Ser Pro Pro Ser Leu
                 515              520              525
    Gln His Ser Met Ser Ala Val Pro Gly Arg His Pro Leu Pro Ser Pro
        530              535              540
    Lys Asn Thr Ser Asn Lys Glu Ile Ser Arg Asp Thr Leu Leu Thr Ile
    545              550              555              560
    Glu Asn Asn Pro Cys His Arg Ala Leu Phe Thr Ser Lys Ser Glu His
                     565              570              575
    Lys Asp Val Val Asp Gly Lys Ile Ser Glu Cys Ala Ser Val Glu Thr
                 580              585              590
    Lys Gln Pro Ala Ile Leu Tyr Gln Val Glu Asp Asn Arg Gln Ile Met
        595              600              605
    Ala Pro Val Thr Asn Ser Ser Ser Tyr Ser Thr Thr Ser Val Arg Ala
        610              615              620
    Val Pro Ala Glu Cys Glu Gly Leu Thr Lys Gln Ala Ser Ile Phe Ile
    625              630              635              640
    Pro Val Tyr Pro Cys His Gln Thr Ala Ser Gln Ala Asp Ala Leu Met
                     645              650              655
    Ser His Pro Gly Glu Ser Thr Gln Thr Ser Gly Asn Ser Leu Thr Thr
                 660              665              670
    Leu Ala Phe Asp Gln Lys Pro Gln Thr Leu Ser Val Gln Gln Pro Ala
                 675              680              685
    Met Asp Ala Glu Phe Ile Ser Gln Glu Gly Thr Thr Val Asn Thr
        690              695              700
    Glu Ala Ser Ser Pro Lys Thr Val Ile Pro Thr Gln Thr Pro Gly Leu
    705              710              715              720
    Glu Pro Thr Thr Leu Gln Pro Thr Thr Val Leu Glu Ser Asp Gly Glu
                     725              730              735
    Arg Pro Pro Lys Leu Glu Phe Ala Asp Asn Arg Ile Lys Thr Leu Asp
                 740              745              750
    Glu Lys Leu Arg Asn Leu Leu Tyr Gln Glu His Ser Ile Ser Ser Ile
                 755              760              765
    Tyr Pro Glu Ser Gln Lys Asp Thr Gln Ser Ile Asp Ser Pro Phe Ser
        770              775              780
    Ser Ser Ala Glu Asp Thr Leu Ser Cys Pro Val Thr Glu Val Ile Ala
    785              790              795              800
```

-continued

```
Ile Ser His Cys Gly Ile Lys Asp Ser Pro Val Gln Ser Pro Asn Phe
            805                 810                 815
Gln Gln Thr Gly Ser Lys Leu Leu Ser Asn Val Ala Ala Ser Gln Pro
        820                 825                 830
Ala Asn Ile Ser Val Phe Lys Arg Asp Leu Asn Val Ile Thr Ser Val
        835                 840                 845
Ser Ser Glu Leu Cys Leu His Glu Met Ser Ser Asp Ala Ser Leu Pro
850                 855                 860
Gly Asp Pro Glu Ala Tyr Pro Ala Ala Val Ser Ser Gly Gly Ala Ile
865                 870                 875                 880
His Leu Gln Thr Gly Val Glu Thr Glu Met Arg Ser Ala Ile Ala
            885                 890                 895
Pro Asp Pro Ile Pro Leu Thr Arg Glu Ser Thr Ala Asp Thr Arg Ala
                900                 905                 910
Leu Asn Arg Cys Lys Ala Met Ser Gly Ser Phe Gln Arg Gly Arg Phe
            915                 920                 925
Gln Val Ile Thr Ile Pro Gln Gln Gln Ser Ala Lys Met Thr Ser Phe
        930                 935                 940
Gly Ile Glu His Ile Ser Val Phe Ser Glu Thr Asn His Ser Ser Glu
945                 950                 955                 960
Glu Ala Phe Ile Lys Thr Ala Lys Ser Gln Leu Val Glu Ile Glu Pro
                965                 970                 975
Ala Thr Gln Asn Pro Lys Thr Ser Phe Ser Tyr Glu Lys Leu Gln Ala
            980                 985                 990
Leu Gln Glu Thr Cys Lys Glu Asn Lys Gly Val Pro Lys Gln Gly Asp
        995                 1000                1005
Asn Phe Leu Ser Phe Ser Ala Ala Cys Glu Thr Asp Val Ser Ser
    1010                1015                1020
Val Thr Pro Glu Lys Glu Phe Glu Glu Thr Ser Ala Thr Gly Ser
    1025                1030                1035
Ser Met Gln Ser Gly Ser Glu Leu Leu Leu Lys Glu Arg Glu Ile
    1040                1045                1050
Leu Thr Ala Gly Lys Gln Pro Ser Ser Asp Ser Glu Phe Ser Ala
    1055                1060                1065
Ser Leu Ala Gly Ser Gly Lys Ser Val Ala Lys Thr Gly Pro Glu
    1070                1075                1080
Ser Asn Gln Cys Leu Pro His His Glu Glu Gln Ala Tyr Ala Gln
    1085                1090                1095
Thr Gln Ser Ser Leu Phe Tyr Ser Pro Ser Ser Pro Met Ser Ser
    1100                1105                1110
Asp Asp Glu Ser Glu Ile Glu Asp Glu Asp Leu Lys Val Glu Leu
    1115                1120                1125
Gln Arg Leu Arg Glu Lys His Ile Gln Glu Val Val Asn Leu Gln
    1130                1135                1140
Thr Gln Gln Asn Lys Glu Leu Gln Glu Leu Tyr Glu Arg Leu Arg
    1145                1150                1155
Ser Ile Lys Asp Ser Lys Thr Gln Ser Thr Glu Ile Pro Leu Pro
    1160                1165                1170
Pro Ala Ser Pro Arg Arg Pro Arg Ser Phe Lys Ser Lys Leu Arg
    1175                1180                1185
Ser Arg Pro Gln Ser Leu Thr His Val Asp Asn Gly Ile Val Ala
    1190                1195                1200
```

```
Thr Asp Pro Leu Cys Val Glu Ser Asn Ala Ala Ser Cys Gln Gln
    1205                1210                1215

Ser Pro Ala Ser Lys Lys Gly Met Phe Thr Asp Asp Leu His Lys
    1220                1225                1230

Leu Val Asp Asp Trp Thr Lys Glu Ala Val Gly Asn Ser Leu Ile
    1235                1240                1245

Lys Pro Ser Leu Asn Gln Leu Lys Gln Ser Gln His Lys Leu Glu
    1250                1255                1260

Thr Glu Asn Trp Asn Lys Val Ser Glu Asn Thr Pro Ser Thr Met
    1265                1270                1275

Gly Tyr Thr Ser Thr Trp Ile Ser Ser Leu Ser Gln Ile Arg Gly
    1280                1285                1290

Ala Val Pro Thr Ser Leu Pro Gln Gly Leu Ser Leu Pro Ser Phe
    1295                1300                1305

Pro Gly Pro Leu Ser Ser Tyr Gly Met Pro His Val Cys Gln Tyr
    1310                1315                1320

Asn Ala Val Ala Gly Ala Gly Tyr Pro Val Gln Trp Val Gly Ile
    1325                1330                1335

Ser Gly Thr Thr Gln Gln Ser Val Val Ile Pro Ala Gln Ser Gly
    1340                1345                1350

Gly Pro Phe Gln Pro Gly Met Asn Met Gln Ala Phe Pro Thr Ser
    1355                1360                1365

Ser Val Gln Asn Pro Ala Thr Ile Pro Pro Gly Pro Lys
    1370                1375                1380

<210> SEQ ID NO 26
<211> LENGTH: 220
<212> TYPE: PRT
<213> ORGANISM: Homo sapiens
<220> FEATURE:
<221> NAME/KEY: misc_feature
<222> LOCATION: (1)..(1567)
<223> OTHER INFORMATION: n = a, t, c, or g

<400> SEQUENCE: 26

Met Ile Ala Gly Gln Val Leu Asp Ile Asn Leu Ala Ala Glu Pro Lys
1               5                   10                  15

Val Asn Arg Gly Lys Ala Gly Val Lys Arg Ser Ala Ala Glu Met Tyr
                20                  25                  30

Gly Ser Ser Phe Asp Leu Asp Tyr Asp Phe Gln Arg Asp Tyr Tyr Asp
            35                  40                  45

Arg Met Tyr Ser Tyr Pro Ala Arg Val Pro Pro Pro Pro Ile Ala
    50                  55                  60

Arg Ala Val Val Pro Ser Lys Arg Gln Arg Val Ser Gly Asn Thr Ser
65                  70                  75                  80

Arg Arg Gly Lys Ser Gly Phe Asn Ser Lys Ser Gly Gln Arg Gly Ser
                85                  90                  95

Ser Lys Ser Gly Lys Leu Lys Gly Asp Asp Leu Gln Ala Ile Lys Lys
            100                 105                 110

Glu Leu Thr Gln Ile Lys Gln Lys Val Asp Ser Leu Leu Glu Asn Leu
        115                 120                 125

Glu Lys Ile Glu Lys Glu Gln Ser Lys Gln Ala Val Glu Met Lys Asn
    130                 135                 140

Asp Lys Ser Glu Glu Glu Gln Ser Ser Ser Val Lys Lys Asp Glu
145                 150                 155                 160

Thr Asn Val Lys Met Glu Ser Glu Gly Gly Ala Asp Asp Ser Ala Glu
```

```
                       165                 170                  175
Glu Gly Asp Leu Leu Asp Asp Asp Asn Glu Asp Arg Gly Asp Asp
                180                 185                  190

Gln Leu Glu Leu Ile Lys Asp Asp Glu Lys Glu Ala Glu Glu Gly Glu
        195                 200                 205

Asp Asp Arg Asp Ser Ala Asn Gly Glu Asp Asp Ser
        210                 215                 220

<210> SEQ ID NO 27
<211> LENGTH: 743
<212> TYPE: PRT
<213> ORGANISM: Homo sapiens

<400> SEQUENCE: 27

Met Ala Val Ala Ser Ile Leu Gln Ser Leu Gln Pro Leu Pro Ala Gly
1               5                   10                  15

Met Ser Pro Phe Phe Leu Thr Ala Lys Glu Val Ser Tyr Leu Tyr Val
            20                  25                  30

Asn Thr Ala Asp Leu His Ser Gly Pro Ser Phe Val Glu Ser Leu Phe
        35                  40                  45

Glu Glu Phe Asp Cys Asp Leu Ser Asp Leu Arg Asp Met Pro Glu Asp
    50                  55                  60

Asp Gly Glu Pro Ser Lys Gly Ala Ser Pro Glu Leu Ala Lys Ser Pro
65                  70                  75                  80

Arg Leu Arg Asn Ala Ala Asp Leu Pro Pro Leu Pro Asn Lys Pro
                85                  90                  95

Pro Pro Glu Asp Tyr Tyr Glu Glu Ala Leu Pro Leu Gly Pro Gly Lys
            100                 105                 110

Ser Pro Glu Tyr Ile Ser Ser His Asn Gly Cys Ser Pro Ser His Ser
        115                 120                 125

Ile Val Asp Gly Tyr Tyr Glu Asp Ala Asp Ser Ser Tyr Pro Ala Thr
        130                 135                 140

Arg Val Asn Gly Glu Leu Lys Ser Ser Tyr Asn Asp Ser Asp Ala Met
145                 150                 155                 160

Ser Ser Ser Tyr Glu Ser Tyr Asp Glu Glu Glu Glu Gly Lys Ser
                165                 170                 175

Pro Gln Pro Arg His Gln Trp Pro Ser Glu Glu Ala Ser Met His Leu
            180                 185                 190

Val Arg Glu Cys Arg Ile Cys Ala Phe Leu Leu Arg Lys Lys Arg Phe
        195                 200                 205

Gly Gln Trp Ala Lys Gln Leu Thr Val Ile Arg Glu Asp Gln Leu Leu
    210                 215                 220

Cys Tyr Lys Ser Ser Lys Asp Arg Gln Pro His Leu Arg Leu Ala Leu
225                 230                 235                 240

Asp Thr Cys Ser Ile Ile Tyr Val Pro Lys Asp Ser Arg His Lys Arg
                245                 250                 255

His Glu Leu Arg Phe Thr Gln Gly Ala Thr Glu Val Leu Val Leu Ala
            260                 265                 270

Leu Gln Ser Arg Glu Gln Ala Glu Glu Trp Leu Lys Val Ile Arg Glu
        275                 280                 285

Val Ser Lys Pro Val Gly Gly Ala Glu Gly Val Glu Val Pro Arg Ser
    290                 295                 300

Pro Val Leu Leu Cys Lys Leu Asp Leu Asp Lys Arg Leu Ser Gln Glu
305                 310                 315                 320
```

-continued

```
Lys Gln Thr Ser Asp Ser Asp Ser Val Gly Val Gly Asp Asn Cys Ser
                325                 330                 335
Thr Leu Gly Arg Arg Glu Thr Cys Asp His Gly Lys Gly Lys Lys Ser
            340                 345                 350
Ser Leu Ala Glu Leu Lys Gly Ser Met Ser Arg Ala Ala Gly Arg Lys
        355                 360                 365
Ile Thr Arg Ile Ile Gly Phe Ser Lys Lys Thr Leu Ala Asp Asp
    370                 375                 380
Leu Gln Thr Ser Ser Thr Glu Glu Val Pro Cys Cys Gly Tyr Leu
385                 390                 395                 400
Asn Val Leu Val Asn Gln Gly Trp Lys Glu Arg Trp Cys Arg Leu Lys
                405                 410                 415
Cys Asn Thr Leu Tyr Phe His Lys Asp His Met Asp Leu Arg Thr His
            420                 425                 430
Val Asn Ala Ile Ala Leu Gln Gly Cys Glu Val Ala Pro Gly Phe Gly
        435                 440                 445
Pro Arg His Pro Phe Ala Phe Arg Ile Leu Arg Asn Arg Gln Glu Val
    450                 455                 460
Ala Ile Leu Glu Ala Ser Cys Ser Glu Asp Met Gly Arg Trp Leu Gly
465                 470                 475                 480
Leu Leu Leu Val Glu Met Gly Ser Arg Val Thr Pro Glu Ala Leu His
                485                 490                 495
Tyr Asp Tyr Val Asp Val Glu Thr Leu Thr Ser Ile Val Ser Ala Gly
            500                 505                 510
Arg Asn Ser Phe Leu Tyr Ala Arg Ser Cys Gln Asn Gln Trp Pro Glu
        515                 520                 525
Pro Arg Val Tyr Asp Asp Val Pro Tyr Glu Lys Met Gln Asp Glu Glu
    530                 535                 540
Pro Glu Arg Pro Thr Gly Ala Gln Val Lys Arg His Ala Ser Ser Cys
545                 550                 555                 560
Ser Glu Lys Ser His Arg Val Asp Pro Gln Val Lys Val Lys Arg His
                565                 570                 575
Ala Ser Ser Ala Asn Gln Tyr Lys Tyr Gly Lys Asn Arg Ala Glu Glu
            580                 585                 590
Asp Ala Arg Arg Tyr Leu Val Glu Lys Glu Lys Leu Glu Lys Glu Lys
        595                 600                 605
Glu Thr Ile Arg Thr Glu Leu Ile Ala Leu Arg Gln Glu Lys Arg Glu
    610                 615                 620
Leu Lys Glu Ala Ile Arg Ser Ser Pro Gly Ala Lys Leu Lys Ala Leu
625                 630                 635                 640
Glu Glu Ala Val Ala Thr Leu Glu Ala Gln Cys Arg Ala Lys Glu Glu
                645                 650                 655
Arg Arg Ile Asp Leu Glu Leu Lys Leu Val Ala Val Lys Glu Arg Leu
            660                 665                 670
Gln Gln Ser Leu Ala Gly Gly Pro Ala Leu Gly Leu Ser Val Ser Ser
        675                 680                 685
Lys Pro Lys Ser Gly Glu Thr Ala Asn Lys Pro Gln Asn Ser Val Pro
    690                 695                 700
Glu Gln Pro Leu Pro Val Asn Cys Val Ser Leu Arg Lys Arg Ser
705                 710                 715                 720
Pro Ser Ile Val Ala Ser Asn Gln Gly Arg Val Leu Gln Lys Ala Lys
                725                 730                 735
Glu Trp Glu Met Lys Lys Thr
```

740

<210> SEQ ID NO 28
<211> LENGTH: 239
<212> TYPE: PRT
<213> ORGANISM: Homo sapiens

<400> SEQUENCE: 28

Met Pro Pro Ser Pro Phe Glu Ser Ser Arg Ala Thr Pro Val Thr
1               5                   10                  15

Cys Asn Leu Cys Pro Glu Ile Ile Thr Met Ala Arg Val Ala Ser Ala
                20                  25                  30

Gln Gly Leu Cys Asp Ile Thr Lys Gly Leu Ala Pro Gly Ala Gln Ser
            35                  40                  45

Ser Ser Cys Glu Gly Lys Gln Thr Arg His Glu Gln Leu Pro Ser Pro
50                  55                  60

Ser Leu Leu Thr Met Trp Thr Leu Lys Ser Ser Leu Val Leu Leu Leu
65                  70                  75                  80

Cys Leu Thr Cys Ser Tyr Ala Phe Met Phe Ser Ser Leu Arg Gln Lys
                85                  90                  95

Thr Ser Glu Pro Gln Gly Lys Val Gln Tyr Gly Glu His Phe Arg Ile
                100                 105                 110

Arg Gln Asn Leu Pro Glu His Thr Gln Gly Trp Leu Gly Ser Lys Trp
            115                 120                 125

Leu Trp Leu Leu Phe Val Val Pro Phe Val Ile Leu Gln Cys Gln
    130                 135                 140

Arg Asp Ser Glu Lys Asn Lys Glu Gln Ser Pro Pro Gly Leu Arg Gly
145                 150                 155                 160

Gly Gln Leu His Ser Pro Leu Lys Lys Arg Asn Ala Ser Pro Asn
                165                 170                 175

Lys Asp Cys Ala Phe Asn Thr Leu Met Glu Leu Glu Val Glu Leu Met
            180                 185                 190

Lys Phe Val Ser Lys Val Arg Asn Leu Lys Arg Ala Met Ala Thr Gly
            195                 200                 205

Ser Gly Ser Asn Leu Arg Leu Arg Lys Ser Glu Met Pro Ala Asp Pro
    210                 215                 220

Tyr His Val Thr Ile Cys Glu Ile Trp Gly Glu Ser Ser Ser
225                 230                 235

<210> SEQ ID NO 29
<211> LENGTH: 244
<212> TYPE: PRT
<213> ORGANISM: Homo sapiens

<400> SEQUENCE: 29

Met Ala Leu Val Thr Leu Gln Arg Ser Pro Thr Pro Ser Ala Ala Ser
1               5                   10                  15

Ser Ser Ala Ser Asn Ser Glu Leu Glu Ala Gly Ser Glu Glu Asp Arg
                20                  25                  30

Lys Leu Asn Leu Ser Leu Ser Glu Ser Phe Phe Met Val Lys Gly Ala
            35                  40                  45

Ala Leu Phe Leu Gln Gln Gly Ser Ser Pro Gln Gly Gln Arg Ser Leu
        50                  55                  60

Gln His Pro His Lys His Ala Gly Asp Leu Pro Gln His Leu Gln Val
65                  70                  75                  80

Met Ile Asn Leu Leu Arg Cys Glu Asp Arg Ile Lys Leu Ala Val Arg

```
                85                  90                  95
Leu Glu Ser Ala Trp Ala Asp Arg Val Arg Tyr Met Val Val Tyr
            100                 105                 110
Ser Ser Gly Arg Gln Asp Thr Glu Glu Asn Ile Leu Leu Gly Val Asp
            115                 120                 125
Phe Ser Ser Lys Glu Ser Lys Ser Cys Thr Ile Gly Met Val Leu Arg
            130                 135                 140
Leu Trp Ser Asp Thr Lys Ile His Leu Asp Gly Asp Gly Phe Ser
145                 150                 155                 160
Val Ser Thr Ala Gly Arg Met His Ile Phe Lys Pro Val Ser Val Gln
                165                 170                 175
Ala Met Trp Ser Ala Leu Gln Val Leu His Lys Ala Cys Glu Val Ala
            180                 185                 190
Arg Arg His Asn Tyr Phe Pro Gly Gly Val Ala Leu Ile Trp Ala Thr
            195                 200                 205
Tyr Tyr Glu Ser Cys Ile Ser Ser Glu Gln Ser Cys Ile Asn Glu Trp
            210                 215                 220
Asn Ala Met Gln Asp Leu Glu Ser Thr Arg Pro Asp Ser Pro Ala Leu
225                 230                 235                 240
Phe Val Asp Lys

<210> SEQ ID NO 30
<211> LENGTH: 254
<212> TYPE: PRT
<213> ORGANISM: Homo sapiens

<400> SEQUENCE: 30

Met Gln Ser Asn Met Thr Asn Thr Val Val Arg Thr Thr Leu Arg Asn
1               5                   10                  15
Asp Leu Ser Gln Glu Gly Ile Ile His His Leu Lys Ile Leu Ser Pro
            20                  25                  30
Ile Tyr Cys Ala Phe Gln Asn Asp Leu Leu Thr Ser Ser Gly Phe Thr
            35                  40                  45
Leu Glu Trp Gly Val Tyr Thr Ile Ile Glu Asp Leu His Gly Ala Gly
        50                  55                  60
Asn Phe Val Thr Glu Met Gln Leu Phe Ile Gly Asp Ser Pro Ile Pro
65                  70                  75                  80
Gln Asn Tyr Ser Val Ser Ala Ser Asp Asp Val Arg Ile Glu Val Gly
                85                  90                  95
Leu Tyr Arg Gln Lys Ser Asn Leu Lys Val Val Leu Thr Glu Cys Trp
            100                 105                 110
Ala Thr Pro Ser Ser Asn Ala Arg Asp Pro Ile Thr Phe Ser Phe Ile
            115                 120                 125
Asn Asn Ser Cys Pro Val Pro Asn Thr Tyr Thr Asn Val Ile Glu Asn
130                 135                 140
Gly Asn Ser Asn Lys Ala Gln Phe Lys Leu Arg Ile Phe Ser Phe Ile
145                 150                 155                 160
Asn Asp Ser Ile Val Tyr Leu His Cys Lys Leu Arg Val Cys Met Glu
                165                 170                 175
Ser Pro Gly Ala Thr Cys Lys Ile Ile Ser His Leu Cys Leu Ser Pro
            180                 185                 190
Pro Arg Gly Glu Pro Pro His Ala Glu Ala Gly Leu Gly Ala Gly Tyr
        195                 200                 205
Val Val Leu Ile Val Val Ala Ile Phe Val Leu Val Ala Gly Thr Ala
```

```
            210                 215                 220
Thr Leu Leu Ile Val Arg Tyr Gln Arg Met Asn Gly Arg Tyr Asn Phe
225                 230                 235                 240

Lys Ile Gln Ser Asn Asn Phe Ser Tyr Gln Val Phe Tyr Glu
                245                 250

<210> SEQ ID NO 31
<211> LENGTH: 274
<212> TYPE: PRT
<213> ORGANISM: Homo sapiens

<400> SEQUENCE: 31

Met Lys Leu Pro Lys Gly Thr Arg Ser Ser Val Tyr Phe Ala Gln His
1               5                   10                  15

Pro Glu Lys Glu Pro Leu Pro Ser Arg Gln Glu Val Lys Gln Thr Pro
                20                  25                  30

Val Ile Met Ala Lys Ile Lys Gly Pro Gly Pro Ala Lys Tyr Leu Arg
            35                  40                  45

Pro Ser Cys Thr Gly Tyr Ile Asp His Asp Ile Ser Met Phe Lys Ala
        50                  55                  60

Pro Ala Tyr Thr Leu His Ser Arg His Ser Glu Lys Arg Met Val Cys
65                  70                  75                  80

His Ser Ser Pro Gly Pro Cys Tyr Leu Leu Asp Pro Lys Ile Thr Arg
                85                  90                  95

Phe Gly Met Ser Ser Cys Pro Gln Val Pro Met Glu Glu Arg Ile Ser
            100                 105                 110

Asn Leu Arg Leu Asn Pro Thr Leu Ala Ser Cys Gln Tyr Tyr Phe Glu
        115                 120                 125

Lys Ile His Pro Pro Gly Glu Arg Arg Ala Pro Gln Tyr Thr Phe Gly
    130                 135                 140

Tyr Arg Arg Pro Tyr Arg Val Met Asp Leu Asn Pro Ala Pro Asn Gln
145                 150                 155                 160

Tyr Gln Met Pro Leu Leu Leu Gly Pro Asn Thr Pro Val Ser Arg Ala
                165                 170                 175

Ala Pro Cys Tyr Ser Leu Ala Ser Arg Asp Lys Asn Trp Phe Tyr Lys
            180                 185                 190

Glu Asp Val Ala Gly Gly Pro Gly Pro Thr Thr Tyr Ala Arg Pro Glu
        195                 200                 205

Pro Ser Ile Tyr Gln Asn Arg Ser Pro Thr Tyr Ser Met Ala Lys Arg
    210                 215                 220

Phe Ala Tyr Pro Leu Asp Leu Thr Pro Arg Pro Gly Pro Gly Ser His
225                 230                 235                 240

Glu Val Gln Gln Val Thr Val His Lys Pro His Ile Pro Ala Phe Thr
                245                 250                 255

Met Gly Ile Lys His Ser Leu His Leu Cys Pro Leu Val Ile Asp Ile
            260                 265                 270

Arg Asp

<210> SEQ ID NO 32
<211> LENGTH: 346
<212> TYPE: PRT
<213> ORGANISM: Homo sapiens

<400> SEQUENCE: 32

Met Val Ala Glu Trp Gln Cys Val Gly Phe Cys His Gly Val Leu Asn
1               5                   10                  15
```

-continued

```
Thr Asp Asn Met Ser Ile Leu Gly Leu Thr Ile Asp Tyr Gly Pro Phe
             20                  25                  30

Gly Phe Leu Asp Arg Tyr Asp Pro Asp His Val Cys Asn Ala Ser Asp
         35                  40                  45

Asn Thr Gly Arg Tyr Ala Tyr Ser Lys Gln Pro Glu Val Cys Arg Trp
     50                  55                  60

Asn Leu Arg Lys Leu Ala Glu Ala Leu Gln Pro Glu Leu Pro Leu Glu
 65                  70                  75                  80

Leu Gly Glu Ala Ile Leu Ala Glu Glu Phe Asp Ala Glu Phe Gln Arg
                 85                  90                  95

His Tyr Leu Gln Lys Met Arg Arg Lys Leu Gly Leu Val Gln Val Glu
             100                 105                 110

Leu Glu Glu Asp Gly Ala Leu Val Ser Lys Leu Leu Glu Thr Met His
         115                 120                 125

Leu Thr Gly Ala Asp Phe Thr Asn Thr Phe Tyr Leu Ser Ser Phe
     130                 135                 140

Pro Val Glu Leu Glu Ser Pro Gly Leu Ala Glu Phe Leu Ala Arg Leu
145                 150                 155                 160

Met Glu Gln Cys Ala Ser Leu Glu Glu Leu Arg Leu Ala Phe Arg Pro
                 165                 170                 175

Gln Met Asp Pro Arg Gln Leu Ser Met Met Leu Met Leu Ala Gln Ser
             180                 185                 190

Asn Pro Gln Leu Phe Ala Leu Met Gly Thr Arg Ala Gly Ile Ala Arg
         195                 200                 205

Glu Leu Glu Arg Val Glu Gln Gln Ser Arg Leu Glu Gln Leu Ser Ala
     210                 215                 220

Ala Glu Leu Gln Ser Arg Asn Gln Gly His Trp Ala Asp Trp Leu Gln
225                 230                 235                 240

Ala Tyr Arg Ala Arg Leu Asp Lys Asp Leu Glu Gly Ala Gly Asp Ala
                 245                 250                 255

Ala Ala Trp Gln Ala Glu His Val Arg Val Met His Ala Asn Asn Pro
             260                 265                 270

Lys Tyr Val Leu Arg Asn Tyr Ile Ala Gln Asn Ala Ile Glu Ala Ala
         275                 280                 285

Glu Arg Gly Asp Phe Ser Glu Val Arg Arg Val Leu Lys Leu Leu Glu
     290                 295                 300

Thr Pro Tyr His Cys Glu Ala Gly Ala Ala Thr Asp Ala Glu Ala Thr
305                 310                 315                 320

Glu Ala Asp Gly Ala Asp Gly Arg Gln Arg Ser Tyr Ser Ser Lys Pro
                 325                 330                 335

Pro Leu Trp Ala Ala Glu Leu Cys Val Thr
             340                 345
```

<210> SEQ ID NO 33
<211> LENGTH: 715
<212> TYPE: PRT
<213> ORGANISM: Homo sapiens

<400> SEQUENCE: 33

```
Met Glu Arg Thr Ala Gly Lys Glu Leu Ala Leu Val Arg Gly Gln Gly
  1               5                  10                  15

Ile Pro Gly Pro Arg Ile Pro Gly Asp Pro Gln Ala Pro Leu Gln Asp
             20                  25                  30

Trp Gly Glu Glu Thr Glu Asp Gly Ala Val Tyr Ser Val Ser Leu Arg
```

-continued

```
             35                  40                  45
Arg Gln Arg Ser Gln Arg Ser Pro Ala Glu Gly Pro Gly Gly Ser
             50                  55                  60

Gln Ala Pro Ser Pro Ile Ala Asn Thr Phe Leu His Tyr Arg Thr Ser
 65                  70                  75                  80

Lys Val Arg Val Leu Arg Ala Ala Arg Leu Glu Arg Leu Val Gly Glu
                 85                  90                  95

Leu Val Phe Gly Asp Arg Glu Gln Asp Pro Ser Phe Met Pro Ala Phe
                100                 105                 110

Leu Ala Thr Tyr Arg Thr Phe Val Pro Thr Ala Cys Leu Leu Gly Phe
                115                 120                 125

Leu Leu Pro Pro Met Pro Pro Pro Pro Pro Gly Val Glu Ile Lys
        130                 135                 140

Lys Thr Ala Val Gln Asp Leu Ser Phe Asn Lys Asn Leu Arg Ala Val
145                 150                 155                 160

Val Ser Val Leu Gly Ser Trp Leu Gln Asp His Pro Gln Asp Phe Arg
                165                 170                 175

Asp Pro Pro Ala His Ser Asp Leu Gly Ser Val Arg Thr Phe Leu Gly
                180                 185                 190

Trp Ala Ala Pro Gly Ser Ala Glu Ala Gln Lys Ala Glu Lys Leu Leu
                195                 200                 205

Glu Asp Phe Leu Glu Glu Ala Glu Arg Glu Gln Glu Glu Pro Pro
        210                 215                 220

Gln Val Trp Thr Asp Ser Ser Glu Ala Cys Ala Glu Glu Glu Gly
225                 230                 235                 240

Leu Met Pro Gln Gly Pro Gln Leu Leu Asp Phe Ser Val Asp Glu Val
                245                 250                 255

Ala Glu Gln Leu Thr Leu Ile Asp Leu Glu Leu Phe Ser Lys Val Arg
                260                 265                 270

Leu Tyr Glu Cys Leu Gly Ser Val Trp Ser Gln Arg Asp Arg Pro Gly
                275                 280                 285

Ala Ala Gly Ala Ser Pro Thr Val Arg Ala Thr Val Ala Gln Phe Asn
                290                 295                 300

Thr Val Thr Gly Cys Val Leu Gly Ser Val Leu Gly Ala Pro Gly Leu
305                 310                 315                 320

Ala Ala Pro Gln Arg Ala Gln Arg Leu Glu Lys Trp Ile Arg Ile Ala
                325                 330                 335

Gln Arg Cys Arg Glu Leu Arg Asn Phe Ser Ser Leu Arg Ala Ile Leu
                340                 345                 350

Ser Ala Leu Gln Ser Asn Pro Ile Tyr Arg Leu Lys Arg Ser Trp Gly
                355                 360                 365

Ala Val Ser Arg Glu Pro Leu Ser Thr Phe Arg Lys Leu Ser Gln Ile
370                 375                 380

Phe Ser Asp Glu Asn Asn His Leu Ser Ser Arg Glu Ile Leu Phe Gln
385                 390                 395                 400

Glu Glu Ala Thr Glu Gly Ser Gln Glu Glu Asp Asn Thr Pro Gly Ser
                405                 410                 415

Leu Pro Ser Lys Pro Pro Gly Pro Val Pro Tyr Leu Gly Thr Phe
        420                 425                 430

Leu Thr Asp Leu Val Met Leu Asp Thr Ala Leu Pro Asp Met Leu Glu
                435                 440                 445

Gly Asp Leu Ile Asn Phe Glu Lys Arg Arg Lys Glu Trp Glu Ile Leu
450                 455                 460
```

```
Ala Arg Ile Gln Gln Leu Gln Arg Arg Cys Gln Ser Tyr Thr Leu Ser
465                 470                 475                 480

Pro His Pro Pro Ile Leu Ala Ala Leu His Ala Gln Asn Gln Leu Thr
                485                 490                 495

Glu Glu Gln Ser Tyr Arg Leu Ser Arg Val Ile Glu Pro Pro Ala Ala
            500                 505                 510

Ser Cys Pro Ser Ser Pro Arg Ile Arg Arg Ile Ser Leu Thr Lys
        515                 520                 525

Arg Leu Ser Ala Lys Leu Ala Arg Glu Lys Ser Ser Pro Ser Gly
    530                 535                 540

Ser Pro Gly Asp Pro Ser Ser Pro Thr Ser Ser Val Ser Pro Gly Ser
545                 550                 555                 560

Pro Pro Ser Ser Pro Arg Ser Arg Asp Ala Pro Ala Gly Ser Pro Pro
                565                 570                 575

Ala Ser Pro Gly Pro Gln Gly Pro Ser Thr Lys Leu Pro Leu Ser Leu
            580                 585                 590

Asp Leu Pro Ser Pro Arg Pro Phe Ala Leu Pro Leu Gly Ser Pro Arg
        595                 600                 605

Ile Pro Leu Pro Ala Gln Gln Ser Ser Glu Ala Arg Val Ile Arg Val
    610                 615                 620

Ser Ile Asp Asn Asp His Gly Asn Leu Tyr Arg Ser Ile Leu Leu Thr
625                 630                 635                 640

Ser Gln Asp Lys Ala Pro Ser Val Val Arg Arg Ala Leu Gln Lys His
                645                 650                 655

Asn Val Pro Gln Pro Trp Ala Cys Asp Tyr Gln Leu Phe Gln Val Leu
            660                 665                 670

Pro Gly Asp Arg Val Leu Leu Ile Pro Asp Asn Ala Asn Val Phe Tyr
        675                 680                 685

Ala Met Ser Pro Val Ala Pro Arg Asp Phe Met Leu Arg Arg Lys Glu
    690                 695                 700

Gly Thr Arg Asn Thr Leu Ser Val Ser Pro Ser
705                 710                 715

<210> SEQ ID NO 34
<211> LENGTH: 699
<212> TYPE: PRT
<213> ORGANISM: Homo sapiens

<400> SEQUENCE: 34

Met Glu Arg Thr Ala Gly Lys Glu Leu Ala Leu Val Arg Gly Gln Gly
1               5                   10                  15

Ile Pro Gly Pro Arg Ile Pro Gly Asp Pro Gln Ala Pro Leu Gln Asp
            20                  25                  30

Trp Gly Glu Glu Thr Glu Asp Gly Ala Val Tyr Ser Val Ser Leu Arg
        35                  40                  45

Arg Gln Arg Ser Gln Arg Arg Ser Pro Ala Glu Gly Pro Gly Gly Ser
    50                  55                  60

Gln Ala Pro Ser Pro Ile Ala Asn Thr Phe Leu His Tyr Arg Thr Ser
65                  70                  75                  80

Lys Val Arg Val Leu Arg Ala Ala Arg Leu Glu Arg Leu Val Gly Glu
                85                  90                  95

Leu Val Phe Gly Asp Arg Glu Gln Asp Pro Ser Phe Met Pro Ala Phe
            100                 105                 110

Leu Ala Thr Tyr Arg Thr Phe Val Pro Thr Ala Cys Leu Leu Gly Phe
```

```
                    115                 120                 125
Leu Leu Pro Pro Met Pro Pro Pro Pro Pro Gly Val Glu Ile Lys
    130                 135                 140
Lys Thr Ala Val Gln Asp Leu Ser Phe Asn Lys Asn Leu Arg Ala Val
145                 150                 155                 160
Val Ser Val Leu Gly Ser Trp Leu Gln Asp His Pro Gln Asp Phe Arg
                165                 170                 175
Asp Pro Pro Ala His Ser Asp Leu Gly Ser Val Arg Thr Phe Leu Gly
            180                 185                 190
Trp Ala Ala Pro Gly Ser Ala Glu Ala Gln Lys Ala Glu Lys Leu Leu
        195                 200                 205
Glu Asp Phe Leu Glu Glu Ala Glu Arg Glu Gln Glu Glu Pro Pro
    210                 215                 220
Gln Val Trp Thr Asp Ser Ser Glu Ala Cys Ala Glu Glu Glu Gly
225                 230                 235                 240
Leu Met Pro Gln Gly Pro Gln Leu Leu Asp Phe Ser Val Asp Glu Val
                245                 250                 255
Ala Glu Gln Leu Thr Leu Ile Asp Leu Glu Leu Phe Ser Lys Val Arg
            260                 265                 270
Leu Tyr Glu Cys Leu Gly Ser Val Trp Ser Gln Arg Asp Arg Pro Gly
        275                 280                 285
Ala Ala Gly Ala Ser Pro Thr Val Arg Ala Thr Val Ala Gln Phe Asn
290                 295                 300
Thr Val Thr Gly Cys Val Leu Gly Ser Val Leu Gly Ala Pro Gly Leu
305                 310                 315                 320
Ala Ala Pro Gln Arg Ala Gln Arg Leu Glu Lys Trp Ile Arg Ile Ala
                325                 330                 335
Gln Arg Cys Arg Glu Leu Arg Asn Phe Ser Ser Leu Arg Ala Ile Leu
            340                 345                 350
Ser Ala Leu Gln Ser Asn Pro Ile Tyr Arg Leu Lys Arg Ser Trp Gly
        355                 360                 365
Ala Val Ser Arg Glu Pro Leu Ser Thr Phe Arg Lys Leu Ser Gln Ile
    370                 375                 380
Phe Ser Asp Glu Asn Asn His Leu Ser Ser Arg Glu Ile Leu Phe Gln
385                 390                 395                 400
Glu Glu Ala Thr Glu Gly Ser Gln Glu Glu Asp Asn Thr Pro Gly Ser
                405                 410                 415
Leu Pro Ser Lys Pro Pro Gly Pro Val Pro Tyr Leu Gly Thr Phe
            420                 425                 430
Leu Thr Asp Leu Val Met Leu Asp Thr Ala Leu Pro Asp Met Leu Glu
        435                 440                 445
Gly Asp Leu Ile Asn Phe Glu Lys Arg Arg Lys Glu Trp Glu Ile Leu
    450                 455                 460
Ala Arg Ile Gln Gln Leu Gln Arg Arg Cys Gln Ser Tyr Thr Leu Ser
465                 470                 475                 480
Pro His Pro Pro Ile Leu Ala Ala Leu His Ala Gln Asn Gln Leu Thr
                485                 490                 495
Glu Glu Gln Ser Tyr Arg Leu Ser Arg Val Ile Glu Pro Pro Ala Ala
            500                 505                 510
Ser Cys Pro Ser Ser Pro Arg Ile Arg Arg Ile Ser Leu Thr Lys
        515                 520                 525
Arg Leu Ser Ala Lys Leu Ala Arg Glu Lys Ser Ser Ser Pro Ser Gly
    530                 535                 540
```

```
Ser Pro Gly Asp Pro Ser Ser Pro Thr Ser Ser Val Ser Pro Gly Ser
545                 550                 555                 560

Pro Pro Ser Ser Pro Arg Ser Arg Asp Ala Pro Ala Gly Ser Pro Pro
            565                 570                 575

Ala Ser Pro Gly Pro Gln Gly Pro Ser Thr Lys Leu Pro Leu Ser Leu
            580                 585                 590

Asp Leu Pro Ser Pro Arg Pro Phe Ala Leu Pro Leu Gly Ser Pro Arg
        595                 600                 605

Ile Pro Leu Pro Ala Gln Gln Ser Ser Glu Ala Arg Val Ile Arg Val
    610                 615                 620

Ser Ile Asp Asn Asp His Gly Asn Leu Tyr Arg Ser Ile Leu Leu Thr
625                 630                 635                 640

Ser Gln Asp Lys Ala Pro Ser Val Val Arg Arg Ala Leu Gln Lys His
                645                 650                 655

Asn Val Pro Gln Pro Trp Ala Cys Asp Tyr Gln Leu Phe Gln Val Leu
            660                 665                 670

Pro Gly Asp Arg Val Ala Pro Arg Asp Phe Met Leu Arg Arg Lys Glu
            675                 680                 685

Gly Thr Arg Asn Thr Leu Ser Val Ser Pro Ser
            690                 695
```

NUCLEIC ACIDS AND POLYPEPTIDES

1. CROSS REFERENCE TO RELATED APPLICATIONS

This application is a continuation-in-part application of U.S. application Ser. No. 09/649,167, filed Aug. 23, 2000, now abandoned which in turn is a continuation-in-part application of U.S. application Ser. No. 09/540,217, filed Mar. 31, 2000, now abandoned both of which are incorporated herein by reference in their entirety.

2. BACKGROUND OF THE INVENTION

2.1. Technical Field

The present invention provides novel polynucleotides and proteins encoded by such polynucleotides, along with uses for these polynucleotides and proteins, for example in therapeutic, diagnostic and research methods.

2.2 Background

Technology aimed at the discovery of protein factors (including e.g., cytokines, such as lymphokines, interferons, CSFs, chemokines, and interleukins) has matured rapidly over the past decade. The now routine hybridization cloning and expression cloning techniques clone novel polynucleotides "directly" in the sense that they rely on information directly related to the discovered protein (i.e., partial DNA/amino acid sequence of the protein in the case of hybridization cloning; activity of the protein in the case of expression cloning). More recent "indirect" cloning techniques such as signal sequence cloning, which isolates DNA sequences based on the presence of a now well-recognized secretory leader sequence motif, as well as various PCR-based or low stringency hybridization-based cloning techniques, have advanced the state of the art by making available large numbers of DNA/amino acid sequences for proteins that are known to have biological activity, for example, by virtue of their secreted nature in the case of leader sequence cloning, by virtue of their cell or tissue source in the case of PCR-based techniques, or by virtue of structural similarity to other genes of known biological activity.

Identified polynucleotide and polypeptide sequences have numerous applications in, for example, diagnostics, forensics, gene mapping; identification of mutations responsible for genetic disorders or other traits, to assess biodiversity, and to produce many other types of data and products dependent on DNA and amino acid sequences.

3. SUMMARY OF THE INVENTION

The compositions of the present invention include novel isolated polypeptides, novel isolated polynucleotides encoding such polypeptides, including recombinant DNA molecules, cloned genes or degenerate variants thereof, especially naturally occurring variants such as allelic variants, antisense polynucleotide molecules, and antibodies that specifically recognize one or more epitopes present on such polypeptides, as well as hybridomas producing such antibodies.

The compositions of the present invention additionally include vectors, including expression vectors, containing the polynucleotides of the invention, cells genetically engineered to contain such polynucleotides and cells genetically engineered to express such polynucleotides.

The present invention relates to a collection or library of at least one novel nucleic acid sequence assembled from expressed sequence tags (ESTs) isolated mainly by sequencing by hybridization (SBH), and in some cases, sequences obtained from one or more public databases. The invention relates also to the proteins encoded by such polynucleotides, along with therapeutic, diagnostic and research utilities for these polynucleotides and proteins. These nucleic acid sequences are designated as SEQ ID NO: 1–17 and are provided in the Sequence Listing. In the nucleic acids provided in the Sequence Listing, A is adenine; C is cytosine; G is guanine; T is thymine; and N is any of the four bases. In the amino acids provided in the Sequence Listing, * corresponds to the stop codon.

The nucleic acid sequences of the present invention also include, nucleic acid sequences that hybridize to the complement of SEQ ID NO: 1–17 under stringent hybridization conditions; nucleic acid sequences which are allelic variants or species homologues of any of the nucleic acid sequences recited above, or nucleic acid sequences that encode a peptide comprising a specific domain or truncation of the peptides encoded by SEQ ID NO: 1–17. A polynucleotide comprising a nucleotide sequence having at least 90% identity to an identifying sequence of SEQ ID NO: 1–17 or a degenerate variant or fragment thereof. The identifying sequence can be 100 base pairs in length.

The nucleic acid sequences of the present invention also include the sequence information from the nucleic acid sequences of SEQ ID NO: 1–17. The sequence information can be a segment of any one of SEQ ID NO: 1–17 that uniquely identifies or represents the sequence information of SEQ ID NO: 1–17.

A collection as used in this application can be a collection of only one polynucleotide. The collection of sequence information or identifying information of each sequence can be provided on a nucleic acid array. In one embodiment, segments of sequence information are provided on a nucleic acid array to detect the polynucleotide that contains the segment. The array can be designed to detect full-match or mismatch to the polynucleotide that contains the segment. The collection can also be provided in a computer-readable format.

This invention also includes the reverse or direct complement of any of the nucleic acid sequences recited above; cloning or expression vectors containing the nucleic acid sequences; and host cells or organisms transformed with these expression vectors. Nucleic acid sequences (or their reverse or direct complements) according to the invention have numerous applications in a variety of techniques known to those skilled in the art of molecular biology, such as use as hybridization probes, use as primers for PCR, use in an array, use in computer-readable media, use in sequencing full-length genes, use for chromosome and gene mapping, use in the recombinant production of protein, and use in the generation of anti-sense DNA or RNA, their chemical analogs and the like.

In a preferred embodiment, the nucleic acid sequences of SEQ ID NO: 1–17 or novel segments or parts of the nucleic acids of the invention are used as primers in expression assays that are well known in the art. In a particularly preferred embodiment, the nucleic acid sequences of SEQ ID NO: 1–17 or novel segments or parts of the nucleic acids provided herein are used in diagnostics for identifying expressed genes or, as well known in the art and exemplified by Vollrath et al., Science 258:52–59 (1992), as expressed sequence tags for physical mapping of the human genome.

The isolated polynucleotides of the invention include, but are not limited to, a polynucleotide comprising any one of the nucleotide sequences set forth in SEQ ID NO: 1–17; a polynucleotide comprising any of the full length protein coding sequences of SEQ ID NO: 1–17; and a polynucleotide comprising any of the nucleotide sequences of the mature protein coding sequences of SEQ ID NO: 1–17. The polynucleotides of the present invention also include, but are not limited to, a polynucleotide that hybridizes under stringent hybridization conditions to (a) the complement of any one of the nucleotide sequences set forth in SEQ ID NO: 1–17; (b) a nucleotide sequence encoding any one of the amino acid sequences set forth in the Sequence Listing; (c) a polynucleotide which is an allelic variant of any polynucleotides recited above; (d) a polynucleotide which encodes a species homolog (e.g. orthologs) of any of the proteins recited above; or (e) a polynucleotide that encodes a polypeptide comprising a specific domain or truncation of any of the polypeptides comprising an amino acid sequence set forth in the Sequence Listing.

The isolated polypeptides of the invention include, but are not limited to, a polypeptide comprising any of the amino acid sequences set forth in the Sequence Listing; or the corresponding full length or mature protein. Polypeptides of the invention also include polypeptides with biological activity that are encoded by (a) any of the polynucleotides having a nucleotide sequence set forth in SEQ ID NO: 1–17; or (b) polynucleotides that hybridize to the complement of the polynucleotides of (a) under stringent hybridization conditions. Biologically or immunologically active variants of any of the polypeptide sequences in the Sequence Listing, and "substantial equivalents" thereof (e.g., with at least about 65%, 70%, 75%, 80%, 85%, 90%, 95%, 98% or 99% amino acid sequence identity) that preferably retain biological activity are also contemplated. The polypeptides of the invention may be wholly or partially chemically synthesized but are preferably produced by recombinant means using the genetically engineered cells (e.g. host cells) of the invention.

The invention also provides compositions comprising a polypeptide of the invention. Polypeptide compositions of the invention may further comprise an acceptable carrier, such as a hydrophilic, e.g., pharmaceutically acceptable, carrier.

The invention also provides host cells transformed or transfected with a polynucleotide of the invention.

The invention also relates to methods for producing a polypeptide of the invention comprising growing a culture of the host cells of the invention in a suitable culture medium under conditions permitting expression of the desired polypeptide, and purifying the polypeptide from the culture or from the host cells. Preferred embodiments include those in which the protein produced by such process is a mature form of the protein.

Polynucleotides according to the invention have numerous applications in a variety of techniques known to those skilled in the art of molecular biology. These techniques include use as hybridization probes, use as oligomers, or primers, for PCR, use for chromosome and gene mapping, use in the recombinant production of protein, and use in generation of anti-sense DNA or RNA, their chemical analogs and the like. For example, when the expression of an mRNA is largely restricted to a particular cell or tissue type, polynucleotides of the invention can be used as hybridization probes to detect the presence of the particular cell or tissue mRNA in a sample using, e.g., in situ hybridization.

In other exemplary embodiments, the polynucleotides are used in diagnostics as expressed sequence tags for identifying expressed genes or, as well known in the art and exemplified by Vollrath et al., Science 258:52–59 (1992), as expressed sequence tags for physical mapping of the human genome.

The polypeptides according to the invention can be used in a variety of conventional procedures and methods that are currently applied to other proteins. For example, a polypeptide of the invention can be used to generate an antibody that specifically binds the polypeptide. Such antibodies, particularly monoclonal antibodies, are useful for detecting or quantitating the polypeptide in tissue. The polypeptides of the invention can also be used as molecular weight markers, and as a food supplement.

Methods are also provided for preventing, treating, or ameliorating a medical condition which comprises the step of administering to a mammalian subject a therapeutically effective amount of a composition comprising a polypeptide of the present invention and a pharmaceutically acceptable carrier.

In particular, the polypeptides and polynucleotides of the invention can be utilized, for example, in methods for the prevention and/or treatment of disorders involving aberrant protein expression or biological activity.

The present invention further relates to methods for detecting the presence of the polynucleotides or polypeptides of the invention in a sample. Such methods can, for example, be utilized as part of prognostic and diagnostic evaluation of disorders as recited herein and for the identification of subjects exhibiting a predisposition to such conditions. The invention provides a method for detecting the polynucleotides of the invention in a sample, comprising contacting the sample with a compound that binds to and forms a complex with the polynucleotide of interest for a period sufficient to form the complex and under conditions sufficient to form a complex and detecting the complex such that if a complex is detected, the polynucleotide of interest is detected. The invention also provides a method for detecting the polypeptides of the invention in a sample comprising contacting the sample with a compound that binds to and forms a complex with the polypeptide under conditions and for a period sufficient to form the complex and detecting the formation of the complex such that if a complex is formed, the polypeptide is detected.

The invention also provides kits comprising polynucleotide probes and/or monoclonal antibodies, and optionally quantitative standards, for carrying out methods of the invention. Furthermore, the invention provides methods for evaluating the efficacy of drugs, and monitoring the progress of patients, involved in clinical trials for the treatment of disorders as recited above.

The invention also provides methods for the identification of compounds that modulate (i.e., increase or decrease) the expression or activity of the polynucleotides and/or polypeptides of the invention. Such methods can be utilized, for example, for the identification of compounds that can ameliorate symptoms of disorders as recited herein. Such methods can include, but are not limited to, assays for identifying compounds and other substances that interact with (e.g., bind to) the polypeptides of the invention. The invention provides a method for identifying a compound that binds to the polypeptides of the invention comprising contacting the compound with a polypeptide of the invention in a cell for a time sufficient to form a polypeptide/compound complex, wherein the complex drives expression of a reporter gene sequence in the cell; and detecting the complex by detecting the reporter gene sequence expression such that if expression of the reporter gene is detected the compound that binds to a polypeptide of the invention is identified.

The methods of the invention also provides methods for treatment which involve the administration of the polynucleotides or polypeptides of the invention to individuals exhibiting symptoms or tendencies. In addition, the invention encompasses methods for treating diseases or disorders as recited herein comprising administering compounds and other substances that modulate the overall activity of the target gene products. Compounds and other substances can effect such modulation either on the level of target gene/protein expression or target protein activity.

The polypeptides of the present invention and the polynucleotides encoding them are also useful for the same functions known to one of skill in the art as the polypeptides and polynucleotides to which they have homology (set forth in Table 2); for which they have a signature region (as set forth in Table 3); or for which they have homology to a gene family (as set forth in Table 4). If no homology is set forth for a sequence, then the polypeptides and polynucleotides of the present invention are useful for a variety of applications, as described herein, including use in arrays for detection.

4. DETAILED DESCRIPTION OF THE INVENTION 4.1 Definitions

It must be noted that as used herein and in the appended claims, the singular forms "a", "an" and "the" include plural references unless the context clearly dictates otherwise.

The term "active" refers to those forms of the polypeptide which retain the biologic and/or immunologic activities of any naturally occurring polypeptide. According to the invention, the terms "biologically active" or "biological activity" refer to a protein or peptide having structural, regulatory or biochemical functions of a naturally occurring molecule. Likewise "immunologically active" or "immunological activity" refers to the capability of the natural, recombinant or synthetic polypeptide to induce a specific immune response in appropriate animals or cells and to bind with specific antibodies.

The term "activated cells" as used in this application are those cells which are engaged in extracellular or intracellular membrane trafficking, including the export of secretory or enzymatic molecules as part of a normal or disease process.

The terms "complementary" or "complementarity" refer to the natural binding of polynucleotides by base pairing. For example, the sequence 5'-AGT-3' binds to the complementary sequence 3'-TCA-5'. Complementarity between two single-stranded molecules may be "partial" such that only some of the nucleic acids bind or it may be "complete" such that total complementarity exists between the single stranded molecules. The degree of complementarity between the nucleic acid strands has significant effects on the efficiency and strength of the hybridization between the nucleic acid strands.

The term "embryonic stem cells (ES)" refers to a cell that can give rise to many differentiated cell types in an embryo or an adult, including the germ cells. The term "germ line stem cells (GSCs)" refers to stem cells derived from primordial stem cells that provide a steady and continuous source of germ cells for the production of gametes. The term "primordial germ cells (PGCs)" refers to a small population of cells set aside from other cell lineages particularly from the yolk sac, mesenteries, or gonadal ridges during embryogenesis that have the potential to differentiate into germ cells and other cells. PGCs are the source from which GSCs and ES cells are derived The PGCs, the GSCs and the ES cells are capable of self-renewal. Thus these cells not only populate the germ line and give rise to a plurality of terminally differentiated cells that comprise the adult specialized organs, but are able to regenerate themselves.

The term "expression modulating fragment," EMF, means a series of nucleotides which modulates the expression of an operably linked ORF or another EMF.

As used herein, a sequence is said to "modulate the expression of an operably, linked sequence" when the expression of the sequence is altered by the presence of the EMF. EMFs include, but are not limited to, promoters, and promoter modulating sequences (inducible elements). One class of EMFs are nucleic acid fragments which induce the expression of an operably linked ORF in response to a specific regulatory factor or physiological event.

The terms "nucleotide sequence" or "nucleic acid" or "polynucleotide" or "oligonucleotide" are used interchangeably and refer to a heteropolymer of nucleotides or the sequence of these nucleotides. These phrases also refer to DNA or RNA of genomic or synthetic origin which may be single-stranded or double-stranded and may represent the sense or the antisense strand, to peptide nucleic acid (PNA) or to any DNA-like or RNA-like material. In the sequences herein A is adenine, C is cytosine, T is thymine, G is guanine and N is A, C, G or T (U). It is contemplated that where the polynucleotide is RNA, the T (thymine) in the sequences provided herein is substituted with U (uracil). Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "oligonucleotide fragment" or a "polynucleotide fragment", "portion," or "segment" or "probe" or "primer" are used interchangeably and refer to a sequence of nucleotide residues which are at least about 5 nucleotides, more preferably at least about 7 nucleotides, more preferably at least about 9 nucleotides, more preferably at least about 11 nucleotides and most preferably at least about 17 nucleotides. The fragment is preferably less than about 500 nucleotides, preferably less than about 200 nucleotides, more preferably less than about 100 nucleotides, more preferably less than about 50 nucleotides and most preferably less than 30 nucleotides. Preferably the probe is from about 6 nucleotides to about 200 nucleotides, preferably from about 15 to about 50 nucleotides, more preferably from about 17 to 30 nucleotides and most preferably from about 20 to 25 nucleotides. Preferably the fragments can be used in polymerase chain reaction (PCR), various hybridization procedures or microarray procedures to identify or amplify identical or related parts of mRNA or DNA molecules. A fragment or segment may uniquely identify each polynucleotide sequence of the present invention. Preferably the fragment comprises a sequence substantially similar to any one of SEQ ID NOs:1–17.

Probes may, for example, be used to determine whether specific mRNA molecules are present in a cell or tissue or to isolate similar nucleic acid sequences from chromosomal DNA as described by Walsh et al. (Walsh, P. S. et al., 1992, PCR Methods Appl 1:241–250). They may be labeled by nick translation, Klenow fill-in reaction, PCR, or other methods well known in the art. Probes of the present invention, their preparation and/or labeling are elaborated in Sambrook, J. et al., 1989, Molecular Cloning: A Laboratory Manual, Cold Spring Harbor Laboratory, N.Y.; or Ausubel, F. M. et al., 1989, Current Protocols in Molecular Biology, John Wiley & Sons, New York N.Y., both of which are incorporated herein by reference in their entirety.

The nucleic acid sequences of the present invention also include the sequence information from the nucleic acid sequences of SEQ ID NOs: 1–17. The sequence information can be a segment of any one of SEQ ID NOs: 1–17 that uniquely identifies or represents the sequence information of that sequence of SEQ ID NO: 1–17. One such segment can be a twenty-mer nucleic acid sequence because the probability that a twenty-mer is fully matched in the human genome is 1 in 300. In the human genome, there are three billion base pairs in one set of chromosomes. Because $4^{20}$ possible twenty-mers exist, there are 300 times more twenty-mers than there are base pairs in a set of human chromosomes. Using the same analysis, the probability for a seventeen-mer to be fully matched in the human genome is approximately 1 in 5. When these segments are used in arrays for expression studies, fifteen-mer segments can be used. The probability that the fifteen-mer is fully matched in the expressed sequences is also approximately one in five because expressed sequences comprise less than approximately 5% of the entire genome sequence.

Similarly, when using sequence information for detecting a single mismatch, a segment can be a twenty-five mer. The probability that the twenty-five mer would appear in a human genome with a single mismatch is calculated by multiplying the probability for a full match $(1 \div 4^{25})$ times the increased probability for mismatch at each nucleotide position $(3 \times 25)$. The probability that an eighteen mer with a single mismatch can be detected in an array for expression studies is approximately one in five. The probability that a twenty-mer with a single mismatch can be detected in a human genome is approximately one in five.

The term "open reading frame," ORF, means a series of nucleotide triplets coding for amino acids without any termination codons and is a sequence translatable into protein.

The terms "operably linked" or "operably associated" refer to functionally related nucleic acid sequences. For example, a promoter is operably associated or operably linked with a coding sequence if the promoter controls the transcription of the coding sequence. While operably linked nucleic acid sequences can be contiguous and in the same reading frame, certain genetic elements e.g. repressor genes are not contiguously linked to the coding sequence but still control transcription/translation of the coding sequence.

The term "pluripotent" refers to the capability of a cell to differentiate into a number of differentiated cell types that are present in an adult organism. A pluripotent cell is restricted in its differentiation capability in comparison to a totipotent cell.

The terms "polypeptide" or "peptide" or "amino acid sequence" refer to an oligopeptide, peptide, polypeptide or protein sequence or fragment thereof and to naturally occurring or synthetic molecules. A polypeptide "fragment," "portion," or "segment" is a stretch of amino acid residues of at least about 5 amino acids, preferably at least about 7 amino acids, more preferably at least about 9 amino acids and most preferably at least about 17 or more amino acids. The peptide preferably is not greater than about 200 amino acids, more preferably less than 150 amino acids and most preferably less than 100 amino acids. Preferably the peptide is from about 5 to about 200 amino acids. To be active, any polypeptide must have sufficient length to display biological and/or immunological activity.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "translated protein coding portion" means a sequence which encodes for the full length protein which may include any leader sequence or any processing sequence.

The term "mature protein coding sequence" means a sequence which encodes a peptide or protein without a signal or leader sequence. The "mature protein portion" means that portion of the protein which does not include a signal or leader sequence. The peptide may have been produced by processing in the cell which removes any leader/signal sequence. The mature protein portion may or may not include the initial methionine residue. The methionine residue may be removed from the protein during processing in the cell. The peptide may be produced synthetically or the protein may have been produced using a polynucleotide only encoding for the mature protein coding sequence.

The term "derivative" refers to polypeptides chemically modified by such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins.

The term "variant" (or "analog") refers to any polypeptide differing from naturally occurring polypeptides by amino acid insertions, deletions, and substitutions, created using, e g., recombinant DNA techniques. Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are preferably in the range of about 1 to 20 amino acids, more preferably 1 to 10 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

The terms "purified" or "substantially purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "recombinant," when used herein to refer to a polypeptide or protein, means that a polypeptide or protein is derived from recombinant (e.g., microbial, insect, or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures; e.g., E. coli, will be free of glycosylation modifications; polypeptides or proteins expressed in yeast will have a glycosylation pattern in general different from those expressed in mammalian cells.

The term "recombinant expression vehicle or vector" refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an amino terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "secreted" includes a protein that is transported across or through a membrane, including transport as a result of signal sequences in its amino acid sequence when it is expressed in a suitable host cell. "Secreted" proteins include without limitation proteins secreted wholly (e.g., soluble proteins) or partially (e.g., receptors) from the cell in which they are expressed. "Secreted" proteins also include without limitation proteins that are transported across the membrane of the endoplasmic reticulum. "Secreted" proteins are also intended to include proteins containing non-typical signal sequences (e.g. Interleukin-1 Beta, see Krasney, P. A. and Young, P. R. (1992) Cytokine 4(2):134–143) and factors released from damaged cells (e.g. Interleukin-1 Receptor Antagonist, see Arend, W. P. et. al. (1998) Annu. Rev. Immunol. 16:27–55).

Where desired, an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

The term "stringent" is used to refer to conditions that are commonly understood in the art as stringent. Stringent conditions can include highly stringent conditions (i.e., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C.), and moderately stringent conditions (i.e., washing in 0.2×SSC/0.1% SDS at 42° C.). Other exemplary hybridization conditions are described herein in the examples.

In instances of hybridization of deoxyoligonucleotides, additional exemplary stringent hybridization conditions include washing in 6×SSC/0.05% sodium pyrophosphate at 37° C. (for 14-base oligonucleotides), 48° C. (for 17-base oligos), 55° C. (for 20-base oligonucleotides), and 60° C. (for 23-base oligonucleotides).

As used herein, "substantially equivalent" or "substantially similar" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 35% (i.e., the number of individual residue substitutions, additions, and/or deletions in a substantially equivalent sequence, as compared to the corresponding reference sequence, divided by the total number of residues in the substantially equivalent sequence is about 0.35 or less). Such a sequence is said to have 65% sequence identity to the listed sequence. In one embodiment, a substantially equivalent, e.g., mutant, sequence of the invention varies from a listed sequence by no more than 30% (70% sequence identity); in a variation of this embodiment, by no more than 25% (75% sequence identity); and in a further variation of this embodiment, by no more than 20% (80% sequence identity) and in a further variation of this embodiment, by no more than 10% (90% sequence identity) and in a further variation of this embodiment, by no more that 5% (95% sequence identity). Substantially equivalent, e.g., mutant, amino acid sequences according to the invention preferably have at least 80% sequence identity with a listed amino acid sequence, more preferably at least 85% sequence identity, more preferably at least 90% sequence identity, more preferably at least 95% sequence identity, more preferably at least 98% sequence identity, and most preferably at least 99% sequence identity. Substantially equivalent nucleotide sequence of the invention can have lower percent sequence identities, taking into account, for example, the redundancy or degeneracy of the genetic code. Preferably, the nucleotide sequence has at least about 65% identity, more preferably at least about 75% identity, more preferably at least about 80% sequence identity, more preferably at least 85% sequence identity, more preferably at least 90% sequence identity, more preferably at least about 95% sequence identity, more preferably at least 98% sequence identity, and most preferably at least 99% sequence identity. For the purposes of the present invention, sequences having substantially equivalent biological activity and substantially equivalent expression characteristics are considered substantially equivalent. For the purposes of determining equivalence, truncation of the mature sequence (e.g., via a mutation which creates a spurious stop codon) should be disregarded. Sequence identity may be determined, e.g., using the Jotun Hein method (Hein, J. (1990) Methods Enzymol. 183:626–645). Identity between sequences can also be determined by other methods known in the art, e.g. by varying hybridization conditions.

The term "totipotent" refers to the capability of a cell to differentiate into all of the cell types of an adult organism.

The term "transformation" means introducing DNA into a suitable host cell so that the DNA is replicable, either as an extrachromosomal element, or by chromosomal integration. The term "transfection" refers to the taking up of an expression vector by a suitable host cell, whether or not any coding sequences are in fact expressed. The term "infection" refers to the introduction of nucleic acids into a suitable host cell by use of a virus or viral vector.

As used herein, an "uptake modulating fragment," UMF, means a series of nucleotides which mediate the uptake of a linked DNA fragment into a cell. UMFs can be readily identified using known UMFs as a target sequence or target motif with the computer-based systems described below. The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

Each of the above terms is meant to encompass all that is described for each, unless the context dictates otherwise.

4.2 Nucleic Acids of the Invention

Nucleotide sequences of the invention are set forth in the Sequence Listing.

The isolated polynucleotides of the invention include a polynucleotide comprising the nucleotide sequences of SEQ ID NO: 1–17; a polynucleotide encoding any one of the peptide sequences of SEQ ID NO: 18–34; and a polynucleotide comprising the nucleotide sequence encoding the mature protein coding sequence of the polynucleotides of any one of SEQ ID NO: 1–17. The polynucleotides of the present invention also include, but are not limited to, a polynucleotide that hybridizes under stringent conditions to (a) the complement of any of the nucleotides sequences of SEQ ID NO: 1–17; (b) nucleotide sequences encoding any one of the amino acid sequences set forth in the Sequence Listing; (c) a polynucleotide which is an allelic variant of any polynucleotide recited above; (d) a polynucleotide which encodes a species homolog of any of the proteins recited above; or (e) a polynucleotide that encodes a polypeptide comprising a specific domain or truncation of the polypeptides of encoded by SEQ ID NO: 1–17 (i.e. SEQ ID NO: 18–34). Domains of interest may depend on the nature of the encoded polypeptide; e.g., domains in receptor-like polypeptides include ligand-binding, extracellular, transmembrane, or cytoplasmic domains, or combinations thereof; domains in immunoglobulin-like proteins include the variable immunoglobulin-like domains; domains in enzyme-like polypeptides include catalytic and substrate binding domains; and domains in ligand polypeptides include receptor-binding domains.

The polynucleotides of the invention include naturally occurring or wholly or partially synthetic DNA, e.g., cDNA and genomic DNA, and RNA, e.g., mRNA. The polynucleotides may include all of the coding region of the cDNA or may represent a portion of the coding region of the cDNA.

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. Further 5' and 3' sequence can be obtained using methods known in the art. For example, full length cDNA or genomic DNA that corresponds to any of the polynucleotides of SEQ ID NO: 1–17 can be obtained by screening appropriate cDNA or genomic DNA libraries under suitable hybridization conditions using any of the polynucleotides of SEQ ID NO: 1–17 or a portion thereof as a probe. Alternatively, the polynucleotides of SEQ ID NO: 1–17 may be used as the basis for suitable primer(s) that allow. identification and/or amplification of genes in appropriate genomic DNA or cDNA libraries.

The nucleic acid sequences of the invention can be assembled from ESTs and sequences (including cDNA and genomic sequences) obtained from one or more public databases, such as dbEST, gbpri, and UniGene. The EST sequences can provide identifying sequence information, representative fragment or segment information, or novel segment information for the full-length gene.

The polynucleotides of the invention also provide polynucleotides including nucleotide sequences that are substantially equivalent to the polynucleotides recited above. Polynucleotides according to the invention can have, e.g., at least about 65%, at least about 70%, at least about 75%, at least about 80%, 81%, 82%, 83%, 84%, more typically at least about 85%, 86%, 87%, 88%, 89%, more typically at least about 90%, 91%, 92%, 93%, 94%, and even more typically at least about 95%, 96%, 97%, 98%, 99% sequence identity to a polynucleotide recited above.

Included within the scope of the nucleic acid sequences of the invention are nucleic acid sequence fragments that hybridize under stringent conditions to any of the nucleotide sequences of SEQ ID NO: 1–17, or complements thereof, which fragment is greater than about 5 nucleotides, preferably 7 nucleotides, more preferably greater than 9 nucleotides and most preferably greater than 17 nucleotides. Fragments of, e.g. 15, 17, or 20 nucleotides or more that are selective for (i.e. specifically hybridize to) any one of the polynucleotides of the invention are contemplated. Probes capable of specifically hybridizing to a polynucleotide can differentiate polynucleotide sequences of the invention from other polynucleotide sequences in the same family of genes or can differentiate human genes from genes of other species, and are preferably based on unique nucleotide sequences.

The sequences falling within the scope of the present invention are not limited to these specific sequences, but also include allelic and species variations thereof. Allelic and species variations can be routinely determined by comparing the sequence provided in SEQ ID NO: 1–17, a representative fragment thereof, or a nucleotide sequence at least 90% identical, preferably 95% identical, to SEQ ID NOs: 1–17 with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another codon that encodes the same amino acid is expressly contemplated.

The nearest neighbor or homology result for the nucleic acids of the present invention, including SEQ ID NOs: 1–17, can be obtained by searching a database using an algorithm or a program. Preferably, a BLAST which stands for Basic Local Alignment Search Tool is used to search for local sequence alignments (Altshul, S. F. J Mol. Evol. 36 290–300 (1993) and Altschul S. F. et al. J. Mol. Biol. 21:403–410 (1990)). Alternatively a FASTA version 3 search against Genpept, using Fastxy algorithm.

Species homologs (or orthologs) of the disclosed polynucleotides and proteins are also provided by the present invention. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous or related to that encoded by the polynucleotides.

The nucleic acid sequences of the invention are further directed to sequences which encode variants of the described nucleic acids. These amino acid sequence variants may be prepared by methods known in the art by introducing appropriate nucleotide changes, into a native or variant polynucleotide. There are two variables in the construction of amino acid sequence variants: the location of the mutation and the nature of the mutation. Nucleic acids encoding the amino acid sequence variants are preferably constructed by mutating the polynucleotide to encode an amino acid sequence that does not occur in nature. These nucleic acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site. Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells and sequences such as FLAG or poly-histidine sequences useful for purifying the expressed protein.

In a preferred method, polynucleotides encoding the novel amino acid sequences are changed via site-directed mutagenesis. This method uses oligonucleotide sequences to alter a polynucleotide to encode the desired amino acid variant, as well as sufficient adjacent nucleotides on both sides of the changed amino acid to form a stable duplex on either side of the site of being changed. In general, the techniques of site-directed mutagenesis are well known to those of skill in the art and this technique is exemplified by publications such as, Edelman et al., *DNA* 2:183 (1983). A versatile and efficient method for producing site-specific changes in a polynucleotide sequence was published by Zoller and Smith, *Nucleic Acids Res.* 10:6487–6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives a polynucleotide encoding the desired amino acid variant.

A further technique for generating amino acid variants is the cassette mutagenesis technique described in Wells et al., *Gene* 34:315 (1985); and other mutagenesis techniques well known in the art, such as, for example, the techniques in Sambrook et al., supra, and *Current Protocols in Molecular Biology*, Ausubel et al. Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

Polynucleotides encoding preferred polypeptide truncations of the invention can be used to generate polynucleotides encoding chimeric or fusion proteins comprising one or more domains of the invention and heterologous protein sequences.

The polynucleotides of the invention additionally include the complement of any of the polynucleotides recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions that can routinely isolate polynucleotides of the desired sequence identities.

In accordance with the invention, polynucleotide sequences comprising the mature protein coding sequences corresponding to any one of SEQ ID NO: 1–17, or functional equivalents thereof, may be used to generate recombinant DNA molecules that direct the expression of that nucleic acid, or a functional equivalent thereof, in appropriate host cells. Also included are the cDNA inserts of any of the clones identified herein.

A polynucleotide according to the invention can be joined to any of a variety of other nucleotide sequences by well-established recombinant DNA techniques (see Sambrook J et al. (1989) Molecular Cloning: A Laboratory Manual, Cold Spring Harbor Laboratory, N.Y.). Useful nucleotide sequences for joining to polynucleotides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The present invention further provides recombinant constructs comprising a nucleic acid having any of the nucleotide sequences of SEQ ID NOs: 1–17 or a fragment thereof or any other polynucleotides of the invention. In one embodiment, the recombinant constructs of the present invention comprise a vector, such as a plasmid or viral vector, into which a nucleic acid having any of the nucleotide sequences of SEQ ID NOs: 1–17 or a fragment thereof is inserted, in a forward or reverse orientation. In the case of a vector comprising one of the ORFs of the present invention, the vector may further comprise regulatory sequences, including for example, a promoter, operably linked to the ORF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

The isolated polynucleotide of the invention may be operably linked to an expression control sequence such as the pMT2 or pED expression vectors disclosed in Kaufman et al., *Nucleic Acids Res.* 19, 4485–4490 (1991), in order to produce the protein recombinantly. Many suitable expression control sequences are known in the art. General methods of expressing recombinant proteins are also known and are exemplified in R. Kaufman, *Methods in Enzymology* 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda PR, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an amino terminal identification peptide imparting desired characteristics, e.g., stabilization or simplified purification of expressed recombinant product. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotech, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

Polynucleotides of the invention can also be used to induce immune responses. For example, as described in Fan et al., *Nat. Biotech.* 17:870–872 (1999), incorporated herein by reference, nucleic acid sequences encoding a polypeptide may be used to generate antibodies against the encoded polypeptide following topical administration of naked plasmid DNA or following injection, and preferably intramuscular injection of the DNA. The nucleic acid sequences are preferably inserted in a recombinant expression vector and may be in the form of naked DNA.

4.3 Antisense

Another aspect of the invention pertains to isolated antisense nucleic acid molecules that are hybridizable to or complementary to the nucleic acid molecule comprising the nucleotide sequence of SEQ ID NO: 1–17, or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire coding strand, or to only a portion thereof. Nucleic acid molecules encoding fragments, homologs, derivatives and analogs of a protein of any of SEQ ID NO: 1–17 or antisense nucleic acids complementary to a nucleic acid sequence of SEQ ID NO: 1–17 are additionally provided.

In one embodiment, an antisense nucleic acid molecule is antisense to a "coding region" of the coding strand of a nucleotide sequence of the invention. The term "coding region" refers to the region of the nucleotide sequence comprising codons which are translated into amino acid residues. In another embodiment, the antisense nucleic acid molecule is antisense to a "noncoding region" of the coding strand of a nucleotide sequence of the invention. The term "noncoding region" refers to 5' and 3' sequences that flank the coding region that are not translated into amino acids (i.e., also referred to as 5' and 3' untranslated regions).

Given the coding strand sequences encoding a nucleic acid disclosed herein (e.g., SEQ ID NO: 1–17, antisense nucleic acids of the invention can be designed according to the rules of Watson and Crick or Hoogsteen base pairing. The antisense nucleic acid molecule can be complementary to the entire coding region of an mRNA, but more preferably is an oligonucleotide that is antisense to only a portion of the coding or noncoding region of an mRNA. For example, the antisense oligonucleotide can be complementary to the region surrounding the translation start site of an mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid(v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid(v), 5-methyl-2-thiouracil, 3-(3-amino-3-N-2-carboxypropyl)uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a protein according to the invention to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual α-units, the strands run parallel to each other (Gaultier et al. (1987) *Nucleic Acids Res* 15: 6625–6641). The antisense nucleic acid molecule can also comprise a 2'-o-methylribonucleotide (Inoue et al. (1987) *Nucleic Acids Res* 15: 6131–6148) or a chimeric RNA-DNA analogue (Inoue et al. (1987) *FEBS Lett* 215:.327–330).

4.4 Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave mRNA transcripts to thereby inhibit translation of an mRNA. A ribozyme having specificity for a nucleic acid of the invention can be designed based upon the nucleotide sequence of a DNA disclosed herein (i.e., SEQ ID NO: 1–17). For example, a derivative of Tetrahymena L-19 IVS RNA can be constructed in which the nucleotide sequence of the active site is complementary to the nucleotide sequence to be cleaved in a mRNA. See, e.g., Cech et al. U.S. Pat. No. 4,987,071; and Cech et al. U.S. Pat. No. 5,116,742. Alternatively, mRNA of the invention can be used to select a catalytic RNA having a specific ribonuclease activity from a pool of RNA molecules. See, e.g., Bartel et al., (1993) *Science* 261:1411–1418.

Alternatively, gene expression can be inhibited by targeting nucleotide sequences complementary to the regulatory region (e.g., promoter and/or enhancers) to form triple helical structures that prevent transcription of the gene in target cells. See generally, Helene. (1991) *Anticancer Drug Des.* 6: 569–84; Helene. et al. (1992) *Ann. N. Y. Acad. Sci.* 660:27–36; and Maher (1992) *Bioassays* 14: 807–15.

In various embodiments, the nucleic acids of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg Med Chem* 4: 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *PNAS* 93: 14670–675.

PNAs of the invention can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above).

In another embodiment, PNAs of the invention can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24:3357–63. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (1989) *Nucl Acid Res* 17: 5973–88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg Med Chem Lett* 5: 1119–11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553–6556; Lemaitre et al., 1987, *Proc. Natl. Acad. Sci.* 84:648–652; PCT Publication No. WO88/09810) or the blood-brain barrier (see, e.g., PCT Publication No. WO89/10134). In addition, oligonucleotides can be modified with hybridization triggered cleavage agents (See, e.g., Krol et al., 1988, *BioTechniques* 6:958–976) or intercalating agents. (See, e.g., Zon, 1988, *Pharm. Res.* 5: 539–549). To this end, the oligonucleotide may be conjugated to another molecule, e.g., a peptide, a hybridization triggered cross-linking agent, a transport agent, a hybridization-triggered cleavage agent, etc.

4.5 Hosts

The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the polynucleotides in the cell.

Knowledge of nucleic acid sequences allows for modification of cells to permit, or increase, expression of endogenous polypeptide. Cells can be modified (e.g., by homologous recombination) to provide increased polypeptide expression by replacing, in whole or in part, the naturally occurring promoter with all or part of a heterologous promoter so that the cells express the polypeptide at higher levels. The heterologous promoter is inserted in such a manner that it is operatively linked to the encoding sequences. See, for example, PCT International Publication No. WO94/12650, PCT International Publication No. WO92/20808, and PCT International Publication No. WO91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the coding sequence, amplification of the marker DNA by standard selection methods results in co-amplification of the desired protein coding sequences in the cells.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L. et al., *Basic Methods in Molecular Biology* (1986)). The host cells containing one of the polynucleotides of the invention, can be used in conventional manners to produce the gene product encoded by the isolated fragment (in the case of an ORF) or can be used to produce a heterologous protein under the control of the EMF.

Any host/vector system can be used to express one or more of the ORFs of the present invention. These include, but are not limited to, eukaryotic hosts such as HeLa cells, Cv-1 cell, COS cells, 293 cells, and Sf9 cells, as well as prokaryotic host such as *E. coli* and *B. subtilis*. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989), the disclosure of which is hereby incorporated by reference.

Various mammalian cell culture systems can also be employed to express recombinant protein. Examples of mammalian expression systems include the COS-7 lines of monkey kidney fibroblasts, described by Gluzman, Cell 23:175 (1981). Other cell lines capable of expressing a compatible vector are, for example, the C127, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro-culture of primary tissue, primary explants, HeLa cells, mouse L cells, BHK, HL-60, U937, HaK or Jurkat cells. Mammalian expression vectors will comprise an origin of replication, a suitable promoter and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

Alternatively, it may be possible to produce the protein in lower eukaryotes such as yeast or insects or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting. These sequence include polyadenylation signals, mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No.

PCT/US92/09627 (WO93/09222) by Selden et al.; and International Application No.

PCT/US90/06436 (WO91/06667) by Skoultchi et al., each of which is incorporated by reference herein in its entirety.

4.6 Polypeptides of the Invention

The isolated polypeptides of the invention include, but are not limited to, a polypeptide comprising: the amino acid sequences set forth as any one of SEQ ID NO: 18–34 or an amino acid sequence encoded by any one of the nucleotide sequences SEQ ID NOs: 1–17 or the corresponding full length or mature protein. Polypeptides of the invention also include polypeptides preferably with biological or immunological activity that are encoded by: (a) a polynucleotide having any one of the nucleotide sequences set forth in SEQ ID NOs: 1–17 or (b) polynucleotides encoding any one of the amino acid sequences set forth as SEQ ID NO: 1–17 or (c) polynucleotides that hybridize to the complement of the polynucleotides of either (a) or (b) under stringent hybridization conditions. The invention also provides biologically active or immunologically active variants of any of the amino acid sequences set forth as SEQ ID NO: 18–34 or the corresponding full length or mature protein; and "substantial equivalents" thereof (e.g., with at least about 65%, at least about 70%, at least about 75%, at least about 80%, at least about 85%, 86%, 87%, 88%, 89%, at least about 90%, 91%, 92%, 93%, 94%, typically at least 95%, 96%, 97%, more typically at least about 98%, or most typically at least about 99% amino acid identity) that retain biological activity. Polypeptides encoded by allelic variants may have a similar, increased, or decreased activity compared to polypeptides comprising SEQ ID NO: 18–34.

Fragments of the proteins of the present invention which are capable of exhibiting biological activity are also encompassed by the present invention. Fragments of the protein may be in linear form or they may be cyclized using known methods, for example, as described in H.

U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of protein binding sites.

The present invention also provides both full-length and mature forms (for example, without a signal sequence or precursor sequence) of the disclosed proteins. The protein coding sequence is identified in the sequence listing by translation of the disclosed nucleotide sequences. The mature form of such protein may be obtained by expression of a full-length polynucleotide in a suitable mammalian cell or other host cell. The sequence of the mature form of the protein is also determinable from the amino acid sequence of the full-length form. Where proteins of the present invention are membrane bound, soluble forms of the proteins are also provided. In such forms, part or all of the regions causing the proteins to be membrane bound are deleted so that the proteins are fully secreted from the cell in which they are expressed.

Protein compositions of the present invention may further comprise an acceptable carrier, such as a hydrophilic, e.g., pharmaceutically acceptable, carrier.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins.

A variety of methodologies known in the art can be utilized to obtain any one of the isolated polypeptides or proteins of the present invention. At the simplest level, the amino acid sequence can be synthesized using commercially available peptide synthesizers. The synthetically-constructed protein sequences, by virtue of sharing primary, secondary or tertiary structural and/or conformational characteristics with proteins may possess biological properties in common therewith, including protein activity. This technique is particularly useful in producing small peptides and fragments of larger polypeptides. Fragments are useful, for example, in generating antibodies against the native polypeptide. Thus, they may be employed as biologically active or immunological substitutes for natural, purified proteins in screening of therapeutic compounds and in immunological processes for the development of antibodies.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention.

The invention also relates to methods for producing a polypeptide comprising growing a culture of host cells of the invention in a suitable culture medium, and purifying the protein from the cells or the culture in which the cells are grown. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, or from a lysate prepared from the host cells and further purified. Preferred embodiments include those in which the protein produced by such process is a full length or mature form of the protein.

In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, *Protein Purification: Principles and Practice*, Springer-Verlag (1994); Sambrook, et al., in Molecular Cloning: *A Laboratory Manual*; Ausubel et al., *Current Protocols in Molecular Biology*. Polypeptide fragments that retain biological/immunological activity, include fragments comprising greater than about 100 amino acids, or greater than about 200 amino acids, and fragments that encode specific protein domains.

The purified polypeptides can be used in in vitro binding assays which are well known in the art to identify molecules which bind to the polypeptides. These molecules include but are not limited to, for e.g., small molecules, molecules from combinatorial libraries, antibodies or other proteins. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

In addition, the peptides of the invention or molecules capable of binding to the peptides may be complexed with toxins, e.g., ricin or cholera, or with other compounds that are toxic to cells. The toxin-binding molecule complex is then targeted to a tumor or other cell by the specificity of the binding molecule for SEQ ID NO: 18–34.

The protein of the invention may also be expressed as a product of transgenic animals, e.g., as a component of the milk of transgenic cows, goats, pigs, or sheep which are characterized by somatic or germ cells containing a nucleotide sequence encoding the protein.

The proteins provided herein also include proteins characterized by amino acid sequences similar to those of purified proteins but into which modification are naturally provided or deliberately engineered. For example, modifications, in the peptide or DNA sequence, can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein. Regions of the protein that are important for the protein function can be determined by various methods known in the art including the alanine-scanning method which involved systematic substitution of single or strings of amino acids with alanine, followed by testing the resulting alanine-containing variant for biological activity. This type of analysis determines the importance of the substituted amino acid(s) in biological activity. Regions of the protein that are important for protein function may be determined by the eMATRIX program.

Other fragments and derivatives of the sequences of proteins which would be expected to retain protein activity in whole or in part and are useful for screening or other immunological methodologies may also be easily made by those skilled in the art given the disclosures herein. Such modifications are encompassed by the present invention.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat™ kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl™ or Cibacrom blue 3GA Sepharose™; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX), or as a His tag. Kits for expression and purification of such fusion proteins are commercially available from New England BioLab (Beverly, Mass.), Pharmacia (Piscataway, N.J.) and Invitrogen, respectively. The protein can also be tagged with an epitope and subsequently purified by using a specific antibody directed to such epitope. One such epitope ("FLAG®") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The polypeptides of the invention include analogs (variants). This embraces fragments, as well as peptides in which one or more amino acids has been deleted, inserted, or substituted. Also, analogs of the polypeptides of the invention embrace fusions of the polypeptides or modifications of the polypeptides of the invention, wherein the polypeptide or analog is fused to another moiety or moieties, e.g., targeting moiety or another therapeutic agent. Such analogs may exhibit improved properties such as activity and/or stability. Examples of moieties which may be fused to the polypeptide or an analog include, for example, targeting moieties which provide for the delivery of polypeptide to pancreatic cells, e.g., antibodies to pancreatic cells, antibodies to immune cells such as T-cells, monocytes, dendritic cells, granulocytes, etc., as well as receptor and ligands expressed on pancreatic or immune cells. Other moieties which may be fused to the polypeptide include therapeutic agents which are used for treatment, for example, immunosuppressive drugs such as cyclosporin, SK506, azathioprine, CD3 antibodies and steroids. Also, polypeptides may be fused to immune modulators, and other cytokines such as alpha or beta interferon.

4.6.1 Determining Polypeptide and Polynucleotide Identity and Similarity

Preferred identity and/or similarity are designed to give the largest match between the sequences tested. Methods to determine identity and similarity are codified in computer programs including, but are not limited to, the GCG program package, including GAP (Devereux, J., et al., Nucleic Acids Research 12(1):387 (1984); Genetics Computer Group, University of Wisconsin, Madison, Wis.), BLASTP, BLASTN, BLASTX, FASTA (Altschul, S. F. et al., J. Molec. Biol. 215:403–410 (1990), PSI-BLAST (Altschul S. F. et al., Nucleic Acids Res. vol. 25, pp. 3389–3402, herein incorporated by reference), eMatrix software (Wu et al., J. Comp. Biol., Vol. 6, pp. 219–235 (1999), herein incorporated by reference), eMotif software (Nevill-Manning et al, ISMB-97, Vol. 4, pp. 202–209, herein incorporated by reference), pFam software (Sonnhammer et al., Nucleic Acids Res., Vol. 26(1), pp. 320–322 (1998), herein incorporated by reference) and the Kyte-Doolittle hydrophobocity prediction algorithm (J. Mol Biol, 157, pp. 105–31 (1982), incorporated herein by reference). The BLAST programs are publicly available from the National Center for Biotechnology Information (NCBI) and other sources (BLAST Manual, Altschul, S., et al. NCB NLM NIH Bethesda, Md. 20894; Altschul, S., et al., J. Mol. Biol. 215:403–410 (1990).

4.7 Chimeric and Fusion Proteins

The invention also provides chimeric or fusion proteins. As used herein, a "chimeric protein" or "fusion protein" comprises a polypeptide of the invention operatively linked to another polypeptide. Within a fusion protein the polypeptide according to the invention can correspond to all or a portion of a protein according to the invention. In one embodiment, a fusion protein comprises at least one biologically active portion of a protein according to the invention. In another embodiment, a fusion protein comprises at least two biologically active portions of a protein according to the invention. Within the fusion protein, the term "operatively linked" is intended to indicate that the polypeptide according to the invention and the other polypeptide are fused in-frame to each other. The polypeptide can be fused to the N-terminus or C-terminus, or to the middle.

For example, in one embodiment a fusion protein comprises a polypeptide according to the invention operably linked to the extracellular domain of a second protein.

In another embodiment, the fusion protein is a GST-fusion protein in which the polypeptide sequences of the invention are fused to the C-terminus of the GST (i.e., glutathione S-transferase) sequences.

In another embodiment, the fusion protein is an immunoglobulin fusion protein in which the polypeptide sequences according to the invention comprise one or more domains fused to sequences derived from a member of the immunoglobulin protein family. The immunoglobulin fusion proteins of the invention can be incorporated into pharmaceutical compositions and administered to a subject to inhibit an interaction between a ligand and a protein of the invention on the surface of a cell, to thereby suppress signal transduction in vivo. The immunoglobulin fusion proteins can be used to affect the bioavailability of a cognate ligand. Inhibition of the ligand/protein interaction may be useful therapeutically for both the treatment of proliferative and differentiative disorders, e.g., cancer as well as modulating (e.g., promoting or inhibiting) cell survival. Moreover, the immunoglobulin fusion proteins of the invention can be used as immunogens to produce antibodies in a subject, to purify ligands, and in screening assays to identify molecules that inhibit the interaction of a polypeptide of the invention with a ligand.

A chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) Current Protocols in Molecular Biology, John Wiley & Sons, 1992). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the protein of the invention.

4.8 Gene Therapy

Mutations in the polynucleotides of the invention gene may result in loss of normal function of the encoded protein. The invention thus provides gene therapy to restore normal activity of the polypeptides of the invention; or to treat disease states involving polypeptides of the invention. Delivery of a functional gene encoding polypeptides of the invention to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, Nature, supplement to vol. 392, no. 6679, pp.25–20 (1998). For additional reviews of gene therapy technology see Friedmann, Science, 244: 1275–1281 (1989); Verma, Scientific American: 68–84 (1990); and Miller, Nature, 357: 455–460 (1992). Introduction of any one of the nucleotides of the present invention or a gene encoding the polypeptides of the present invention can also be accomplished with extrachromosomal substrates (transient expression) or artificial chromosomes (stable expression). Cells may also be cultured ex vivo in the presence of proteins of the present invention in order to proliferate or to produce a desired effect on or activity in such cells. Treated cells can then be introduced in vivo for therapeutic purposes. Alternatively, it is contemplated that in other human disease states, preventing the expression of or inhibiting the activity of polypeptides of the invention will be useful in treating the disease states. It is contemplated that antisense therapy or gene therapy could be applied to negatively regulate the expression of polypeptides of the invention.

Other methods inhibiting expression of a protein include the introduction of antisense molecules to the nucleic acids of the present invention, their complements, or their translated RNA sequences, by methods known in the art. Further, the polypeptides of the present invention can be inhibited by using targeted deletion methods, or the insertion of a negative regulatory element such as a silencer, which is tissue specific.

The present invention still further provides cells genetically engineered in vivo to express the polynucleotides of the invention, wherein such polynucleotides are in operative association with a regulatory sequence heterologous to the host cell which drives expression of the polynucleotides in the cell. These methods can be used to increase or decrease the expression of the polynucleotides of the present invention.

Knowledge of DNA sequences provided by the invention allows for modification of cells to permit, increase, or decrease, expression of endogenous polypeptide. Cells can be modified (e.g., by homologous recombination) to provide increased polypeptide expression by replacing, in whole or in part, the naturally occurring promoter with all or part of a heterologous promoter so that the cells express the protein at higher levels. The heterologous promoter is inserted in such a manner that it is operatively linked to the desired protein encoding sequences. See, for example, PCT International Publication No. WO 94/12650, PCT International Publication No. WO 92/20808, and PCT International Publication No. WO 91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the desired protein coding sequence, amplification of the marker DNA by standard selection methods results in co-amplification of the desired protein coding sequences in the cells.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting. These sequences include polyadenylation signals, mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

4.9 Transgenic Animals

In preferred methods to determine biological functions of the polypeptides of the invention in vivo, one or more genes provided by the invention are either over expressed or inactivated in the germ line of animals using homologous recombination [Capecchi, Science 244:1288–1292 (1989)]. Animals in which the gene is over expressed, under the regulatory control of exogenous or endogenous promoter elements, are known as transgenic animals. Animals in which an endogenous gene has been inactivated by homologous recombination are referred to as "knockout" animals. Knockout animals, preferably non-human mammals, can be prepared as described in U.S. Pat. No. 5,557,032, incorporated herein by reference. Transgenic animals are useful to determine the roles polypeptides of the invention play in biological processes, and preferably in disease states. Transgenic animals are useful as model systems to identify compounds that modulate lipid metabolism. Transgenic animals, preferably non-human mammals, are produced using methods as described in U.S. Pat. No. 5,489,743 and PCT Publication No. WO94/28122, incorporated herein by reference.

Transgenic animals can be prepared wherein all or part of a promoter of the polynucleotides of the invention is either activated or inactivated to alter the level of expression of the polypeptides of the invention. Inactivation can be carried out using homologous recombination methods described above. Activation can be achieved by supplementing or even replacing the homologous promoter to provide for increased protein expression. The homologous promoter can be supplemented by insertion of one or more heterologous enhancer elements known to confer promoter activation in a particular tissue.

The polynucleotides of the present invention also make possible the development, through, e.g., homologous recombination or knock out strategies, of animals that fail to express polypeptides of the invention or that express a variant polypeptide. Such animals are useful as models for studying the in vivo activities of polypeptide as well as for studying modulators of the polypeptides of the invention.

In preferred methods to determine biological functions of the polypeptides of the invention in vivo, one or more genes provided by the invention are either over expressed or inactivated in the germ line of animals using homologous recombination [Capecchi, Science 244:1288–1292 (1989)]. Animals in which the gene is over expressed, under the regulatory control of exogenous or endogenous promoter elements, are known as transgenic animals. Animals in which an endogenous gene has been inactivated by homologous recombination are referred to as "knockout" animals. Knockout animals, preferably non-human mammals, can be prepared as described in U.S. Pat. No. 5,557,032, incorporated herein by reference. Transgenic animals are useful to determine the roles polypeptides of the invention play in biological processes, and preferably in disease states. Transgenic animals are useful as model systems to identify compounds that modulate lipid metabolism. Transgenic animals, preferably non-human mammals, are produced using methods as described in U.S. Pat. No. 5,489,743 and PCT Publication No. WO94/28122, incorporated herein by reference.

Transgenic animals can be prepared wherein all or part of the polynucleotides of the invention promoter is either activated or inactivated to alter the level of expression of the polypeptides of the invention. Inactivation can be carried out using homologous recombination methods described above. Activation can be achieved by supplementing or even replacing the homologous promoter to provide for increased protein expression. The homologous promoter can be supplemented by insertion of one or more heterologous enhancer elements known to confer promoter activation in a particular tissue.

4.10 Uses and Biological Activity

The polynucleotides and proteins of the present invention are expected to exhibit one or more of the uses or biological activities (including those associated with assays cited herein) identified herein. Uses or activities described for proteins of the present invention may be provided by administration or use of such proteins or of polynucleotides encoding such proteins (such as, for example, in gene therapies or vectors suitable for introduction of DNA). The mechanism underlying the particular condition or pathology will dictate whether the polypeptides of the invention, the polynucleotides of the invention or modulators (activators or inhibitors) thereof would be beneficial to the subject in need of treatment. Thus, "therapeutic compositions of the invention" include compositions comprising isolated polynucleotides (including recombinant DNA molecules, cloned genes and degenerate variants thereof) or polypeptides of the invention (including full length protein, mature protein and truncations or domains thereof), or compounds and other substances that modulate the overall activity of the target gene products, either at the level of target gene/protein expression or target protein activity. Such modulators include polypeptides, analogs, (variants), including fragments and fusion proteins, antibodies and other binding proteins; chemical compounds that directly or indirectly activate or inhibit the polypeptides of the invention (identified, e.g., via drug screening assays as described herein); antisense polynucleotides and polynucleotides suitable for triple helix formation; and in particular antibodies or other binding partners that specifically recognize one or more epitopes of the polypeptides of the invention.

The polypeptides of the present invention may likewise be involved in cellular activation or in one of the other physiological pathways described herein.

4.10.1 Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The polypeptides provided by the present invention can similarly be used in assays to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding polypeptide is preferentially expressed (either constitutively or at a particular stage of tissue differentiation or development or in a disease state); and, of course, to isolate correlative receptors or ligands. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

4.10.2 Nutritional Uses

Polynucleotides and polypeptides of the present invention can also be used as nutritional sources or supplements. Such uses include without limitation use as a protein or amino acid supplement, use as a carbon source, use as a nitrogen source and use as a source of carbohydrate. In such cases the polypeptide or polynucleotide of the invention can be added to the feed of a particular organism or can be administered as a separate solid or liquid preparation, such as in the form of powder, pills, solutions, suspensions or capsules. In the case of microorganisms, the polypeptide or polynucleotide of the invention can be added to the medium in or on which the microorganism is cultured.

4.10.3 Cytokine and Cell Proliferation/differentiation Activity

A polypeptide of the present invention may exhibit activity relating to cytokine, cell proliferation (either inducing or inhibiting) or cell differentiation (either inducing or inhibiting) activity or may induce production of other cytokines in certain cell populations. A polynucleotide of the invention can encode a polypeptide exhibiting such attributes. Many protein factors discovered to date, including all known cytokines, have exhibited activity in one or more factor-dependent cell proliferation assays, and hence the assays serve as a convenient confirmation of cytokine activity. The activity of therapeutic compositions of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e, CMK, HUVEC, and Caco. Therapeutic compositions of the invention can be used in the following:

Assays for T-cell or thymocyte proliferation include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., I. Immunol. 149:3778–3783, 1992; Bowman et al., I. Immunol. 152:1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1–3.12.14, John Wiley and Sons, Toronto. 1994; and Measurement of mouse and human interleukin-γ, Schreiber, R. D. In Current Protocols in Immunology. J. E. e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6—Nordan, R. In Current Protocols in Immunology. J. E. Coligan eds. Vol 1 pp. 6.6.1–6.6.5, John Wiley and Sons, Toronto. 1991; Smith et al., Proc. Natl. Aced. Sci. U.S.A. 83:1857–1861, 1986; Measurement of human Interleukin 11—Bennett, F., Giannotti, J., Clark, S. C. and Turner, K. J. In Current Protocols in Immunology. J. E. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In Current Protocols in Immunology. J. E. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

4.10.4 Stem Cell Growth Factor Activity

A polypeptide of the present invention may exhibit stem cell growth factor activity and be involved in the proliferation, differentiation and survival of pluripotent and totipotent stem cells including primordial germ cells, embryonic stem cells, hematopoietic stem cells and/or germ line stem cells. Administration of the polypeptide of the invention to stem cells in vivo or ex vivo is expected to maintain and expand cell populations in a totipotential or pluripotential state which would be useful for re-engineering damaged or diseased tissues, transplantation, manufacture of bio-pharmaceuticals and the development of bio-sensors. The ability to produce large quantities of human cells has important working applications for the production of human proteins which currently must be obtained from non-human sources or donors, implantation of cells to treat diseases such as Parkinson's, Alzheimer's and other neurodegenerative diseases; tissues for grafting such as bone marrow, skin, cartilage, tendons, bone, muscle (including cardiac muscle), blood vessels, cornea, neural cells, gastrointestinal cells and others; and organs for transplantation such as kidney, liver, pancreas (including islet cells), heart and lung.

It is contemplated that multiple different exogenous growth factors and/or cytokines may be administered in combination with the polypeptide of the invention to achieve the desired effect, including any of the growth factors listed herein, other stem cell maintenance factors, and specifically including stem cell factor (SCF), leukemia inhibitory factor (LIF), Flt-3 ligand (Flt-3L), any of the interleukins, recombinant soluble IL-6 receptor fused to IL-6, macrophage inflammatory protein 1-alpha (MIP-1-alpha), G-CSF, GM-CSF, thrombopoietin (TPO), platelet factor 4 (PF-4), platelet-derived growth factor (PDGF), neural growth factors and basic fibroblast growth factor (bFGF).

Since totipotent stem cells can give rise to virtually any mature cell type, expansion of these cells in culture will facilitate the production of large quantities of mature cells. Techniques for culturing stem cells are known in the art and administration of polypeptides of the invention, optionally with other growth factors and/or cytokines, is expected to enhance the survival and proliferation of the stem cell populations. This can be accomplished by direct administration of the polypeptide of the invention to the culture medium. Alternatively, stroma cells transfected with a polynucleotide that encodes for the polypeptide of the invention can be used as a feeder layer for the stem cell populations in culture or in vivo. Stromal support cells for feeder layers may include embryonic bone marrow fibroblasts, bone marrow stromal cells, fetal liver cells, or cultured embryonic fibroblasts (see U.S. Pat. No. 5,690,926).

Stem cells themselves can be transfected with a polynucleotide of the invention to induce autocrine expression of the polypeptide of the invention. This will allow for generation of undifferentiated totipotential/pluripotential stem cell lines that are useful as is or that can then be differentiated into the desired mature cell types. These stable cell lines can also serve as a source of undifferentiated totipotential/pluripotential mRNA to create cDNA libraries and templates for polymerase chain reaction experiments. These studies would allow for the isolation and identification of differentially expressed genes in stem cell populations that regulate stem cell proliferation and/or maintenance.

Expansion and maintenance of totipotent stem cell populations will be useful in the treatment of many pathological conditions. For example, polypeptides of the present invention may be used to manipulate stem cells in culture to give rise to neuroepithelial cells that can be used to augment or replace cells damaged by illness, autoimmune disease, accidental damage or genetic disorders. The polypeptide of the invention may be useful for inducing the proliferation of neural cells and for the regeneration of nerve and brain tissue, i.e. for the treatment of central and peripheral nervous system diseases and neuropathies, as well as mechanical and traumatic disorders which involve degeneration, death or trauma to neural cells or nerve tissue. In addition, the expanded stem cell populations can also be genetically altered for gene therapy purposes and to decrease host rejection of replacement tissues after grafting or implantation.

Expression of the polypeptide of the invention and its effect on stem cells can also be manipulated to achieve controlled differentiation of the stem cells into more differentiated cell types. A broadly applicable method of obtaining pure populations of a specific differentiated cell type from undifferentiated stem cell populations involves the use of a cell-type specific promoter driving a selectable marker. The selectable marker allows only cells of the desired type to survive. For example, stem cells can be induced to differentiate into cardiomyocytes (Wobus et al., Differentiation, 48: 173–182, (1991); Klug et al., J. Clin. Invest., 98(1): 216–224, (1998 or skeletal muscle cells (Browder, L. W. In: *Principles of Tissue Engineering* eds. Lanza et al., Academic Press (1997)). Alternatively, directed differentiation of stem cells can be accomplished by culturing the stem cells in the presence of a differentiation factor such as retinoic acid and an antagonist of the polypeptide of the invention which would inhibit the effects of endogenous stem cell factor activity and allow differentiation to proceed.

In vitro cultures of stem cells can be used to determine if the polypeptide of the invention exhibits stem cell growth factor activity. Stem cells are isolated from any one of various cell sources (including hematopoietic stem cells and embryonic stem cells) and cultured on a feeder layer, as described by Thompson et al. Proc. Natl. Acad. Sci, U.S.A., 92: 7844–7848 (1995), in the presence of the polypeptide of the invention alone or in combination with other growth factors or cytokines. The ability of the polypeptide of the invention to induce stem cells proliferation is determined by colony formation on semi-solid support e.g. as described by Bernstein et al., Blood, 77: 2316–2321 (1991).

4.10.5 Hematopoiesis Regulating Activity

A polypeptide of the present invention may be involved in regulation of hematopoiesis and, consequently, in the treatment of myeloid or lymphoid cell disorders. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

Therapeutic compositions of the invention can be used in the following:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lympho-hematopoiesis) include, without limitation, those described in: Methylcellulose colony forming assays, Freshney, M. G. In Culture of Hematopoietic Cells. R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In Culture of Hematopoietic Cells. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In Culture of Hematopoietic Cells. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In Culture of Hematopoietic Cells. R. I. Freshney, et al. eds. Vol pp. 163–179, Wiley-Liss, Inc., New York, N.Y. 1994; Long term culture initiating cell assay, Sutherland, H. J. In Culture of Hematopoietic Cells. R. I. Freshney, et al. eds. Vol pp. 139–162, Wiley-Liss, Inc., New York, N.Y. 1994.

4.10.6 Tissue Growth Activity

A polypeptide of the present invention also may be involved in bone, cartilage, tendon, ligament and/or nerve tissue growth or regeneration, as well as in wound healing and tissue repair and replacement, and in healing of burns, incisions and ulcers.

A polypeptide of the present invention which induces cartilage and/or bone growth in circumstances where bone is not normally formed, has application in the healing of bone fractures and cartilage damage or defects in humans and other animals. Compositions of a polypeptide, antibody, binding partner, or other modulator of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A polypeptide of this invention may also be involved in attracting bone-forming cells, stimulating growth of bone-forming cells, or inducing differentiation of progenitors of bone-forming cells. Treatment of osteoporosis, osteoarthritis, bone degenerative disorders, or periodontal disease, such as through stimulation of bone and/or cartilage repair or by blocking inflammation or processes of tissue destruction (collagenase activity, osteoclast activity, etc.) mediated by inflammatory processes may also be possible using the composition of the invention.

Another category of tissue regeneration activity that may involve the polypeptide of the present invention is tendon/ligament formation. Induction of tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The compositions of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a composition may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a composition of the invention.

Compositions of the invention may also be useful to promote better or faster closure of non-healing wounds, including without limitation pressure ulcers, ulcers associated with vascular insufficiency, surgical and traumatic wounds, and the like.

Compositions of the present invention may also be involved in the generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring may allow normal tissue to regenerate. A polypeptide of the present invention may also exhibit angiogenic activity.

A composition of the present invention may also be useful for gut protection or regeneration and treatment of lung or liver fibrosis, reperfusion injury in various tissues, and conditions resulting from systemic cytokine damage.

A composition of the present invention may also be useful for promoting or inhibiting differentiation of tissues described above from precursor tissues or cells; or for inhibiting the growth of tissues described above.

Therapeutic compositions of the invention can be used in the following:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, Epidermal Wound Healing, pps. 71–112 (Maibach, H. I. and Rovee, D. T., eds.), Year Book Medical Publishers, Inc., Chicago, as modified by Eaglstein and Mertz, J. Invest. Dermatol 71:382–84 (1978).

4.10.7 Immune Stimulating or Suppressing Activity

A polypeptide of the present invention may also exhibit immune stimulating or immune suppressing activity, including without limitation the activities for which assays are described herein. A polynucleotide of the invention can encode a polypeptide exhibiting such activities. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpes viruses, mycobacteria, Leishmania spp., malaria spp. and various fungal infections such as candidiasis. Of course, in this regard, proteins of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein (or antagonists thereof, including antibodies) of the present invention may also to be useful in the treatment of allergic reactions and conditions (e.g., anaphylaxis, serum sickness, drug reactions, food allergies, insect venom allergies, mastocytosis, allergic rhinitis, hypersensitivity pneumonitis, urticaria, angioedema, eczema, atopic dermatitis, allergic contact dermatitis, erythema multiforme, Stevens-Johnson syndrome, allergic conjunctivitis, atopic keratoconjunctivitis, venereal keratoconjunctivitis, giant papillary conjunctivitis and contact allergies), such as asthma (particularly allergic asthma) or other respiratory problems. Other conditions, in which immune suppression is desired (including, for example, organ transplantation), may also be treatable using a protein (or antagonists thereof) of the present invention. The therapeutic effects of the polypeptides or antagonists thereof on allergic reactions can be evaluated by in vivo animals models such as the cumulative contact enhancement test (Lastbom et al., Toxicology 125: 59–66, 1998), skin prick test (Hoffmann et al., Allergy 54: 446–54, 1999), guinea pig skin sensitization test (Vohr et al., Arch. Toxocol. 73: 501–9), and murine local lymph node assay (Kimber et al., J. Toxicol. Environ. Health 53: 563–79).

Using the proteins of the invention it may also be possible to modulate immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a therapeutic composition of the invention may prevent cytokine synthesis by immune cells, such as T cells, and thus acts as an immunosuppressant. Moreover, a lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular therapeutic compositions in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of therapeutic compositions of the invention on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block stimulation of T cells can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (e.g., a B lymphocyte antigen function), as a means of up regulating immune responses, may also be useful in therapy. Upregulation of immune responses may be in the form of enhancing an existing immune response or eliciting an initial immune response. For example, enhancing an immune response may be useful in cases of viral infection, including systemic viral diseases such as influenza, the common cold, and encephalitis.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

A polypeptide of the present invention may provide the necessary stimulation signal to T cells to induce a T cell mediated immune response against the transfected tumor cells. In addition, tumor cells which lack MHC class I or MHC class II molecules, or which fail to reexpress sufficient mounts of MHC class I or MHC class II molecules, can be transfected with nucleic acid encoding all or a portion of (e.g., a cytoplasmic-domain truncated portion) of an MHC class I alpha chain protein and $\beta_2$ microglobulin protein or an MHC class II alpha chain protein and an MHC class II beta chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., I. Immunol. 137:3494–3500, 1986; Takai et al:, J. Immunol. 140:508–512, 1988; Bowman et al., J. Virology 61:1992–1998; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E. e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. USA 88:7548–7551, 1991.

4.10.8 Activin/inhibin Activity

A polypeptide of the present invention may also exhibit activin- or inhibin-related activities. A polynucleotide of the invention may encode a polypeptide exhibiting such characteristics. Inhibins are characterized by their ability to inhibit the release of follicle stimulating hormone (FSH), while activins and are characterized by their ability to stimulate the release of follicle stimulating hormone (FSH). Thus, a polypeptide of the present invention, alone or in heterodimers with a member of the inhibin family, may be useful as a contraceptive based on the ability of inhibins to decrease fertility in female mammals and decrease spermatogenesis in male mammals. Administration of sufficient amounts of other inhibins can induce infertility in these mammals. Alternatively, the polypeptide of the invention, as a homodimer or as a heterodimer with other protein subunits of the inhibin group, may be useful as a fertility inducing therapeutic, based upon the ability of activin molecules in stimulating FSH release from cells of the anterior pituitary. See, for example, U.S. Pat. No. 4,798,885. A polypeptide of the invention may also be useful for advancement of the onset of fertility in sexually immature mammals, so as to increase the lifetime reproductive performance of domestic animals such as, but not limited to, cows, sheep and pigs.

The activity of a polypeptide of the invention may, among other means, be measured by the following methods.

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

4.10.9 Chemotactic/chemokinetic Activity

A polypeptide of the present invention may be involved in chemotactic or chemokinetic activity for mammalian cells, including, for example, monocytes, fibroblasts, neutrophils, T-cells, mast cells, eosinophils, epithelial and/or endothelial cells. A polynucleotide of the invention can encode a polypeptide exhibiting such attributes. Chemotactic and chemokinetic receptor activation can be used to mobilize or attract a desired cell population to a desired site of action. Chemotactic or chemokinetic compositions (e.g. proteins, antibodies, binding partners, or modulators of the invention) provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

Therapeutic compositions of the invention can be used in the following:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Marguiles, E. M. Shevach, W. Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25:1744–1748; Gruber et al. J. of Immunol. 152:5860–5867, 1994; Johnston et al. J. of Immunol. 153:1762–1768, 1994.

4.10.10 Hemostatic and Thrombolytic Activity

A polypeptide of the invention may also be involved in hemostatis or thrombolysis or thrombosis. A polynucleotide of the invention can encode a polypeptide exhibiting such attributes. Compositions may be useful in treatment of various coagulation disorders (including hereditary disorders, such as hemophilias) or to enhance coagulation and other hemostatic events in treating wounds resulting from trauma, surgery or other causes. A composition of the invention may also be useful for dissolving or inhibiting formation of thromboses and for treatment and prevention of conditions resulting therefrom (such as, for example, infarction of cardiac and central nervous system vessels (e.g., stroke).

Therapeutic compositions of the invention can be used in the following:

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

4.10.11 Cancer Diagnosis and Therapy

Polypeptides of the invention may be involved in cancer cell generation, proliferation or metastasis. Detection of the presence or amount of polynucleotides or polypeptides of the invention may be useful for the diagnosis and/or prognosis of one or more types of cancer. For example, the presence or increased expression of a polynucleotide/ polypeptide of the invention may indicate a hereditary risk of cancer, a precancerous condition, or an ongoing malignancy. Conversely, a defect in the gene or absence of the polypeptide may be associated with a cancer condition. Identification of single nucleotide polymorphisms associated with cancer or a predisposition to cancer may also be useful for diagnosis or prognosis.

Cancer treatments promote tumor regression by inhibiting tumor cell proliferation, inhibiting angiogenesis (growth of new blood vessels that is necessary to support tumor growth) and/or prohibiting metastasis by reducing tumor cell motility or invasiveness. Therapeutic compositions of the invention may be effective in adult and pediatric oncology including in solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, astrocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Karposi's sarcoma.

Polypeptides, polynucleotides, or modulators of polypeptides of the invention (including inhibitors and stimulators of the biological activity of the polypeptide of the invention) may be administered to treat cancer. Therapeutic compositions can be administered in therapeutically effective dosages alone or in combination with adjuvant cancer therapy such as surgery, chemotherapy, radiotherapy, thermotherapy, and laser therapy, and may provide a beneficial effect, e.g. reducing tumor size, slowing rate of tumor growth, inhibiting metastasis, or otherwise improving overall clinical condition, without necessarily eradicating the cancer.

The composition can also be administered in therapeutically effective amounts as a portion of an anti-cancer cocktail. An anti-cancer cocktail is a mixture of the polypeptide or modulator of the invention with one or more anti-cancer drugs in addition to a pharmaceutically acceptable carrier for delivery. The use of anti-cancer cocktails as a cancer treatment is routine. Anti-cancer drugs that are well known in the art and can be used as a treatment in combination with the polypeptide or modulator of the invention include: Actinomycin D, Aminoglutethimide, Asparaginase, Bleomycin, Busulfan, Carboplatin, Carmustine, Chlorambucil, Cisplatin (cis-DDP), Cyclophosphamide, Cytarabine HCl (Cytosine arabinoside), Dacarbazine, Dactinomycin, Daunorubicin HCl, Doxorubicin HCl, Estramustine phosphate sodium, Etoposide (V16-213), Floxuridine, 5-Fluorouracil (5-Fu), Flutamide, Hydroxyurea (hydroxycarbamide), Ifosfamide, Interferon Alpha-2a, Interferon Alpha-2b, Leuprolide acetate (LHRH-releasing factor analog), Lomustine, Mechlorethamine HCl (nitrogen mustard), Melphalan, Mercaptopurine, Mesna, Methotrexate (MTX), Mitomycin, Mitoxantrone HCl, Octreotide, Plicamycin, Procarbazine HCl, Streptozocin, Tamoxifen citrate, Thioguanine, Thiotepa, Vinblastine sulfate, Vincristine sulfate, Amsacrine, Azacitidine, Hexamethylmelamine, Interleukin-2, Mitoguazone, Pentostatin, Semustine, Teniposide, and Vindesine sulfate.

In addition, therapeutic compositions of the invention may be used for prophylactic treatment of cancer. There are hereditary conditions and/or environmental situations (e.g. exposure to carcinogens) known in the art that predispose an individual to developing cancers. Under these circumstances, it may be beneficial to treat these individuals with therapeutically effective doses of the polypeptide of the invention to reduce the risk of developing cancers.

In vitro models can be used to determine the effective doses of the polypeptide of the invention as a potential cancer treatment. These in vitro models include proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., J. Natl. Can. Inst., 52: 921–30 (1974), mobility and invasive potential of tumor cells in Boyden Chamber assays as described in Pilkington et al., Anticancer Res., 17: 4107–9 (1997), and angiogenesis assays such as induction of vascularization of the chick chorioallantoic membrane or induction of vascular endothelial cell migration as described in Ribatta et al., Intl. J. Dev. Biol., 40: 1189–97 (1999) and Li et al., Clin. Exp. Metastasis, 17:423–9 (1999), respectively. Suitable tumor cells lines are available, e.g. from American Type Tissue Culture Collection catalogs.

4.10.12 Receptor/ligand Activity

A polypeptide of the present invention may also demonstrate activity as receptor, receptor ligand or inhibitor or agonist of receptor/ligand interactions. A polynucleotide of the invention can encode a polypeptide exhibiting such characteristics. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectins integrins and their ligands) and receptor/ligand pairs involved in antigen presentation, antigen recognition and development of cellular and humoral immune responses. Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a polypeptide of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med.

169:149–160 1989; Stoltenborg et al., J. Immunol. Methods 175:59–68, 1994; Stitt et al., Cell 80:661–670, 1995.

By way of example, the polypeptides of the invention may be used as a receptor for a ligand(s) thereby transmitting the biological activity of that ligand(s). Ligands may be identified through binding assays, affinity chromatography, dihybrid screening assays, BIAcore assays, gel overlay assays, or other methods known in the art.

Studies characterizing drugs or proteins as agonist or antagonist or partial agonists or a partial antagonist require the use of other proteins as competing ligands. The polypeptides of the present invention or ligand(s) thereof may be labeled by being coupled to radioisotopes, colorimetric molecules or a toxin molecules by conventional methods. ("Guide to Protein Purification" Murray P. Deutscher (ed) Methods in Enzymology Vol. 182 (1990) Academic Press, Inc. San Diego). Examples of radioisotopes include, but are not limited to, tritium and carbon-14 . Examples of colorimetric molecules include, but are not limited to, fluorescent molecules such as fluorescamine, or rhodamine or other calorimetric molecules. Examples of toxins include, but are not limited, to ricin.

4.10.13 Drug Screening

This invention is particularly useful for screening chemical compounds by using the novel polypeptides or binding fragments thereof in any of a variety of drug screening techniques. The polypeptides or fragments employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or a fragment thereof. Drugs are screened against such transformed cells in competitive binding assays. Such cells, either in viable or fixed form, can be used for standard binding assays. One may measure, for example, the formation of complexes between polypeptides of the invention or fragments and the agent being tested or examine the diminution in complex formation between the novel polypeptides and an appropriate cell line, which are well known in the art.

Sources for test compounds that may be screened for ability to bind to or modulate (i.e., increase or decrease) the activity of polypeptides of the invention include (1) inorganic and organic chemical libraries, (2) natural product libraries, and (3) combinatorial libraries comprised of either random or mimetic peptides, oligonucleotides or organic molecules.

Chemical libraries may be readily synthesized or purchased from a number of commercial sources, and may include structural analogs of known compounds or compounds that are identified as "hits" or "leads" via natural product screening.

The sources of natural product libraries are microorganisms (including bacteria and fungi), animals, plants or other vegetation, or marine organisms, and libraries of mixtures for screening may be created by: (1) fermentation and extraction of broths from soil, plant or marine microorganisms or (2) extraction of the organisms themselves. Natural product libraries include polyketides, non-ribosomal peptides, and (non-naturally occurring) variants thereof. For a review, see Science 282:63–68 (1998).

Combinatorial libraries are composed of large numbers of peptides, oligonucleotides or organic compounds and can be readily prepared by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701–707 (1997). For reviews and examples of peptidomimetic libraries, see Al-Obeidi et al., Mol. Biotechnol, 9(3):205–23 (1998); Hruby et al., Curr Opin Chem Biol, 1(1):114–19 (1997); Dorner et al., Bioorg Med Chem, 4(5):709–15 (1996) (alkylated dipeptides).

Identification of modulators through use of the various libraries described herein permits modification of the candidate "hit" (or "lead") to optimize the capacity of the "hit" to bind a polypeptide of the invention. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

The binding molecules thus identified may be complexed with toxins, e.g., ricin or cholera, or with other compounds that are toxic to cells such as radioisotopes. The toxin-binding molecule complex is then targeted to a tumor or other cell by the specificity of the binding molecule for a polypeptide of the invention. Alternatively, the binding molecules may be complexed with imaging agents for targeting and imaging purposes.

4.10.14 Assay for Receptor Activity

The invention also provides methods to detect specific binding of a polypeptide e.g. a ligand or a receptor. The art provides numerous assays particularly useful for identifying previously unknown binding partners for receptor polypeptides of the invention. For example, expression cloning using mammalian or bacterial cells, or dihybrid screening assays can be used to identify polynucleotides encoding binding partners. As another example, affinity chromatography with the appropriate immobilized polypeptide of the invention can be used to isolate polypeptides that recognize and bind polypeptides of the invention. There are a number of different libraries used for the identification of compounds, and in particular small molecules, that modulate (i.e., increase or decrease) biological activity of a polypeptide of the invention. Ligands for receptor polypeptides of the invention can also be identified by adding exogenous ligands, or cocktails of ligands to two cells populations that are genetically identical except for the expression of the receptor of the invention: one cell population expresses the receptor of the invention whereas the other does not. The response of the two cell populations to the addition of ligands(s) are then compared. Alternatively, an expression library can be co-expressed with the polypeptide of the invention in cells and assayed for an autocrine response to identify potential ligand(s). As still another example, BIAcore assays, gel overlay assays, or other methods known in the art can be used to identify binding partner polypeptides, including, (1) organic and inorganic chemical libraries, (2) natural product libraries, and (3) combinatorial libraries comprised of random peptides, oligonucleotides or organic molecules.

The role of downstream intracellular signaling molecules in the signaling cascade of the polypeptide of the invention can be determined. For example, a chimeric protein in which the cytoplasmic domain of the polypeptide of the invention is fused to the extracellular portion of a protein, whose ligand has been identified, is produced in a host cell. The cell is then incubated with the ligand specific for the extracellular portion of the chimeric protein, thereby activating the chimeric receptor. Known downstream proteins involved in intracellular signaling can then be assayed for expected modifications i.e. phosphorylation. Other methods known to those in the art can also be used to identify signaling molecules involved in receptor activity.

4.10.15 Anti-inflammatory Activity

Compositions of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Compositions with such activities can be used to treat inflammatory conditions including chronic or acute conditions), including without limitation intimation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Compositions of the invention may also be useful to treat anaphylaxis and hypersensitivity to an antigenic substance or material. Compositions of this invention may be utilized to prevent or treat conditions such as, but not limited to, sepsis, acute pancreatitis, endotoxin shock, cytokine induced shock, rheumatoid arthritis, chronic inflammatory arthritis, pancreatic cell damage from diabetes mellitus type 1, graft versus host disease, inflammatory bowel disease, inflammation associated with pulmonary disease, other autoimmune disease or inflammatory disease, an antiproliferative agent such as for acute or chronic mylegenous leukemia or in the prevention of premature labor secondary to intrauterine infections.

4.10.16 Leukemias

Leukemias and related disorders may be treated or prevented by administration of a therapeutic that promotes or inhibits function of the polynucleotides and/or polypeptides of the invention. Such leukemias and related disorders include but are not limited to acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia and chronic lymphocytic leukemia (for a review of such disorders, see Fishman et al., 1985, Medicine, 2d Ed., J. B. Lippincott Co., Philadelphia).

4.10.17 Nervous System Disorders

Nervous system disorders, involving cell types which can be tested for efficacy of intervention with compounds that modulate the activity of the polynucleotides and/or polypeptides of the invention, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(iv) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(v) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vi) neurological lesions associated with systemic diseases including but not limited to diabetes (diabetic neuropathy, Bell's palsy), systemic lupus erythematosus, carcinoma, or sarcoidosis;

(vii) lesions caused by toxic substances including alcohol, lead, or particular neurotoxins; and (viii) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons. For example, and not by way of limitation, therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo.

Such effects may be measured by any method known in the art. In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

4.10.18 Other Activities

A polypeptide of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, co-factors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

4.10.19 Identification of Polymorphisms

The demonstration of polymorphisms makes possible the identification of such polymorphisms in human subjects and the pharmacogenetic use of this information for diagnosis and treatment. Such polymorphisms may be associated with, e.g., differential predisposition or susceptibility to various disease states (such as disorders involving inflammation or immune response) or a differential response to drug administration, and this genetic information can be used to tailor preventive or therapeutic treatment appropriately. For example, the existence of a polymorphism associated with a predisposition to inflammation or autoimmune disease makes possible the diagnosis of this condition in humans by identifying the presence of the polymorphism.

Polymorphisms can be identified in a variety of ways known in the art which all generally involve obtaining a sample from a patient, analyzing DNA from the sample, optionally involving isolation or amplification of the DNA, and identifying the presence of the polymorphism in the DNA. For example, PCR may be used to amplify an appropriate fragment of genomic DNA which may then be sequenced. Alternatively, the DNA may be subjected to allele-specific oligonucleotide hybridization (in which appropriate oligonucleotides are hybridized to the DNA under conditions permitting detection of a single base mismatch) or to a single nucleotide extension assay (in which an oligonucleotide that hybridizes immediately adjacent to the position of the polymorphism is extended with one or more labeled nucleotides). In addition, traditional restriction fragment length polymorphism analysis (using restriction enzymes that provide differential digestion of the genomic DNA depending on the presence or absence of the polymorphism) may be performed. Arrays with nucleotide sequences of the present invention can be used to detect polymorphisms. The array can comprise modified nucleotide sequences of the present invention in order to detect the nucleotide sequences of the present invention. In the alternative, any one of the nucleotide sequences of the present invention can be placed on the array to detect changes from those sequences.

Alternatively a polymorphism resulting in a change in the amino acid sequence could also be detected by detecting a corresponding change in amino acid sequence of the protein, e.g., by an antibody specific to the variant sequence.

4.10.20 Arthritis and Inflammation

The immunosuppressive effects of the compositions of the invention against rheumatoid arthritis is determined in an experimental animal model system. The experimental model system is adjuvant induced arthritis in rats, and the protocol is described by J. Holoshitz, et at., 1983, Science, 219:56, or by B. Waksman et al., 1963, Int. Arch. Allergy Appl. Immunol., 23:129. Induction of the disease can be caused by a single injection, generally intradermally, of a suspension of killed Mycobacterium tuberculosis in complete Freund's adjuvant (CFA). The route of injection can vary, but rats may be injected at the base of the tail with an adjuvant mixture. The polypeptide is administered in phosphate buffered solution (PBS) at a dose of about 1–5 mg/kg. The control consists of administering PBS only.

The procedure for testing the effects of the test compound would consist of intradermally injecting killed Mycobacterium tuberculosis in CFA followed by immediately administering the test compound and subsequent treatment every other day until day 24. At 14, 15, 18, 20, 22, and 24 days after injection of Mycobacterium CFA, an overall arthritis score may be obtained as described by J. Holoskitz above. An analysis of the data would reveal that the test compound would have a dramatic affect on the swelling of the joints as measured by a decrease of the arthritis score.

4.11 Therapeutic Methods

The compositions (including polypeptide fragments, analogs, variants and antibodies or other binding partners or modulators including antisense polynucleotides) of the invention have numerous applications in a variety of therapeutic methods. Examples of therapeutic applications include, but are not limited to, those exemplified herein.

4.11.1 Example

One embodiment of the invention is the administration of an effective amount of the polypeptides or other composition of the invention to individuals affected by a disease or disorder that can be modulated by regulating the peptides of the invention. While the mode of administration is not particularly important, parenteral administration is preferred. An exemplary mode of administration is to deliver an intravenous bolus. The dosage of the polypeptides or other composition of the invention will normally be determined by the prescribing physician. It is to be expected that the dosage will vary according to the age, weight, condition and response of the individual patient. Typically, the amount of polypeptide administered per dose will be in the range of about 0.01 µg/kg to 100 mg/kg of body weight, with the preferred dose being about 0.1 µg/kg to 10 mg/kg of patient body weight. For parenteral administration, polypeptides of the invention will be formulated in an injectable form combined with a pharmaceutically acceptable parenteral vehicle. Such vehicles are well known in the art and examples include water, saline, Ringer's solution, dextrose solution, and solutions consisting of small amounts of the human serum albumin. The vehicle may contain minor amounts of additives that maintain the isotonicity and stability of the polypeptide or other active ingredient. The preparation of such solutions is within the skill of the art.

4.12 Pharmaceutical Formulations and Routes of Administration

A protein or other composition of the present invention (from whatever source derived, including without limitation from recombinant and non-recombinant sources and including antibodies and other binding partners of the polypeptides of the invention) may be administered to a patient in need, by itself, or in pharmaceutical compositions where it is mixed with suitable carriers or excipient(s) at doses to treat or ameliorate a variety of disorders. Such a composition may optionally contain (in addition to protein or other active ingredient and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. In further compositions, proteins of the invention may be combined with other agents beneficial to the treatment of the disease or disorder in question. These agents include various growth factors such as epidermal growth factor (EGF), platelet-derived growth factor (PDGF), transforming growth factors (TGF-α and TGF-β), insulin-like growth factor (IGF), as well as cytokines described herein.

The pharmaceutical composition may further contain other agents which either enhance the activity of the protein or other active ingredient or complement its activity or use in treatment. Such additional factors and/or agents may be included in the pharmaceutical composition to produce a synergistic effect with protein or other active ingredient of the invention, or to minimize side effects. Conversely, protein or other active ingredient of the present invention may be included in formulations of the particular clotting factor, cytokine, lymphokine, other hematopoietic factor, thrombolytic or anti-thrombotic factor, or anti-inflammatory agent to minimize side effects of the clotting factor, cytokine, lymphokine, other hematopoietic factor, thrombolytic or anti-thrombotic factor, or anti-inflammatory agent (such as IL-1Ra, IL-1Hy1, IL-1Hy2, anti-TNF, corticosteroids, immunosuppressive agents). A protein of the present invention may be active in multimers (e.g., heterodimers or homodimers) or complexes with itself or other proteins. As a result, pharmaceutical compositions of the invention may comprise a protein of the invention in such multimeric or complexed form.

As an alternative to being included in a pharmaceutical composition of the invention including a first protein, a second protein or a therapeutic agent may be concurrently administered with the first protein (e.g., at the same time, or at differing times provided that therapeutic concentrations of the combination of agents is achieved at the treatment site). Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment or use of the present invention, a therapeutically effective amount of protein or other active ingredient of the present invention is administered to a mammal having a condition to be treated. Protein or other active ingredient of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein or other active ingredient of the present invention may be administered either simultaneously with the cytokine(s), lymphokine(s), other hematopoietic factor (s), thrombolytic or anti-thrombotic factors, or sequentially. If administered sequentially, the attending physician will decide on the appropriate sequence of administering protein or other active ingredient of the present invention in combination with cytokine(s), lymphokine(s), other hematopoietic factor(s), thrombolytic or anti-thrombotic factors.

4.12.1 Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein or other active ingredient of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

Alternately, one may administer the compound in a local rather than systemic manner, for example, via injection of the compound directly into a arthritic joints or in fibrotic tissue, often in a depot or sustained release formulation. In order to prevent the scarring process frequently occurring as complication of glaucoma surgery, the compounds may be administered topically, for example, as eye drops. Furthermore, one may administer the drug in a targeted drug delivery system, for example, in a liposome coated with a specific antibody, targeting, for example, arthritic or fibrotic tissue. The liposomes will be targeted to and taken up selectively by the afflicted tissue.

The polypeptides of the invention are administered by any route that delivers an effective dosage to the desired site of action. The determination of a suitable route of administration and an effective dosage for a particular indication is within the level of skill in the art. Preferably for wound treatment, one administers the therapeutic compound directly to the site. Suitable dosage ranges for the polypeptides of the invention can be extrapolated from these dosages or from similar studies in appropriate animal models. Dosages can then be adjusted as necessary by the clinician to provide maximal therapeutic benefit.

4.12.2 Compositions/formulations

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of protein or other active ingredient of the present invention is administered orally, protein or other active ingredient of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein or other active ingredient of the present invention, and preferably from about 25 to 90% protein or other active ingredient of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein or other active ingredient of the present invention, and preferably from about 1 to 50% protein or other active ingredient of the present invention.

When a therapeutically effective amount of protein or other active ingredient of the present invention is administered by intravenous, cutaneous or subcutaneous injection, protein or other active ingredient of the present invention will be in the form of a pyrogen-free, parenterally acceptable aqueous solution. The preparation of such parenterally acceptable protein or other active ingredient solutions, having due regard to pH, isotonicity, stability, and the like, is within the skill in the art. A preferred pharmaceutical composition for intravenous, cutaneous, or subcutaneous injection should contain, in addition to protein or other active ingredient of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained from a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a co-solvent system comprising benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein or other active ingredient stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the active ingredients of the invention may be provided as salts with pharmaceutically compatible counter ions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) or other active ingredient(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithins, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The amount of protein or other active ingredient of the present invention in the pharmaceutical composition of the present invention will depend upon the nature and severity of the condition being treated, and on the nature of prior treatments which the patient has undergone. Ultimately, the attending physician will decide the amount of protein or other active ingredient of the present invention with which to treat each individual patient. Initially, the attending physician will administer low doses of protein or other active ingredient of the present invention and observe the patient's response. Larger doses of protein or other active ingredient of the present invention may be administered until the optimal therapeutic effect is obtained for the patient, and at that point the dosage is not increased further. It is contemplated that the various pharmaceutical compositions used to practice the method of the present invention should contain about 0.01 $\mu$g to about 100 mg (preferably about 0.1 $\mu$g to about 10 mg, more preferably about 0.1 $\mu$g to about 1 mg) of protein or other active ingredient of the present invention per kg body weight. For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein or other active-ingredient of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing or other active ingredient-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalcium phosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorption of the protein from the polymer matrix and to provide appropriate handling of the composition, yet not so much that the progenitor cells are prevented from infiltrating the matrix, thereby providing the protein the opportunity to assist the osteogenic activity of the progenitor cells. In further compositions, proteins or other active ingredients of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-$\alpha$ and TGF-$\beta$), and insulin-like growth factor (IGF).

The therapeutic compositions are also presently valuable for veterinary applications. Particularly domestic animals and thoroughbred horses, in addition to humans, are desired patients for such treatment with proteins or other active ingredients of the present invention. The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical-composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA). Cells may also be cultured ex vivo in the presence of proteins of the present invention in order to proliferate or to produce a desired effect on or activity in such cells. Treated cells can then be introduced in vivo for therapeutic purposes.

4.12.3 Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amount is well within the capability of those skilled in the art, especially in light of the detailed disclosure provided herein. For any compound used in the method of the invention, the therapeutically effective dose can be estimated initially from appropriate in vitro assays. For example, a dose can be formulated in animal models to achieve a circulating concentration range that can be used to more accurately determine useful doses in humans. For example, a dose can be formulated in animal models to achieve a circulating concentration range that includes the $IC_{50}$ as determined in cell culture (i.e., the concentration of the test compound which achieves a half-maximal inhibition of the protein's biological activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p. 1. Dosage amount and interval may be adjusted individually to provide plasma levels of the active moiety which are sufficient to maintain the desired effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%. In cases of local administration or selective uptake, the effective local concentration of the drug may not be related to plasma concentration.

An exemplary dosage regimen for polypeptides or other compositions of the invention will be in the range of about 0.01 μg/kg to 100 mg/kg of body weight daily, with the preferred dose being about 0.1 μg/kg to 25 mg/kg of patient body weight daily, varying in adults and children. Dosing may be once daily, or equivalent doses may be delivered at longer or shorter intervals.

The amount of composition administered will, of course, be dependent on the subject being treated, on the subject's age and weight, the severity of the affliction, the manner of administration and the judgment of the prescribing physician.

4.12.4 Packaging

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

4.13 Antibodies

Also included in the invention are antibodies to proteins, or fragments of proteins of the invention. The term "antibody" as used herein refers to immunoglobulin molecules and immunologically active portions of immunoglobulin (Ig) molecules, i.e., molecules that contain an antigen-binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated related protein of the invention may be intended to serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NO: 18–34, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a surface region of the protein, e.g., a hydrophilic region. A hydrophobicity analysis of the human related protein sequence will indicate which regions of a related protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad Sci. USA* 78: 3824–3828; Kyte and Doolittle 1982, *J. Mol. Biol.* 157: 105–142, each of which is incorporated herein by reference in its entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

The term "specific for" indicates that the variable regions of the antibodies of the invention recognize and bind polypeptides of the invention exclusively (i.e., able to distinguish the polypeptide of the invention from other similar polypeptides despite sequence identity, homology, or similarity found in the family of polypeptides), but may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies that recognize and bind fragments of the polypeptides of the invention are also contemplated, provided that the antibodies are first and foremost specific for, as defined above, full-length polypeptides of the invention. As with antibodies that are specific for full length polypeptides of the invention, antibodies of the invention that recognize fragments are those which can distinguish polypeptides from the same family of polypeptides despite inherent sequence identity, homology, or similarity found in the family of proteins.

Antibodies of the invention are useful for, for example, therapeutic purposes (by modulating activity of a polypeptide of the invention), diagnostic purposes to detect or quantitate a polypeptide of the invention, as well as purification of a polypeptide of the invention. Kits comprising an antibody of the invention for any of the purposes described herein are also comprehended. In general, a kit of the invention also includes a control antigen for which the antibody is immunospecific. The invention further provides a hybridoma that produces an antibody according to the invention. Antibodies of the invention are useful for detection and/or purification of the polypeptides of the invention.

Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

The labeled antibodies of the present invention can be used for in vitro, in vivo, and in situ assays to identify cells or tissues in which a fragment of the polypeptide of interest is expressed. The antibodies may also be used directly in therapies or other diagnostics. The present invention further provides the above-described antibodies immobilized on a solid support. Examples of such solid supports include plastics such as polycarbonate, complex carbohydrates such as agarose and Sepharose®, acrylic resins and such as polyacrylamide and latex beads. Techniques for coupling antibodies to such solid supports are well known in the art (Weir, D. M. et al., "Handbook of Experimental Immunology" 4th Ed., Blackwell Scientific Publications, Oxford, England, Chapter 10 (1986); Jacoby, W. D. et al., Meth. Enzym. 34 Academic Press, N.Y. (1974)). The immobilized antibodies of the present invention can be used for in vitro, in vivo, and in situ assays as well as for immuno-affinity purification of the proteins of the present invention.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

4.13.1 Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface-active substances (e.g., lysolecithin, pluronic polyols, polyanions, peptides, oil emulsions, dinitrophenol, etc.), adjuvants usable in humans such as Bacille Calmette-Guerin and Corynebacterium parvum, or similar immunostimulatory agents. Additional examples of adjuvants that can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

4.13.2 Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen-binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59–103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, Marcel Dekker, Inc., New York, (1987) pp. 51–63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980). Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

4.13.3 Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. (See also U.S. Pat. No. 5,225,539). In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, *Curr. Op. Struct. Biol.*, 2:593–596 (1992)).

4.13.4 Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: Monoclonal Antibodies and Cancer Therapy, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: Monoclonal Antibodies and Cancer Therapy, Alan R. Liss, Inc., pp. 77–96).

In addition, human antibodies can also be produced using additional techniques, including phage display libraries (Hoogenboom and Winter, *J. Mol. Biol.*, 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology* 10, 779–783 (1992)); Lonberg et al. (*Nature* 368 856–859 (1994)); Morrison (*Nature* 368, 812–13 (1994)); Fishwild et al, (*Nature Biotechnology* 14, 845–51 (1996)); Neuberger (*Nature Biotechnology* 14, 826 (1996)); and Lonberg and Huszar (*Intern. Rev. Immunol.* 13 65–93 (1995)).

Human antibodies may additionally be produced using transgenic nonhuman animals that are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells that secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

4.13.5 Fab Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

4.13.6 Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., 1991 EMBO J., 10:3655–3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers that are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., *J. Exp. Med.* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

4.13.7 Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

4.13.8 Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med., 176: 1191–1195 (1992) and Shopes, J. Immunol., 148: 2918–2922 (1992). Homodimeric antibodies with enhanced anti-tumor activity can also be prepared using heterobifunctional cross-linkers as described in Wolff et al. Cancer Research, 53: 2560–2565 (1993). Alternatively, an antibody can be engineered that has dual Fc regions and can thereby have enhanced complement lysis and ADCC capabilities. See Stevenson et al., Anti-Cancer Drug Design, 3: 219–230 (1989).

4.13.9 Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

4.14 Computer Readable Sequences

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention. As used herein, "recorded" refers to a process for storing information on computer readable medium. A skilled artisan can readily adopt any of the presently known methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the nucleotide sequence information of the present invention.

By providing any of the nucleotide sequences SEQ ID NOs: 1–17 or a representative fragment thereof; or a nucleotide sequence at least 95% identical to any of the nucleotide sequences of SEQ ID NOs: 1–17 in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., J. Mol. Biol. 215:403–410 (1990)) and BLAZE (Brutlag et al., Comp. Chem. 17:203–207 (1993)) search algorithms on a Sybase system is used to identify open reading frames (ORFs) within a nucleic acid sequence. Such ORFs may be protein encoding fragments and may be useful in producing commercially important proteins such as enzymes used in fermentation reactions and in the production of commercially useful metabolites.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention. As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of a known sequence which match a particular target sequence or target motif. A variety of known algorithms are disclosed publicly and a variety of commercially available software for conducting search means are and can be used in the computer-based systems of the present invention. Examples of such software includes, but is not limited to, Smith-Waterman, MacPattern (EMBL), BLASTN and BLASTA (NPOLYPEPTIDEIA). A skilled artisan can readily recognize that any one of the available algorithms or implementing software packages for conducting homology searches can be adapted for use in the present computer-based systems. As used herein, a "target sequence" can be any nucleic acid or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 300 amino acids, more preferably from about 30 to 100 nucleotide residues. However, it is well recognized that searches for commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

4.15 Triple Helix Formation

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are preferably 20 to 40 bases in length and are designed to be complementary to a region of the gene involved in transcription (triple helix—see Lee et al., Nucl. Acids Res. 6:3073 (1979); Cooney et al., Science 15241:456 (1988); and Dervan et al., Science 251:1360 (1991)) or to the mRNA itself (antisense—Olmno, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

4.16 Diagnostic Assays and Kits

The present invention further provides methods to identify the presence or expression of one of the ORFs of the present invention, or homolog thereof, in a test sample, using a nucleic acid probe or antibodies of the present invention, optionally conjugated or otherwise associated with a suitable label.

In general, methods for detecting a polynucleotide of the invention can comprise contacting a sample with a compound that binds to and forms a complex with the polynucleotide for a period sufficient to form the complex, and detecting the complex, so that if a complex is detected, a polynucleotide of the invention is detected in the sample. Such methods can also comprise contacting a sample under stringent hybridization conditions with nucleic acid primers that anneal to a polynucleotide of the invention under such conditions, and amplifying annealed polynucleotides, so that if a polynucleotide is amplified, a polynucleotide of the invention is detected in the sample.

In general, methods for detecting a polypeptide of the invention can comprise contacting a sample with a compound that binds to and forms a complex with the polypeptide for a period sufficient to form the complex, and detecting the complex, so that if a complex is detected, a polypeptide of the invention is detected in the sample.

In detail, such methods comprise incubating a test sample with one or more of the antibodies or one or more of the nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985). The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention. Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

4.17 Medical Imaging

The novel polypeptides and binding partners of the invention are useful in medical imaging of sites expressing the molecules of the invention (e.g., where the polypeptide of the invention is involved in the immune response, for imaging sites of inflammation or infection). See, e.g., Kunkel et al., U.S. Pat. No. 5,413,778. Such methods involve chemical attachment of a labeling or imaging agent, administration of the labeled polypeptide to a subject in a pharmaceutically acceptable carrier, and imaging the labeled polypeptide in vivo at the target site.

4.18 Screening Assays

Using the isolated proteins and polynucleotides of the invention, the present invention further provides methods of obtaining and identifying agents which bind to a polypeptide encoded by an ORF corresponding to any of the nucleotide sequences set forth in SEQ ID NOs: 1–17, or bind to a specific domain of the polypeptide encoded by the nucleic acid. In detail, said method comprises the steps of:

(a) contacting an agent with an isolated protein encoded by an ORF of the present invention, or nucleic acid of the invention; and (b) determining whether the agent binds to said protein or said nucleic acid.

In general, therefore, such methods for identifying compounds that bind to a polynucleotide of the invention can comprise contacting a compound with a polynucleotide of the invention for a time sufficient to form a polynucleotide/compound complex, and detecting the complex, so that if a polynucleotide/compound complex is detected, a compound that binds to a polynucleotide of the invention is identified.

Likewise, in general, therefore, such methods for identifying compounds that bind to a polypeptide of the invention can comprise contacting a compound with a polypeptide of the invention for a time sufficient to form a polypeptide/compound complex, and detecting the complex, so that if a polypeptide/compound complex is detected, a compound that binds to a polynucleotide of the invention is identified.

Methods for identifying compounds that bind to a polypeptide of the invention can also comprise contacting a compound with a polypeptide of the invention in a cell for a time sufficient to form a polypeptide/compound complex, wherein the complex drives expression of a receptor gene sequence in the cell, and detecting the complex by detecting reporter gene sequence expression, so that if a polypeptide/compound complex is detected, a compound that binds a polypeptide of the invention is identified.

Compounds identified via such methods can include compounds which modulate the activity of a polypeptide of the invention (that is, increase or decrease its activity, relative to activity observed in the absence of the compound). Alternatively, compounds identified via such methods can include compounds which modulate the expression of a polynucleotide of the invention (that is, increase or decrease expression relative to expression levels observed in the absence of the compound). Compounds, such as compounds identified via the methods of the invention, can be tested using standard assays well known to those of skill in the art for their ability to modulate activity/expression.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention. Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like, capable of binding to a specific peptide sequence, in order to generate rationally designed antipeptide peptides, for example see Hurby et al., Application of Synthetic Peptides: Antisense Peptides," In Synthetic Peptides, A User's Guide, W. H. Freeman, N.Y. (1992), pp. 289–307, and Kaspczak et al., Biochemistry 28:9230–8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control. One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods preferably contain 20 to 40 bases and are designed to be complementary to a region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents.

Agents which bind to a protein encoded by one of the ORFs of the present invention can be used as a diagnostic agent. Agents which bind to a protein encoded by one of the ORFs of the present invention can be formulated using known techniques to generate a pharmaceutical composition.

4.19 Use of Nucleic Acids as Probes

Another aspect of the subject invention is to provide for polypeptide-specific nucleic acid hybridization probes capable of hybridizing with naturally occurring nucleotide sequences. The hybridization probes of the subject invention may be derived from any of the nucleotide sequences SEQ ID NOs: 1–17. Because the corresponding gene is only expressed in a limited number of tissues, a hybridization probe derived from of any of the nucleotide sequences SEQ ID NOs: 1–17 can be used as an indicator of the presence of RNA of cell type of such a tissue in a sample.

Any suitable hybridization technique can be employed, such as, for example, in situ hybridization. PCR as described in U.S. Pat. Nos. 4,683,195 and 4,965,188 provides additional uses for oligonucleotides based upon the nucleotide sequences. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides. The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

4.20 Preparation of Support Bound Oligonucleotides

Oligonucleotides, i.e., small nucleic acid segments, may be readily prepared by, for example, directly synthesizing the oligonucleotide by chemical means, as is commonly practiced using an automated oligonucleotide synthesizer.

Support bound oligonucleotides may be prepared by any of the methods known to those of skill in the art using any suitable support such as glass, polystyrene or Teflon. One strategy is to precisely spot oligonucleotides synthesized by standard synthesizers. Immobilization can be achieved using passive adsorption (Inouye & Hondo, (1990) J. Clin. Microbiol. 28(6) 1469–72); using UV light (Nagata et al., 1985; Dahlen et al., 1987; Morrissey & Collins, (1989) Mol. Cell Probes 3(2) 189–207) or by covalent binding of base modified DNA (Keller et al., 1988; 1989); all references being specifically incorporated herein.

Another strategy that may be employed is the use of the strong biotin-streptavidin interaction as a linker. For example, Broude et al. (1994) Proc. Natl. Acad. Sci. USA 91(8) 3072–6, describe the use of biotinylated probes, although these are duplex probes, that are immobilized on streptavidin-coated magnetic beads. Streptavidin-coated beads may be purchased from Dynal, Oslo. Of course, this same linking chemistry is applicable to coating any surface with streptavidin. Biotinylated probes may be purchased from various sources, such as, e.g., Operon Technologies (Alameda, Calif.).

Nunc Laboratories (Naperville, Ill.) is also selling suitable material that could be used. Nunc Laboratories have developed a method by which DNA can be covalently bound to the microwell surface termed Covalink NH. CovaLink NH is a polystyrene surface grafted with secondary amino groups (>NH) that serve as bridge-heads for further covalent coupling. CovaLink Modules may be purchased from Nunc Laboratories. DNA molecules may be bound to CovaLink exclusively at the 5'-end by a phosphoramidate bond, allowing immobilization of more than 1 pmol of DNA (Rasmussen et al., (1991) Anal. Biochem. 198(1) 138–42).

The use of CovaLink NH strips for covalent binding of DNA molecules at the 5'-end has been described (Rasmussen et al., (1991). In this technology, a phosphoramidate bond is employed (Chu et al., (1983) Nucleic Acids Res. 11(8) 6513–29). This is beneficial as immobilization using only a single covalent bond is preferred. The phosphoramidate bond joins the DNA to the CovaLink NH secondary amino groups that are positioned at the end of spacer arms covalently grafted onto the polystyrene surface through a 2 nm long spacer arm. To link an oligonucleotide to CovaLink NH via an phosphoramidate bond, the oligonucleotide terminus must have a 5'-end phosphate group. It is, perhaps, even possible for biotin to be covalently bound to CovaLink and then streptavidin used to bind the probes.

More specifically, the linkage method includes dissolving DNA in water (7.5 ng/ul) and denaturing for 10 min. at 95° C. and cooling on ice for 10 min. Ice-cold 0.1 M 1-methylimidazole, pH 7.0 (1-MeIm$_7$), is then added to a final concentration of 10 mM 1-MeIm$_7$. A ss DNA solution is then dispensed into CovaLink NH strips (75 ul/well) standing on ice.

Carbodiimide 0.2 M 1-ethyl-3-(3-dimethylaminopropyl)-carbodiimide (EDC), dissolved in 10 mM 1-MeIm$_7$, is made fresh and 25 ul added per well. The strips are incubated for 5 hours at 50° C. After incubation the strips are washed using, e.g., Nunc-Immuno Wash; first the wells are washed 3 times, then they are soaked with washing solution for 5 min., and finally they are washed 3 times (where in the washing solution is 0.4 N NaOH, 0.25% SDS heated to 50° C.).

It is contemplated that a further suitable method for use with the present invention is that described in PCT Patent Application WO 90/03382 (Southern & Maskos), incorporated herein by reference. This method of preparing an oligonucleotide bound to a support involves attaching a nucleoside 3'-reagent through the phosphate group by a covalent phosphodiester link to aliphatic hydroxyl groups carried by the support. The oligonucleotide is then synthesized on the supported nucleoside and protecting groups removed from the synthetic oligonucleotide chain under standard conditions that do not cleave the oligonucleotide from the support. Suitable reagents include nucleoside phosphoramidite and nucleoside hydrogen phosphorate.

An on-chip strategy for the preparation of DNA probe for the preparation of DNA probe arrays may be employed. For example, addressable laser-activated photodeprotection may be employed in the chemical synthesis of oligonucleotides directly on a glass surface, as described by Fodor et al. (1991) Science 251(4995) 767–73, incorporated herein by reference. Probes may also be immobilized on nylon supports as described by Van Ness et al. (1991) Nucleic Acids Res. 19(12) 3345–50; or linked to Teflon using the method of Duncan & Cavalier (1988) Anal. Biochem. 169(1) 104–8; all references being specifically incorporated herein.

To link an oligonucleotide to a nylon support, as described by Van Ness et al. (1991), requires activation of the nylon surface via alkylation and selective activation of the 5'-amine of oligonucleotides with cyanuric chloride.

One particular way to prepare support bound oligonucleotides is to utilize the light-generated synthesis described by Pease et al., (1994) PNAS USA 91(11) 5022–6, incorporated herein by reference). These authors used current photolithographic techniques to generate arrays of immobilized oligonucleotide probes (DNA chips). These methods, in which light is used to direct the synthesis of oligonucleotide probes in high-density, miniaturized arrays, utilize photolabile 5'-protected N-acyl-deoxynucleoside phosphoramidites, surface linker chemistry and versatile combinatorial synthesis strategies. A matrix of 256 spatially defined oligonucleotide probes may be generated in this manner.

4.21 Preparation of Nucleic Acid Fragments

The nucleic acids may be obtained from any appropriate source, such as cDNAs, genomic DNA, chromosomal DNA, microdissected chromosome bands, cosmid or YAC inserts, and RNA, including mRNA without any amplification steps. For example, Sambrook et al. (1989) describes three protocols for the isolation of high molecular weight DNA from mammalian cells (p. 9.14–9.23).

DNA fragments may be prepared as clones in M13, plasmid or lambda vectors and/or prepared directly from genomic DNA or cDNA by PCR or other amplification methods. Samples may be prepared or dispensed in multi-well plates. About 100–1000 ng of DNA samples may be prepared in 2–500 ml of final volume.

The nucleic acids would then be fragmented by any of the methods known to those of skill in the art including, for example, using restriction enzymes as described at 9.24–9.28 of Sambrook et al. (1989), shearing by ultrasound and NaOH treatment.

Low pressure shearing is also appropriate, as described by Schriefer et al. (1990) Nucleic Acids Res. 18(24) 7455–6, incorporated herein by reference). In this method, DNA samples are passed through a small French pressure cell at a variety of low to intermediate pressures. A lever device allows controlled application of low to intermediate pressures to the cell. The results of these studies indicate that low-pressure shearing is a useful alternative to sonic and enzymatic DNA fragmentation methods.

One particularly suitable way for fragmenting DNA is contemplated to be that using the two base recognition endonuclease, CviJI, described by Fitzgerald et al. (1992) Nucleic Acids Res. 20(14) 3753–62. These authors described an approach for the rapid fragmentation and fractionation of DNA into particular sizes that they contemplated to be suitable for shotgun cloning and sequencing.

The restriction endonuclease CviJI normally cleaves the recognition sequence PuGCPy between the G and C to leave blunt ends. Atypical reaction conditions, which alter the specificity of this enzyme (CviJI), yield a quasi-random distribution of DNA fragments form the small molecule pUC19 (2688 base pairs). Fitzgerald et al. (1992) quantitatively evaluated the randomness of this fragmentation strategy, using a CviJI digest of pUC19 that was size fractionated by a rapid gel filtration method and directly ligated, without end repair, to a lac Z minus M13 cloning vector. Sequence analysis of 76 clones showed that CviJI** restricts pyGCPy and PuGCPu, in addition to PuGCPy sites, and that new sequence data is accumulated at a rate consistent with random fragmentation.

As reported in the literature, advantages of this approach compared to sonication and agarose gel fractionation include: smaller amounts of DNA are required (0.2–0.5 ug instead of 2–5 ug); and fewer steps are involved (no preligation, end repair, chemical extraction, or agarose gel electrophoresis and elution are needed.

Irrespective of the manner in which the nucleic acid fragments are obtained or prepared, it is important to denature the DNA to give single stranded pieces available for hybridization. This is achieved by incubating the DNA solution for 2–5 minutes at 80–90° C. The solution is then cooled quickly to 2° C. to prevent renaturation of the DNA fragments before they are contacted with the chip. Phosphate groups must also be removed from genomic DNA by methods known in the art.

4.22 Preparation of DNA Arrays

Arrays may be prepared by spotting DNA samples on a support such as a nylon membrane. Spotting may be performed by using arrays of metal pins (the positions of which correspond to an array of wells in a microtiter plate) to repeated by transfer of about 20 nl of a DNA solution to a nylon membrane. By offset printing, a density of dots higher than the density of the wells is achieved. One to 25 dots may be accommodated in 1 mm$^2$, depending on the type of label used. By avoiding spotting in some preselected number of rows and columns, separate subsets (subarrays) may be formed. Samples in one subarray may be the same genomic segment of DNA (or the same gene) from different individuals, or may be different, overlapped genomic clones. Each of the subarrays may represent replica spotting of the same samples. In one example, a selected gene segment may be amplified from 64 patients. For each patient, the amplified gene segment may be in one 96-well plate (all 96 wells containing the same sample). A plate for each of the 64 patients is prepared. By using a 96-pin device, all samples may be spotted on one 8×12 cm membrane. Subarrays may contain 64 samples, one from each patient. Where the 96 subarrays are identical, the dot span may be 1 mm$^2$ and there may be a 1 mm space between subarrays.

Another approach is to use membranes or plates (available from NUNC, Naperville, Ill.) which may be partitioned by physical spacers e.g. a plastic grid molded over the membrane, the grid being similar to the sort of membrane applied to the bottom of multiwell plates, or hydrophobic strips. A fixed physical spacer is not preferred for imaging by exposure to flat phosphor-storage screens or x-ray films.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples. The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments. Consequently, the only limitations which should be placed upon the scope of the invention are those which appear in the appended claims.

All references cited within the body of the instant specification are hereby incorporated by reference in their entirety.

5. EXAMPLES

5.1 Example 1

Novel Nucleic Acid Sequences Obtained from Various Libraries

A plurality of novel nucleic acids were obtained from cDNA libraries prepared from various human tissues and in some cases isolated from a genomic library derived from human chromosome using standard PCR, SBH sequence signature analysis and Sanger sequencing techniques. The inserts of the library were amplified with PCR using primers specific for the vector sequences which flank the inserts. Clones from cDNA libraries were spotted on nylon membrane filters and screened with oligonucleotide probes (e.g., 7-mers) to obtain signature sequences. The clones were clustered into groups of similar or identical sequences. Representative clones were selected for sequencing.

In some cases, the 5' sequence of the amplified inserts was then deduced using a typical Sanger sequencing protocol. PCR products were purified and subjected to fluorescent dye terminator cycle sequencing. Single pass gel sequencing was done using a 377 Applied Biosystems (ABI) sequencer to obtain the novel nucleic acid sequences. In some cases RACE (Random Amplification of cDNA Ends) was performed to further extend the sequence in the 5' direction.

5.2 Example 2

Novel Nucleic Acids

The novel nucleic acids of the present invention of the invention were assembled from sequences that were obtained from a cDNA library by methods described in Example 1 above, and in some cases sequences obtained from one or more public databases. The nucleic acids were assembled using an EST sequence as a seed. Then a recursive algorithm was used to extend the seed EST into an extended assemblage, by pulling additional sequences from different databases (i.e., Hyseq's database containing EST sequences, dbEST version 115, gb pri 115 and UniGene version 103 and exons from public domain genomic sequences predicted by Genscan) that belong to this assemblage. The algorithm terminated when there was no additional sequences from the above databases that would extend the assemblage. Inclusion of component sequences into the assemblage was based on a BLASTN hit to the extending assemblage with BLAST score greater than 300 and percent identity greater than 95%.

Using PHRAP (Univ. of Washington) or CAP4 (Paracel), a full length gene cDNA sequence and its corresponding protein sequence were generated from the assemblage. Any frame shifts and incorrect stop codons were corrected by hand editing. During editing, the sequence was checked using FASTY and/or BLAST against Genbank (i.e., dbEST version 121, gb pri 121, UniGene version 121, Genpept release 121). Other computer programs which may have been used in the editing process were phredPhrap and Consed (University of Washington) and ed-ready, ed-ext and cg-zip-2 (Hyseq, Inc.). The full-length nucleotide and amino acid sequences, including splice variants resulting from these procedures are shown in the Sequence Listing as SEQ ID NOS: 1–34.

Table 1 shows the various tissue sources of SEQ ID NO: 1–17.

The homology for SEQ ID NO: 1–17 were obtained by a BLASTP version 2.0 al 19MP-WashU search against Genpept release 121 and the amino acid version of Genseq released on Feb. 15, 2001, using BLAST algorithm. The results showed homologues for SEQ ID NO: 1–17 from Genpept and Genseq. The homologues with identifiable functions for SEQ ID NO: 1–17 are shown in Table 2 below.

Using eMatrix software package (Stanford University, Stanford, Calif.) (Wu et al., J. Comp. Biol., Vol. 6 pp. 219–235 (1999) herein incorporated by reference), all the sequences were examined to determine whether they had identifiable signature regions. Table 3 shows the signature region found in the polypeptides encoded by the indicated polynucleotide sequences, the description of the signature, the eMatrix p-value(s) and the position(s) of the signature within the polypeptide sequence.

Using the pFam software program (Sonnhammer et al., Nucleic Acids Res., Vol. 26(1) pp. 320–322 (1998) herein incorporated by reference) all the polypeptide sequences were examined for domains with homology to certain peptide domains. Table 4 shows the name of the domain found, the description, the p-value and the pFam score for the identified domain within the polypeptide encoded by the indicated polynucleotide sequence.

The nucleotide sequence within the sequences that codes for signal peptide sequences and their cleavage sites can be determined from using Neural Network SignalP V1.1 program (from Center for Biological Sequence Analysis, The Technical University of Denmark). The process for identifying prokaryotic and eukaryotic signal peptides and their cleavage sites are also disclosed by Henrik Nielson, Jacob Engelbrecht, Soren Brunak, and Gunnar von Heijne in the publication "Identification of prokaryotic and eukaryotic signal peptides and prediction of their cleavage sites" Protein Engineering, Vol. 10, no. 1, pp. 1–6 (1997), incorporated herein by reference. A maximum S score and a mean S score, as described in the Nielson et as reference, was obtained for the polypeptide sequences. Table 5 shows the position of the signal peptide in each of the polypeptides and the maximum score and mean score associated with that signal peptide.

TABLE 1

| TISSUE ORIGIN | LIBRARY/ RNA SOURCE | HYSEQ LIBRARY NAME | SEQ ID NOS: |
|---|---|---|---|
| adult brain | GIBCO | ABD003 | 2 9 |
| adult brain | Clontech | ABR006 | 12 |
| adult brain | Clontech | ABR008 | 4–6 |

TABLE 1-continued

| TISSUE ORIGIN | LIBRARY/ RNA SOURCE | HYSEQ LIBRARY NAME | SEQ ID NOS: |
|---|---|---|---|
| adult brain | Invitrogen | ABT004 | 15 |
| cultured preadipocytes | Stratagene | ADP001 | 4 9 |
| adrenal gland | Clontech | ADR002 | 2 9 |
| adult heart | GIBCO | AHR001 | 3 10 |
| adult kidney | GIBCO | AKD001 | 2 10 15–17 |
| adult kidney | Invitrogen | AKT002 | 9 11 15–17 |
| adult lung | GIBCO | ALG001 | 11 |
| adult liver | Invitrogen | ALV002 | 15–17 |
| adult ovary | Invitrogen | AOV001 | 1 9–10 15 |
| placenta | Invitrogen | APL002 | 15 |
| adult spleen | GIBCO | ASP001 | 9–10 16–17 |
| bone marrow | Clontech | BMD001 | 10 |
| adult colon | Invitrogen | CLN001 | 7 15 |
| adult cervix | BioChain | CVX001 | 2 15–17 |
| diaphragm | BioChain | DIA002 | 9 |
| endothelial cells | Strategene | EDT001 | 9–10 |
| fetal brain | Clontech | FBR006 | 5 8 |
| fetal brain | Invitrogen | FBT002 | 15 |
| fetal heart | Invitrogen | FHR001 | 2 10 |
| fetal kidney | Clontech | FKD001 | 9–10 |
| fetal liver-spleen | Columbia University | FLS001 | 2 5 7 10–12 15 |
| fetal liver-spleen | Columbia University | FLS002 | 2 9–10 16–17 |
| fetal liver | Invitrogen | FLV001 | 10 15 |
| fetal liver | Clontech | FLV004 | 7 12 |
| fetal muscle | Invitrogen | FMS002 | 10 15 |
| fetal skin | Invitrogen | FSK001 | 2 12 14 |
| fetal skin | Invitrogen | FSK002 | 2 10 |
| umbilical cord | BioChain | FUC001 | 2 15 |
| fetal brain | GIBCO | HFB001 | 2 |
| infant brain | Columbia University | IB2002 | 10 |
| infant brain | Columbia University | IB2003 | 2 7 |
| infant brain | Columbia University | IBM002 | 2 |
| Lung, fibroblast | Strategene | LFB001 | 9 |
| lung tumor | Invitrogen | LGT002 | 2 7 11 16 |
| lymphocytes | ATCC | LPC001 | 1–2 12 |
| leukocyte | GIBCO | LUC001 | 9 |
| melanoma from cell line ATCC #CRL 1424 | Clontech | MEL004 | 3 |
| mammary gland | Invitrogen | MMG001 | 11 16–17 |
| placenta | Clontech | PLA003 | 5 |
| rectum | Invitrogen | REC001 | 16–17 |
| small intestine | Clontech | SIN001 | 2 15 |
| thymus | Clontech | THM001 | 15 |
| thymus | Clontech | THMc02 | 5 13 |
| thyroid gland | Clontech | THR001 | 2 9 |

TABLE 2

| SEQ ID NO: | CORRESPONDING SEQ ID NO. IN U.S. Ser. No. 09/540,217 | ACCESSION NUMBER | DESCRIPTION | SMITH-WATERMAN SCORE | % IDENTITY |
|---|---|---|---|---|---|
| 1 | 1327 1328 1329 1330 1331 | W87772 | *Homo sapiens* Human serum glucocorticoid-regulated kinase (H-SGK2) polypeptide. | 138 | 26 |
| 2 | 1472 1473 1474 | Y87259 | *Homo sapiens* Human signal peptide containing protein HSPP-36 SEQ ID NO: 36. | 2888 | 99 |
| 3 | 1502 | Y95002 | *Homo sapiens* Human secreted protein vc34_1, SEQ ID NO: 44. | 445 | 52 |
| 4 | 2005 2006 | gi3702174 | *Mus musculus* Fish protein | 795 | 69 |
| 5 | 3182 3183 | gi6694278 | *Homo sapiens* cell recognition molecule Caspr2 | 445 | 54 |
| 6 | 3637 3638 3639 | gi10764778 | *Homo sapiens* phosphoinositol 3-phosphate-binding protein-2 | 125 | 43 |
| 7 | 5419 5420 | gi1620870 | *Ciona intestinalis* myoplasmin-C1 | 329 | 28 |
| 8 | 11132 | gi11125348 | *Homo sapiens* putative protein kinase | 527 | 41 |
| 9 | 11646 11647 | gi306875 | *Homo sapiens* C protein | 1091 | 99 |
| 10 | 13998 13999 | gi10441465 | *Homo sapiens* actin filament associated protein | 1417 | 46 |
| 11 | 19572 | Y53032 | *Homo sapiens* Human secreted protein clone di393_2 protein sequence SEQ ID NO: 70. | 908 | 100 |
| 12 | 21068 21069 | Y53023 | *Homo sapiens* Human secreted protein clone qf662_3 protein sequence SEQ ID NO: 52. | 573 | 62 |
| 13 | 23896 23897 | gi207621 | *Rattus norvegicus* uromodulin | 227 | 32 |
| 14 | 26707 | gi1491720 | *Lycopersicon esculentum* extensin-like protein Dif10 | 115 | 24 |
| 15 | 27787 27788 27789 | G00511 | *Homo sapiens* Human secreted protein, SEQ ID NO: 4592. | 475 | 98 |
| 16 | 29582 29583 29584 29585 | gi8650435 | *Mus musculus* RalGDS-like protein 3 | 2786 | 77 |
| 17 | 29582 29583 29584 29585 | gi8650435 | *Mus musculus* RalGDS-like protein 3 | 2677 | 75 |

TABLE 3

| SEQ ID NO: | ACCESSION NO. | DESCRIPTION | RESULTS* |
|---|---|---|---|
| 1 | PR00497 | NEUTROPHIL CYTOSOL FACTOR P40 SIGNATURE | PR00497A 6.92 4.273e-09 138–156 |
| 4 | PR00498 | NEUTROPHIL CYTOSOL FACTOR 1 SIGNATURE | PR00498E 13.75 7.785e-14 183–203 PR00498C 8.33 5.500e-10 111–131 |
| 5 | DM00516 | 186 DISCOIDIN I N-TERMINAL. | DM00516 30.53 7.465e-13 131–176 |
| 8 | BL00492 | Clusterin proteins. | BL00492E 12.52 5.394e-09 389–438 |
| 13 | PR00023 | ZONA PELLUCIDA SPERM-BINDING PROTEIN SIGNATURE | PR00023D 17.19 6.308e-11 102–118 |

TABLE 3-continued

| SEQ ID NO: | ACCESSION NO. | DESCRIPTION | RESULTS* |
|---|---|---|---|
| 16 | BL00720 | Guanine-nucleotide dissociation stimulators CDC25 family sign. | BL00720B 16.57 7.097e-17 344–368 |
| 17 | BL00720 | Guanine-nucleotide dissociation stimulators CDC25 family sign. | BL00720B 16.57 7.097e-17 344–368 |

*Results include in order: accession number subtype; raw score; p-value; position of signature in amino acid sequence.

TABLE 4

| SEQ ID NO: | pFAM NAME | DESCRIPTION | p-value | pFAM SCORE |
|---|---|---|---|---|
| 1 | PX | PX domain | 1.6e-06 | 35.1 |
| 4 | PX | PX domain | 4.2e-22 | 86.9 |
| 5 | F5_F8_type_C | F5/8 type C domain | 1.4e-29 | 111.7 |
| 6 | PH | PH domain | 4.1e-10 | 41.2 |

TABLE 4-continued

| SEQ ID NO: | pFAM NAME | DESCRIPTION | p-value | pFAM SCORE |
|---|---|---|---|---|
| 8 | pkinase | Eukaryotic protein kinase domain | 8.4e-05 | 21.2 |
| 10 | PH | PH domain | 3.2e-22 | 84.4 |
| 13 | zona_pellucida | Zona pellucida-like domain | 6.9e-14 | 57.6 |
| 16 | RasGEF | RasGEF domain | 1.2e-64 | 228.2 |
| 17 | RasGEF | RasGEF domain | 1.2e-64 | 228.2 |

TABLE 5

| SEQ ID NO: | POSITION OF SIGNAL IN AMINO ACID SEQUENCE | maxS (MAXIMUM SCORE) | meanS (MEAN SCORE) |
|---|---|---|---|
| 3 | 1–30 | 0.996 | 0.884 |
| 5 | 1–25 | 0.985 | 0.864 |

What is claimed is:

1. An isolated polynucleotide comprising the nucleotide sequence of SEQ ID NO: 16.
2. An isolated polynucleotide comprising the nucleotide sequence which is 99% identical to the nucleic acid sequence of SEQ ID NO: 16.
3. An isolated polynucleotide of claim 1 wherein said polynucleotide comprises the full complementary sequence.
4. A vector comprising the polynucleotide of claim 1.
5. An expression vector comprising the polynucleotide of claim 1.
6. An isolated host cell genetically engineered to comprise the polynucleotide of claim 1.
7. An isolated host cell genetically engineered to comprise the polynucleotide of claim 1 operatively associated with a regulatory sequence that modulates expression of the polynucleotide in the host cell.

* * * * *